US011731132B2

(12) United States Patent
Krishnan et al.

(10) Patent No.: US 11,731,132 B2
(45) Date of Patent: *Aug. 22, 2023

(54) METHODS AND DEVICES FOR DETECTION OF MULTIPLE ANALYTES FROM A BIOLOGICAL SAMPLE

(71) Applicant: Biological Dynamics, Inc., San Diego, CA (US)

(72) Inventors: Rajaram Krishnan, San Diego, CA (US); Juan Pablo Hinestrosa Salazar, San Diego, CA (US); Robert Paul Turner, San Diego, CA (US); David Joseph Searson, San Diego, CA (US); James Gregory Madsen, San Diego, CA (US); Robert Kovelman, La Jolla, CA (US)

(73) Assignee: BIOLOGICAL DYNAMICS, INC., San Diego, CA (US)

( * ) Notice: Subject to any disclaimer, the term of this patent is extended or adjusted under 35 U.S.C. 154(b) by 418 days.

This patent is subject to a terminal disclaimer.

(21) Appl. No.: 16/955,707

(22) PCT Filed: Dec. 19, 2018

(86) PCT No.: PCT/US2018/066602
§ 371 (c)(1),
(2) Date: Jun. 18, 2020

(87) PCT Pub. No.: WO2019/126388
PCT Pub. Date: Jun. 27, 2019

(65) Prior Publication Data
US 2021/0101150 A1 Apr. 8, 2021

Related U.S. Application Data

(60) Provisional application No. 62/607,873, filed on Dec. 19, 2017.

(51) Int. Cl.
*B01L 3/00* (2006.01)
*C12Q 1/6806* (2018.01)
*G01N 21/64* (2006.01)

(52) U.S. Cl.
CPC ...... *B01L 3/502761* (2013.01); *C12Q 1/6806* (2013.01); *B01L 2300/0636* (2013.01);
(Continued)

(58) Field of Classification Search
CPC .......... B01L 3/502761; B01L 2400/04; B01L 2400/0424; B01L 2300/0636;
(Continued)

(56) References Cited

U.S. PATENT DOCUMENTS 5,632,957 A 5/1997 Heller et al.
5,958,791 A 9/1999 Roberts et al.
(Continued)

FOREIGN PATENT DOCUMENTS

CA 2870160 A1 10/2013
CN 1337580 A 2/2002
(Continued)

OTHER PUBLICATIONS

Angerer et al. Demonstration of tissue-specific gene expression by in situ hybridization. Methods Enzymol 152:649-660 (1987).
(Continued)

*Primary Examiner* — Terrell H Matthews
(74) *Attorney, Agent, or Firm* — Wilson Sonsini Goodrich & Rosati

(57) ABSTRACT

The present invention includes methods, devices and systems for isolating, identifying, analyzing, and quantifying biological materials from fluid samples. In various aspects, the methods, devices and systems may allow for a rapid procedure that requires a minimal amount of material and/or
(Continued)

results in high purity biological materials from complex fluids such as blood, serum, or plasma.

20 Claims, 12 Drawing Sheets

(52) U.S. Cl.
CPC ............... *B01L 2300/0645* (2013.01); *B01L 2400/0424* (2013.01); *G01N 2021/6439* (2013.01); *G01N 2800/26* (2013.01); *G01N 2800/7028* (2013.01)

(58) Field of Classification Search
CPC .......... B01L 2300/0645; C12Q 1/6806; C12Q 1/6809; G01N 2021/6439; G01N 2800/26; G01N 2800/7028
USPC ........................................................ 422/502
See application file for complete search history.

(56) References Cited

U.S. PATENT DOCUMENTS

| | | | |
|---|---|---|---|
| 6,149,789 A | 11/2000 | Benecke et al. | |
| 6,203,683 B1 | 3/2001 | Austin et al. | |
| 6,280,590 B1 | 8/2001 | Cheng et al. | |
| 6,289,590 B1 | 9/2001 | McDonald | |
| 6,294,063 B1 | 9/2001 | Becker et al. | |
| 6,335,167 B1 | 1/2002 | Pinkel et al. | |
| 6,352,838 B1* | 3/2002 | Krulevitch | C12N 15/101 435/34 |
| 6,403,367 B1 | 6/2002 | Cheng et al. | |
| 6,557,575 B1 | 5/2003 | Gerhardt et al. | |
| 6,749,736 B1 | 6/2004 | Fuhr et al. | |
| 6,824,664 B1 | 11/2004 | Austin et al. | |
| 6,887,362 B2 | 5/2005 | Huang et al. | |
| 7,081,189 B2 | 7/2006 | Squires et al. | |
| 7,105,081 B2 | 9/2006 | Gascoyne et al. | |
| 7,447,922 B1 | 11/2008 | Asbury et al. | |
| 7,611,908 B2* | 11/2009 | Miller | G01N 33/54313 422/417 |
| 7,615,381 B2* | 11/2009 | Masters | G01N 33/54313 422/417 |
| 7,648,844 B2* | 1/2010 | Srivastava | B01L 3/502761 435/7.1 |
| 7,709,262 B2 | 5/2010 | Cantor et al. | |
| 8,372,657 B2* | 2/2013 | Reboud | G01N 33/54366 422/534 |
| 8,383,061 B2* | 2/2013 | Prakash | G01N 1/2035 422/68.1 |
| 8,425,750 B2 | 4/2013 | Sugioka | |
| 8,603,791 B2 | 12/2013 | Krishnan et al. | |
| 8,815,554 B2 | 8/2014 | Krishnan et al. | |
| 8,815,555 B2 | 8/2014 | Krishnan et al. | |
| 8,871,481 B2 | 10/2014 | Krishnan et al. | |
| 8,877,470 B2 | 11/2014 | Krishnan et al. | |
| 8,932,447 B2 | 1/2015 | Heller et al. | |
| 8,932,815 B2 | 1/2015 | Krishnan et al. | |
| 8,969,059 B2 | 3/2015 | Krishnan et al. | |
| 9,005,941 B2 | 4/2015 | Krishnan et al. | |
| 9,034,578 B2 | 5/2015 | Krishnan et al. | |
| 9,034,579 B2 | 5/2015 | Krishnan et al. | |
| 9,169,521 B1 | 10/2015 | Rajagopal et al. | |
| 9,206,416 B2 | 12/2015 | Krishnan et al. | |
| 9,387,489 B2 | 7/2016 | Charlot et al. | |
| 9,499,812 B2 | 11/2016 | Krishnan et al. | |
| 9,682,385 B2 | 6/2017 | Charlot et al. | |
| 9,827,565 B2 | 11/2017 | Krishnan et al. | |
| 9,918,702 B2 | 3/2018 | Tariyal et al. | |
| 10,006,083 B2 | 6/2018 | Krishnan et al. | |
| 10,151,755 B2 | 12/2018 | Krek et al. | |
| 10,232,369 B2 | 3/2019 | Turner et al. | |
| 10,262,761 B1 | 4/2019 | Weintraub | |
| 10,818,379 B2 | 10/2020 | Krishnan et al. | |
| 2001/0045359 A1 | 11/2001 | Cheng et al. | |
| 2002/0036142 A1 | 3/2002 | Gascoyne et al. | |
| 2003/0146100 A1 | 8/2003 | Huang et al. | |
| 2004/0011650 A1* | 1/2004 | Zenhausern | B82Y 15/00 204/547 |
| 2004/0011651 A1 | 1/2004 | Becker et al. | |
| 2004/0052689 A1 | 3/2004 | Yao | |
| 2004/0086872 A1 | 5/2004 | Childers et al. | |
| 2004/0178068 A1 | 9/2004 | Gascoyne et al. | |
| 2004/0238052 A1 | 12/2004 | Karp et al. | |
| 2006/0063183 A1 | 3/2006 | Segawa et al. | |
| 2006/0096367 A1 | 5/2006 | Meyer et al. | |
| 2006/0102482 A1 | 5/2006 | Auerswald et al. | |
| 2006/0228749 A1 | 10/2006 | Wang et al. | |
| 2006/0257993 A1 | 11/2006 | McDevitt et al. | |
| 2006/0289341 A1 | 12/2006 | Muller et al. | |
| 2007/0080062 A1 | 4/2007 | Harnett et al. | |
| 2007/0095669 A1 | 5/2007 | Lau et al. | |
| 2007/0107910 A1 | 5/2007 | McGuire et al. | |
| 2007/0125650 A1 | 6/2007 | Scurati et al. | |
| 2007/0131554 A1 | 6/2007 | Yu et al. | |
| 2007/0141605 A1 | 6/2007 | Vann et al. | |
| 2007/0152206 A1 | 7/2007 | Cho et al. | |
| 2007/0240495 A1 | 10/2007 | Hirahara | |
| 2007/0284254 A1 | 12/2007 | Cho et al. | |
| 2007/0289341 A1 | 12/2007 | Hollenhorst et al. | |
| 2008/0120278 A1 | 5/2008 | Roe et al. | |
| 2009/0061450 A1 | 3/2009 | Hunter | |
| 2009/0314644 A1 | 12/2009 | Golan, II et al. | |
| 2009/0325813 A1 | 12/2009 | Wang et al. | |
| 2010/0090178 A1 | 4/2010 | Kosowsky et al. | |
| 2010/0155246 A1 | 6/2010 | Schnelle et al. | |
| 2010/0167072 A1 | 7/2010 | Chouai et al. | |
| 2010/0211407 A1 | 8/2010 | Duke et al. | |
| 2011/0009724 A1 | 1/2011 | Hill et al. | |
| 2011/0020785 A1 | 1/2011 | Lowery, Jr. et al. | |
| 2011/0100820 A1* | 5/2011 | Bachmann | B01L 3/502761 204/547 |
| 2011/0108422 A1 | 5/2011 | Heller et al. | |
| 2011/0139620 A1 | 6/2011 | Stumber et al. | |
| 2011/0192726 A1* | 8/2011 | Chen | G01N 33/5438 204/547 |
| 2012/0048403 A1 | 3/2012 | Chappel et al. | |
| 2012/0110620 A1 | 5/2012 | Kilar et al. | |
| 2012/0270207 A1 | 10/2012 | Sheehan et al. | |
| 2013/0052748 A1 | 2/2013 | Campbell et al. | |
| 2013/0189794 A1 | 7/2013 | Emeric et al. | |
| 2013/0237431 A1 | 9/2013 | Lo et al. | |
| 2013/0260372 A1 | 10/2013 | Buermann et al. | |
| 2013/0273640 A1 | 10/2013 | Krishnan et al. | |
| 2013/0274148 A1 | 10/2013 | Kain et al. | |
| 2014/0038222 A1 | 2/2014 | Alt et al. | |
| 2014/0054172 A1 | 2/2014 | Jonsson et al. | |
| 2014/0093871 A1 | 4/2014 | Shieh et al. | |
| 2014/0127697 A1 | 5/2014 | Krishnan et al. | |
| 2014/0138260 A1 | 5/2014 | Briman | |
| 2014/0170679 A1 | 6/2014 | Aitchison et al. | |
| 2014/0206412 A1 | 7/2014 | Dejohn et al. | |
| 2014/0296089 A1 | 10/2014 | Holmes et al. | |
| 2014/0367260 A1 | 12/2014 | Dickerson et al. | |
| 2015/0004077 A1 | 1/2015 | Wikswo et al. | |
| 2015/0037786 A1 | 2/2015 | Salsman | |
| 2015/0083595 A1 | 3/2015 | Krishnan et al. | |
| 2015/0136604 A1 | 5/2015 | Nielsen et al. | |
| 2015/0197784 A1 | 7/2015 | Williams et al. | |
| 2015/0219618 A1 | 8/2015 | Krishnan et al. | |
| 2015/0266022 A1 | 9/2015 | Eltoukhy et al. | |
| 2015/0283553 A1 | 10/2015 | Charlot et al. | |
| 2015/0301031 A1 | 10/2015 | Zin et al. | |
| 2016/0011115 A1 | 1/2016 | Chen et al. | |
| 2016/0175840 A1 | 6/2016 | Ingber et al. | |
| 2016/0232562 A1 | 8/2016 | Esayian et al. | |
| 2016/0256870 A1* | 9/2016 | Ismagilov | B01L 3/502715 |
| 2016/0271622 A1* | 9/2016 | Charlot | B03C 5/026 |
| 2016/0327549 A1 | 11/2016 | Charlot et al. | |
| 2017/0039344 A1 | 2/2017 | Bitran et al. | |
| 2017/0072395 A1* | 3/2017 | Krishnan | B01D 57/02 |
| 2017/0146509 A1 | 5/2017 | Yu et al. | |
| 2017/0161452 A1 | 6/2017 | Bain | |

(56) References Cited

U.S. PATENT DOCUMENTS

| | | |
|---|---|---|
| 2017/0184545 A1 | 6/2017 | Azpiroz et al. |
| 2017/0189904 A1 | 7/2017 | Aravanis et al. |
| 2017/0220736 A1 | 8/2017 | Lo et al. |
| 2017/0229149 A1 | 8/2017 | Rothschild et al. |
| 2017/0292064 A1 | 10/2017 | Monroe et al. |
| 2017/0370836 A1 | 12/2017 | Gerion et al. |
| 2018/0052093 A1 | 2/2018 | Shi et al. |
| 2018/0274014 A1 | 9/2018 | Krishnan et al. |
| 2018/0345284 A1 | 12/2018 | Charlot et al. |
| 2019/0017107 A1 | 1/2019 | Light et al. |
| 2019/0210023 A1 | 7/2019 | Turner et al. |
| 2021/0020275 A1 | 1/2021 | Krishnan et al. |
| 2021/0146378 A1 | 5/2021 | Hinestrosa Salazar et al. |
| 2021/0214798 A1 | 7/2021 | Krishnan et al. |
| 2022/0228193 A1* | 7/2022 | Jones ................ A61K 47/6843 |

FOREIGN PATENT DOCUMENTS

| | | | | |
|---|---|---|---|---|
| CN | 1348100 A | 5/2002 | | |
| CN | 101208593 A | 6/2008 | | |
| CN | 100417936 C | * 9/2008 | | |
| CN | 102037351 A | 4/2011 | | |
| CN | 102320559 A | 1/2012 | | |
| EP | 1775589 A1 | 4/2007 | | |
| GB | 2516666 A | 2/2015 | | |
| JP | H0663360 A | 3/1994 | | |
| JP | H11514087 A | 11/1999 | | |
| JP | 2001500252 A | 1/2001 | | |
| JP | 2002502047 A | 1/2002 | | |
| JP | 2004532968 A | 10/2004 | | |
| JP | 2005501251 A | 1/2005 | | |
| JP | 2006135191 A | 5/2006 | | |
| JP | 2008298575 A | 12/2008 | | |
| JP | 2011516867 A | 5/2011 | | |
| JP | 2011522219 A | 7/2011 | | |
| JP | 2013232627 A | 11/2013 | | |
| JP | 2014521954 A | 8/2014 | | |
| JP | 2017512483 A | 5/2017 | | |
| TW | 201726540 A | 8/2017 | | |
| WO | WO-9804355 A1 | 2/1998 | | |
| WO | WO-9938612 A1 | 8/1999 | | |
| WO | WO-0196025 A2 | 12/2001 | | |
| WO | WO-2005012872 A2 | 2/2005 | | |
| WO | WO-2005031300 A2 | * 4/2005 | ............ | B03C 5/026 |
| WO | WO-2005121767 A1 | 12/2005 | | |
| WO | WO-2006018981 A1 | 2/2006 | | |
| WO | WO-2006120656 A1 | 11/2006 | | |
| WO | WO-2007106552 A2 | 9/2007 | | |
| WO | WO-2007107910 A1 | 9/2007 | | |
| WO | WO-2009146143 A2 | 12/2009 | | |
| WO | WO-2012028746 A1 | 3/2012 | | |
| WO | WO-2013060762 A1 | 5/2013 | | |
| WO | WO-2013112425 A1 | 8/2013 | | |
| WO | WO-2013158686 A1 | 10/2013 | | |
| WO | WO-2014011740 A1 | 1/2014 | | |
| WO | WO-2014015187 A1 | 1/2014 | | |
| WO | WO-2014028222 A1 | 2/2014 | | |
| WO | WO-2014207731 A1 | 12/2014 | | |
| WO | WO-2015038797 A1 | 3/2015 | | |
| WO | WO-2015097858 A1 | 7/2015 | | |
| WO | WO-2015148808 A1 | 10/2015 | | |
| WO | WO-2015157217 A1 | 10/2015 | | |
| WO | WO-2015196141 A1 | 12/2015 | | |
| WO | WO-2016025698 A1 | 2/2016 | | |
| WO | WO-2016179308 A1 | 11/2016 | | |
| WO | WO-2017125475 A1 | 7/2017 | | |
| WO | WO-2017165852 A1 | 9/2017 | | |
| WO | WO-2017181030 A2 | * 10/2017 | ............ | B01D 61/00 |
| WO | WO-2018208820 A1 | 11/2018 | | |
| WO | WO-2019126388 A1 | * 6/2019 | ........ | B01L 3/502761 |
| WO | WO-2019126391 A1 | 6/2019 | | |
| WO | WO-2019195196 A1 | 10/2019 | | |
| WO | WO-2019200323 A1 | 10/2019 | | |
| WO | WO-2022011313 A1 | 1/2022 | | |
| WO | WO-2022155223 A1 | 7/2022 | | |

OTHER PUBLICATIONS

Asbury et al. Trapping of DNA by dielectrophoresis. Electrophoresis 23:2658-2666 (2002).

Asbury et al. Trapping of DNA in Nonuniform Oscillating Electric Fields. Biophys J. 74:1024-1030 (1998).

Becker et al. Separation of Human Breast Cancer Cells From Blood by Differential Dielectric Affinity. Proceedings of the National Academy of Sciences 92:860-864 (1995).

Becker et al. The removal of human leukemia cells from blood using interdigitated microelectrodes. J Phys. D: Appl. Phys. 27:2659-2662 (1994).

Bettegowda et al. Detection of Circulating Tumor DNA in Early- and Late-Stage Human Malignancies. Sci Transl Med. 6:224 (2014).

Board et al. DNA Methylation in Circulating Tumour DNA as a Biomarker for Cancer. Biomark Insights 2:307-319 (2007).

Board et al. Isolation and extraction of circulating tumor DNA from patients with small cell lung cancer. Ann. N. Y. Acad. Sci. 1137:98-107 (Aug. 2008).

Cairns. Detection of promoter hypermethylation of tumor suppressor genes in urine from kidney cancer patients. Ann N Y Acad Sci. 1022:40-43 (Jun. 2004).

Casciano et al. Circulating Tumor Nucleic Acids: Perspective in Breast Cancer. Breast Care 5:75-80 (2010).

Catarino et al. Quantification of Free circulating tumor DNA as a diagnostic marker for breast cancer. DNA Cell Biol. 27(8):415-421 (Aug. 2008).

Cetin et al. Microfluidic bio-particle manipulation for biotechnology. Biochemical Engineering Journal 92:63-82 (2014).

Chan. Circulating EBV DNA as a tumor marker for nasopharyngeal carcinoma. Semin Cancer Biol. 12(6):489-496 (Dec. 2002).

Chan et al. Nasopharyngeal carcinoma. Annals of Oncology 13:1007-1015 (2002).

Chan et al. Persistent Aberrations in Circulating DNA Integrity after Radiotherapy Are Associated with Poor Prognosis in Nasopharyngeal Carcinoma Patients. Clinical Cancer Research 14(13):4141-4145 (2008).

Chan et al. Quantitative Analysis of Circulating Methylated DNA as a Biomarker for Hepatocellular Carcinoma. Clinical Chemistry 54(9):1528-1536 (2008).

Chan et al. Radiological, pathological and DNA remission in recurrent metastatic nasopharyngeal carcinoma. BMC Cancer 6:259 (Oct. 31, 2006).

Cheng et al. Isolation of Cultured Cervical Carcinoma Cells Mixed with Peripheral Blood Cells on a Bioelectronic Chip. Analytical Chemistry 70(11):2321-2326 (1998).

Cheng et al. Preparation and Hybridization Analysis of DNA/A from E. coli on Microfabricated Bioelectronic Chips. Nature Biotechnology 16:541-546 (1998).

Cheng et al. Quantification of circulating cell-free DNA in the plasma of cancer patients during radiation therapy. Cancer Science 100(2):303-309 (Feb. 2009).

Choi et al. Microfluidic-based biosensors toward point-of-care detection of nucleic acids and proteins. Microfluidics And Nanofluidics 10(2):231-247 (2010).

Chuang et al. Detectable BRAF mutation n serum DNA samples from patients with papillary thyroid carcinomas. Head Neck 32(2):229-234 (2010).

Chun et al. Circulating tumour-associated plasma DNA represents an independent and informative predictor of prostate cancer. BJU International 98(3):544-548 (2006).

Combaret et al. Circulating MYCN DNA as a Tumor-specific Marker in Neuroblastoma Patients. Cancer Research 62:3646-3648 (Jul. 1, 2002).

Cortese et al. Epigenetic markers of prostate cancer in plasma circulating DNA. Human Molecular Genetics 21:3619-3631 (2012).

Da Silva et al. Circulating cell-free DNA in serum as a biomarker of colorectal cancer. Journal of Clinical Pathology 66(9):775-778 (Sep. 2013).

Daniotti et al. Detection of mutated BRAFV600E variant in circulating DNA of stage III-IV melanoma patients. Int. J. Cancer 120:2439-2444 (Jun. 1, 2007).

(56) References Cited

OTHER PUBLICATIONS

Dawson et al. Analysis of circulating tumor DNA to monitor metastatic breast cancer. N Engl J Med 368:1199-1209 (2013).
De Maio et al. Circulating and stool nucleic acid analysis for colorectal cancer diagnosis. World Journal of Gastroenterology 20(4):957-967 (Jan. 28, 2014).
Delgado. Characterization of cell-free circulating DNA in plasma in patients with prostate cancer. Tumor Biol. 34(2):983-986 (Apr. 2013).
Deligezer et al. Effect of adjuvant chemotherapy on integrity of free serum DNA in patients with breast cancer. Ann N Y Acad Sci. 1137:175-179 (Aug. 2008).
Devos et al. Circulating Methylated Sep. 9 DNA in Plasma Is a Biomarker for Colorectal Cancer. Clinical Chemistry 55(7):1337-1346 (Jul. 2009).
Dobrzycka. Circulating free DNA and p53 antibodies in plasma of patients with ovarian epithelial cancers. Annals of Oncology 22(5):1133-1140 (May 2011).
Dobrzycka. Circulating free DNA, p53 antibody and mutations of KRAS gene in endometrial cancer. 127(3):612-621 (Aug. 1, 2010).
El Tarhouny et al. Comparison of serum VEGF and its soluble receptor sVEGFR1 with serum cell-free DNA in patients with breast tumor. Cytokine 44(1):65-69 (Oct. 2008).
Ellinger et al. Cell-free circulating DNA: diagnostic value in patients with testicular germ cell cancer. J. Urol. 181(1):363-371 (Jan. 2009).
Ellinger et al. CpG island hypermethylation of cell-free circulating serum DNA in patients with testicular cancer. J. Urol. 182(1):324-329 (Jul. 2009).
Ellinger et al. Noncancerous PTGS2 DNA fragments of apoptotic origin in sera of prostate cancer patients qualify as diagnostic and prognostic indicators. Int. J. Cancer 122(1):138-143 (Jan. 1, 2008).
Elshimali et al. The Clinical Utilization of Circulating Cell Free DNA (CCFDNA) in Blood of Cancer Patients. Int. J. Mol. Sci. 14(9):18925-18958 (Sep. 13, 2013).
Fuhr et al. Cell manipulation and cultivation under a.c. electric field influence in highly conductive culture media. Biochimica et Biophysica Acta 1201:353-360 (1994).
Gahan et al. Circulating nucleic acids in plasma and serum: diagnosis and prognosis in cancer. EPMA Journal 1(3):503-512 (Sep. 2010).
Ganepola et al. Use of blood-based biomarkers for early diagnosis and surveillance of colorectal cancer. World Journal of Gastrointestinal Oncology 6(4):83-97 (Apr. 15, 2014).
Gautschi et al. Circulating deoxyribonucleic Acid as prognostic marker in non-small-cell lung cancer patients undergoing chemotherapy. J Clin Oncol. 22(20):4157-4164 (2004).
Goessl et al. DNA Alterations in Body Fluids as Molecular Tumor Markers for Urological Malignancies. European Urology 41(6):668-676 (Jun. 2002).
Goodard et al. Handbook of Nanoscience. 2nd edition. Ch 16, p. 5-8 (2007).
Gornik et al. Free serum DNA is an early predictor of severity of acute pancreatitis. Clin Biochem. 42(1-2):38-43 (Jan. 2009).
Green et al. Ac electrokinetics: a survey of sub-micrometre particle dynamics. J. Phys. D: Appl. Phys. 33:632-641 (2000).
Guan et al. Analysis of circulating DNA level in the plasma of cervical cancer patients. Nan fang Yi Ke Da Xue Xue Bao 28(9):1663-1667 (Aug. 2008) (English Abstract).
Haeberle et al. Centrifugal extraction of plasma from whole blood on a rotating disk. Lab Chip 6(6):776-781 (2006).
Hashad et al. Free circulating tumor DNA as a diagnostic marker for breast cancer. J Clin Lab Anal. 26(6):467-472 (Nov. 2012).
Higgins et al. Variant Ciz1 is a circulating biomarker for early-stage lung cancer. PNAS USA 109(45):E3128-3135 (Nov. 6, 2012).
Higuchi. Chromosomal DNA fragmentation in apoptosis and necrosis induced by oxidative stress. Biochem Pharacol. 66:1527-1535(2003).

Higuchi et al. Appearance of 1-2 Mbp giant DNA fragments as an early common response leading to cell death induced by various substances that cause oxidative stress. Free Radical Biology & Medicine 23:90-99 (1997).
Hoffmann et al. Methylated DAPK and APC promoter DNA detection in peripheral blood is significantly associated with apparent residual tumor and outcome. J Cancer Res Clin Oncol. 135(89):1231-1237 (Sep. 2009).
Hoffmann et al. Universal protocol for grafting PCR primers onto various lab-on-a-chip substrates for solid-phase PCR. RSC Advances 2:3885-3889 (2012).
Hohaus et al. Cell-free circulating DNA in Hodgkin's and non-Hodgkin's lymphomas. Annals of Oncology 20(8):1408-1413 (2009).
Holdhoff et al. Blood-based biomarkers for malignant gliomas. J Neurooncol 113:345-352 (2013).
Holzel et al. Trapping Single Molecules by Dielectrophoresis. Phys. Rev. Left. 95:128102 (2005).
Hosny et al. Ser-249 TP53 and CTNNB1 mutations in circulating free DNA of Egyptian patients with hepatocellular carcinoma versus chronic liver diseases. Cancer Lett. 264(2):201-208 (Jun. 18, 2008).
Huang et al. Dielectrophoretic Cell Separation and Gene Expression Profiling on Microelectronic Chip Arrays. Analytical Chem. 74:3362-3371 (2002).
Huang et al. Electric Manipulation of Bioparticles and Macromolecules on Microfabricated Electrodes. Analytical Chemistry (73):1549-1559 (2001).
Huang et al. Functionalization of Surfaces by Water-Accelerated Atom-Transfer Radical Polymerization of Hydroxyethyl Methacrylate and Subsequent Derivatization. Macromolecules 35:1175-1179 (2002).
Hughes. Chapter 16: Nanoparticle Manipulation by Electrostatic Forces. Handbook of Nanoscience, Engineering and Technology 2nd Ed., WA Goddard III, DW Brenner, S. Lyshenski & G. Iafrate (eds.) (CRC Press 2007), pp. 16-1 to 16-32.
Hughes et al. Dielectrophoretic Characterization and Separation of Antibody-Coated Submicrometer Latex Spheres. Anal Chem 71:3441-3445 (1999).
Hughes et al. Dielectrophoretic Manipulation and Characterization of Herpes Simplex Virus-1 Capsids. Eur Biophys J 30:268-272 (2001).
Hughes. Strategies for Dielectrophoretic Separation in Laboratory-on-a-chip Systems. Electrophoresis 23:2569-2582 (2002).
Iida et al. Relation between serum levels of cell-free DNA and inflammation status in hepatitis C virus-related hepatocellular carcinoma. Oncology Reports 20(4):761-765 (Oct. 2008).
Iizuka et al. Elevated Levels of Circulating Cell-free DNA in the Blood of Patients with Hepatitis C Virus-associated Hepatocellular Carcinoma. Anticancer Research 26(6C):4713-4720 (2006).
Jiang et al. Dynamic monitoring of plasma circulating DNA in patients with acute myeloid leukemia and its clinical significance. Zhongguo Shi Yan Xue Ye Xue Za Zhi 20(1):53-56 (Feb. 2012) (Abstract).
Jiang et al. Increased plasma DNA integrity index in head and neck cancer patients. Int. J. Cancer 119(11):2673-2676 (Dec. 2006).
Jin et al. Circulating DNA—Important Biomarker of Cancer. Journal of Molecular Biomarkers & Diagnosis S2 (2012) (7 pgs.).
Kakimoto et al. Microsatellite analysis of serum DNA in patients with oral squamous cell carcinoma. Oncology Reports 20(5):1195-1200 (Nov. 2008).
Kolesnikova et al. Circulating DNA in the blood of gastric cancer patients. Ann N Y Acad Sci. 1137:226-231 (Aug. 2008).
Krishnan et al. Alternating current electrokinetic separation and detection of DNA nanoparticles in high-conductance solutions. Electrophoresis 29(9):1765-1774 (2008).
Krishnan et al. An AC electrokinetic method for enhanced detection of DNA nanoparticles. J. Biophotonics 2(4):253-261 (2009).
Krishnan et al. Interaction of nanoparticles at the DEP microelectrode interface under high conductance conditions. Electrochem. Comm. 11(8):1661-1666 (2009).
Kuhlmann et al. LOH at 6q and 10q in fractionated circulating DNA of ovarian cancer patients is predictive for tumor cell spread and overall survival. BMC Cancer 12:3525 (Jul. 31, 2012).

(56) References Cited

OTHER PUBLICATIONS

Lavon et al. Serum DNA can define tumor-specific genetic and epigenetic markers in gliomas of various grades. Neuro-Oncology 12(2):173-180 (2010).
Lee et al. A micro cell lysis device. Sensors and Actuators A: Physical. 73(1-2):74-79 (1999).
Lee et al. Methylation of TMEFF2 Gene in Tissue and Serum DNA from Patients with Non-Small Cell Lung Cancer. Molecules and Cells 34(2):171-176 (Aug. 31, 2012).
Li et al. Alternating current electrokinetics enhanced in situ capacitive immunoassay. Electrophoresis 36(3):471-474 (2015).
Liggett et al. Differential Methylation of Cell-Free Circulating DNA Among Patients With Pancreatic Cancer Versus Chronic Pancreatitis. Cancer 116(7):1674-1680 (Apr. 1, 2010).
Liggett et al. Methylation patterns in cell-free plasma DNA reflect removal of the primary tumor and drug treatment of breast cancer patients. Int. J. Cancer 128(2):492-499 (Jan. 15, 2011).
Lo Nigro et al. Methylated Tissue Factor Pathway Inhibitor 2 (TFPI2) DNA in Serum Is a Biomarker of Metastatic Melanoma. Journal of Investigative Dermatology 133(5):1278-1285 (May 2013).
Lofton-Day et al. DNA Methylation Biomarkers for Blood-Based Colorectal Cancer Screening. Clinical Chemistry 54(2):414-423 (Feb. 2008).
Ma et al. Detection of circulating hypermethylated tumor-specific RASSF1A DNA in ovarian cancer patients. Zhonghua Bing Li Xue Za Zhi. 34(12):785-787 (Dec. 2005) (Abstract).
Ma et al. Methylated DNA and microRNA in Body Fluids as Biomarkers for Cancer Detection. International Journal of Molecular Sciences 14(5):10307-10331 (May 16, 2013).
Majchrzak et al. Detection of MGMT, RASSF1A, p15INK4B, and p14ARF promoter methylation in circulating tumor-derived DNA of central nervous system cancer patients. J. Appl. Genetics 54:335-344 (2013).
Melnikov et al. Methylation profile of circulating plasma DNA in patients with pancreatic cancer. J Surg Oncol. 99(2):119-122 (Feb. 2009).
Menachery et al. Controlling cell destruction using dielectrophoretic forces. IEE Proc.—Nanobiotechnol. 152(4):145-149 (2005).
Mirza et al. Clinical significance of promoter hypermethylation of ERβ and RARβ2 in tumor and serum DNA in Indian breast cancer patients. Ann Surg Oncol. 19(9):3107-3115 (Sep. 2012).
Misale et al. Emergence of KRAS mutations and acquired resistance to anti EGFR therapy in colorectal cancer. Nature 486(7404):532-536 (Jun. 28, 2012).
Misawa et al. RASSF1A hypermethylation in pretreatment serum DNA of neuroblastoma patients: a prognostic marker. British Journal of Cancer 100:399-404 (2009).
Morgan et al. Separation of Submicron Bioparticles by Dielectrophoresis Biophysical Journal. 77:516-525 (1999).
Mouliere et al. Circulating Cell-Free DNA from Colorectal Cancer Patients May Reveal High KRAS or BRAF Mutation Load. Translational Oncology 6(3):319-328 (Jun. 2013).
Muller et al. DNA Methylation in Serum of Breast Cancer Patients: An Independent Prognostic Marker. Cancer Research 63(22):7641-7645 (Nov. 15, 2003).
Muller et al. Identification of Loss of Heterozygosity on Circulating Free DNA in Peripheral Blood of Prostate Cancer Patients: Potential and Technical Improvements. Clinical Chemistry 54(4):688-696 (Apr. 2008).
Nakagawa et al. Fabrication of amino Silane-Coated Microchip for DNA extraction from Whole Blood. Journal of Biotechnology 116(2):105-111 (2005).
Nakamoto et al. Detection of Microsatellite Alterations in Plasma DNA of Malignant Mucosal Melanoma Using Whole Genome Amplification. Bull Tokyo Dent. Coll. 49(2):77-87 (May 2008).
Nakamura et al. Application of a Highly Sensitive Detection System for Epidermal Growth Factor Receptor Mutations in Plasma DNA. Journal of Thoracic Oncology 7(9):1369-1381 (Sep. 2012).
Nakayama et al. A Highly Sensitive Method for the Detection of p16 Methylation in the Serum of Colorectal Cancer Patients. Anticancer Research 27(3B):1459-1464 (2007).
Page et al. Detection of HER2 amplification in circulating free DNA in patients with breast cancer. British Journal of Cancer 104:1342-1348 (2011).
Pang et al. Microsatellite alterations of circulating DNA in the plasma of patients with hepatocellular carcinoma. Zhonghua Yi Xue Za Zhi. 86(24):1662-1665 (Jun. 27, 2006) (Abstract).
Papadopoulou et al. Cell-free DNA and RNA in Plasma as a New Molecular Marker for Prostate and Breast Cancer, Ann. NY, Acad. Sci. 1075:235-243 (2006).
Parker et al. mRNA: detection by In Situ and northern hybridization. Methods Mol Biol 106:247-283 (1999).
PCT/US2009/039565 International Preliminary Report on Patentability and Written Opinion dated Oct. 5, 2010.
PCT/US2009/039565 International Search Report dated Dec. 23, 2009.
PCT/US2013/036845 International Search Report and Written Opinion dated Aug. 6, 2013.
PCT/US2013/051158 International Search Report and Written Opinion dated Nov. 14, 2013.
PCT/US2015/024624 International Search Report and Written Opinion dated Aug. 21, 2015.
PCT/US2015/036789 International Search Report and Written Opinion dated Sep. 29, 2015.
PCT/US2016/030821 International Search Report and Written Opinion dated Aug. 29, 2016.
PCT/US2017/024149 International Search Report and Written Opinion dated Jul. 18, 2017.
PCT/US2017/024149 Invitation to Pay Additional Fees dated May 15, 2017.
PCT/US2018/031652 International Search Report and Written Opinion dated Jul. 31, 2018.
PCT/US2018/066602 International Search Report and Written Opinion dated Apr. 4, 2019.
PCT/US2018/066605 International Search Report and Written Opinion dated Mar. 25, 2019.
PCT/US2019/025242 International Search Report and Written Opinion dated Jun. 11, 2019.
Persat, et al., Purification of Nucleic Acids from Whole Blood Using Isotachophoresis, Analytical Chemistry, 81.22 (Nov. 15, 2009): 9507-9511, supporting materials.
Pethig. Dielectrophoresis: Using Inhomogenous AC Electrical Fields to Separate and Manipulate Cells, CRC Critical Reviews in Biotechnology, CRC Press, Boca Raton, FL, US. 16(4):331-348 (Jan. 1, 1996).
Ponomaryova et al. Potentialities of aberrantly methylated circulating DNA for diagnostics and post-treatment follow-up of lung cancer patients. Lung Cancer. 81(3):397-403 (Sep. 2013).
Ramos et al. Ac electrokinetics: a review offerees in microelectrode structures. J Phys. D: Appl. Phys. 31:2338-2353 (1998).
Ren et al. Circulating DNA level is negatively associated with the long-term survival of hepatocellular carcinoma patients. World Journal of Gastroenterology 12(24):3911-3914 (Jun. 28, 2006).
Sai et al. Quantification of Plasma Cell-free DNA in Patients with Gastric Cancer. Anticancer Research 27(4C):2747-2752 (2007).
Sakakura et al. Quantitative Analysis of Tumor-derived Methylated RUNX3 Sequences in the Serum of Gastric Cancer Patients. Anticancer Research 29:2619-2626 (2009).
Salkeni et al. Detection of EGFRvIII mutant DNA in the peripheral blood of brain tumor patients. J. Neurooncol. 115(1):27-35 (Oct. 2013).
Sawabu et al. Serum tumor markers and molecular biological diagnosis in pancreatic cancer. Pancreas 28(3):263-267 (Apr. 2004).
Schwarzenbach. Detection and monitoring of cell-free DNA in blood of patients with colorectal cancer. Ann N Y Acad Sci. 1137:190-196 (Aug. 2008).
Schwarzenbach. Loss of Heterozygosity at Tumor Suppressor Genes Detectable on Fractionated Circulating Cell-Free Tumor DNA as Indicator of Breast Cancer Progression. Clinical Cancer Research 18:5719-5730 (Sep. 25, 2012).

(56) References Cited

OTHER PUBLICATIONS

Sharma et al. DNA methylation of circulating DNA: a marker for monitoring efficacy of neoadjuvant chemotherapy in breast cancer patients. Tumour Biol. 33(6):1837-1843 (Dec. 2012).
Shaw et al. Genomic analysis of circulating cell-free DNA infers breast cancer dormancy. Genome Research 22(2):220-231 (Feb. 2012).
Sonnenberg et al. Dielectrophoretic isolation and detection of cfc-DNA nanoparticulate biomarkers and virus from blood. Electrophoresis 34(7):1076-1084 (2013).
Sonnenberg et al. Dielectrophoretic Isolation of DNA and Nanoparticles from Blood. Electrophoresis 33(16):2482-2490 (2012).
Sorenson. Detection of Mutated KRAS2 Sequences as Tumor Markers in Plasma/Serum of Patients with Gastrointestinal Cancer. Clin Cancer Res 6:2129-2137 (2000).
Sosnowski et al. Rapid determination of single base mismatch mutations in DNA hybrids by direct electric field control. PNAS USA 94:1119-1123 (Feb. 1997).
Stephens et al. The dielectrophoresis enrichment of CD34+ cells from peripheral blood stern cell harvests. Bone Marrow Transplant. 18:777-782 (1996).
Stroun et al. Isolation and characterization of DNA from the plasma of cancer patients. Eur J Cancer Clin Oncol 23:707-712 (1987).
Swaminathan et al. Enhanced sub-micron colloidal particle separation with interdigitated microelectrode arrays using mixed AC/DC dielectrophoretic scheme. Biomedical Microdevices 17(2):1-9(2015).
Swanson. A fully multiplexed CMOS biochip for DNA analysis. Sensors and Actuators B 64:22-30 (Jun. 2000).
Tamkovich et al. Cell-surface-bound circulating DNA as a prognostic factor in lung cancer. Ann N Y Acad Sci. 1137:214-217 (Aug. 2008).
Tanaka et al. Role of circulating free alu DNA in endometrial cancer. Int J Gynecol Cancer 22(1):82-86 (Jan. 2012).
Tangkijvanich et al. Serum LINE-1 hypomethylation as a potential prognostic marker for hepatocellular carcinoma. Clin Chim Acta. 379(1-2):127-133 (Apr. 2007).
Tani et al. An early detection of recurrence using reverse transcriptase-polymerase chain reaction (RT-PCP) and methylation-specific polymerase chain reaction (MSP) from peripheral blood in patients after gastrectomy. Gan to Kagaku Ryoho 33(12):1720-1722 (Nov. 2006) (Abstract).
Tomita et al. Quantification of Circulating Plasma DNA Fragments as Tumor Markers in Patients with Esophageal Cancer, Anticancer Research 27(4C):2737-2742 (2007).
Toner et al. Blood-on-a-chip. Annual Review of Biomedical Engineering 7:77-103 (2005).
Tong et al. Diagnostic developments involving cell-free (circulating) nucleic acids. Clinica Chimica Acta. 363:187-96 (2006).
Toth et al. Free circulating DNA based colorectal cancer screening from peripheral blood: the possibility of the methylated septin 9 gene marker. Orv. Hetil. 150(21):969-977(May 24, 2009) (English Abstract).
Trevisiol et al. Prognostic value of circulating KRAS2 gene mutations in colorectal cancer with distant metastases. Int J Biol Markers. 21(4):223-228 (Oct.-Dec. 2006).
Tuukanen et al. Carbon nanotubes as electrodes for dielectrophoresis of DNA. Nano Letters. 6:1339-1343 (2006).
Umetani et al. Increased Integrity of Free Circulating DNA in Sera of Patients with Colorectal or Periampullary Cancer: Direct Quantitative PCR for ALU Repeats. Clinical Chemistry 52(6):1062-1069 (Jun. 2006).
Umetani et al. Prediction of Breast Tumor Progression by Integrity of Free Circulating DNA in Serum. Journal of Clinical Oncology 24(26):4270-4276 (Sep. 10, 2006).
U.S. Appl. No. 12/936,147 Office Action dated Apr. 27, 2015.
U.S. Appl. No. 12/936,147 Office Action dated Aug. 12, 2015.
U.S. Appl. No. 12/936,147 Office Action dated Dec. 11, 2012.
U.S. Appl. No. 12/936,147 Office Action dated Jul. 18, 2013.
U.S. Appl. No. 12/936,147 Office Action dated Mar. 17, 2017.
U.S. Appl. No. 12/936,147 Office Action dated Oct. 31, 2012.
U.S. Appl. No. 12/936,147 Office Action dated Sep. 22, 2016.
U.S. Appl. No. 13/864,179 Office Action dated Aug. 15, 2013.
U.S. Appl. No. 14/063,884 Office Action dated Aug. 28, 2014.
U.S. Appl. No. 14/063,884 Office Action dated Feb. 12, 2014.
U.S. Appl. No. 14/067,841 Office Action dated Mar. 16, 2015.
U.S. Appl. No. 14/194,566 Office Action dated May 15, 2014.
U.S. Appl. No. 14/201,715 Office Action dated May 15, 2014.
U.S. Appl. No. 14/201,726 Office Action dated May 16, 2014.
U.S. Appl. No. 14/271,337 Office Action dated Jun. 12, 2014.
U.S. Appl. No. 14/311,037 Office Action dated Sep. 5, 2014.
U.S. Appl. No. 14/415,546 Office Action dated Apr. 28, 2016.
U.S. Appl. No. 14/415,546 Office Action dated Oct. 7, 2016.
U.S. Appl. No. 14/477,800 Office Action dated Dec. 15, 2014.
U.S. Appl. No. 14/477,800 Office Action dated Feb. 2, 2015.
U.S. Appl. No. 14/509,022 Office Action dated Jan. 15, 2015.
U.S. Appl. No. 14/512,356 Office Action dated Feb. 5, 2015.
U.S. Appl. No. 14/680,819 Office Action dated Dec. 3, 2015.
U.S. Appl. No. 14/925,157 Office Action dated Mar. 22, 2016.
U.S. Appl. No. 15/146,572 Office Action dated Jul. 11, 2019.
U.S. Appl. No. 15/171,876 Office Action dated Oct. 12, 2016.
U.S. Appl. No. 15/293,062 Office Action dated Mar. 22, 2017.
U.S. Appl. No. 15/320,730 Office Action dated Oct. 4, 2017.
U.S. Appl. No. 15/571,812 Office Action dated Apr. 30, 2020.
U.S. Appl. No. 15/571,812 Office Action dated Oct. 21, 2019.
U.S. Appl. No. 15/974,591 Office Action dated Jan. 2, 2020.
U.S. Appl. No. 15/974,591 Office Action dated Mar. 21, 2019.
U.S. Appl. No. 15/974,591 Office Action dated Sep. 5, 2018.
U.S. Appl. No. 15/991,717 Office Action dated Jul. 9, 2019.
U.S. Appl. No. 15/991,717 Office Action dated Nov. 2, 2018.
U.S. Appl. No. 16/355,462 Office Action dated Sep. 3, 2020.
U.S. Appl. No. 15/146,572 Office Action dated Jan. 2, 2019.
U.S. Appl. No. 15/469,406 Office Action dated Mar. 28, 2018.
Wallner et al. Methylation of Serum DNA Is an Independent Prognostic Marker in Colorectal Cancer. Clinical Cancer Research 12(24):7347-7352 (Dec. 15, 2006).
Ward et al. Binding activities of a repertoire of single immunoglobulin variable domains secreted from *Escherichia coli*. Nature 341(6242):544-546 (1989).
Washizu et al. Applications of electrostatic stretch-and-positioning of DNA. Industry Applications. IEEE Transactions on Industry Applications 31:447-456 (1995).
Washizu et al. Electrostatic manipulation of DNA in microfabricated structures. Industry Applications. IEEE Transactions on Industry Applications 26:1165-1172 (1990).
Weaver et al. Methylated tumor-specific DNA as a plasma biomarker in patients with glioma. Cancer Invest. 24(1):35-40 (Feb. 2006).
Weiss et al. Circulating tumor DNA to monitor metastatic breast cancer. New England Journal of Medicine. 369(1):93 (Jul. 4, 2013).
Widschwendter et al. CDH1 and CDH13 Methylation in Serum is an Independent Prognostic Marker in Cervical Cancer Patients. Int. J. Cancer 109(2):163-166 (Mar. 20, 2004).
Wu et al. Cell-free DNA: measurement in various carcinomas and establishment of normal reference range. Clin Chim Acta. 321(1-2):77-87 (2002).
Xie et al. Quantification of plasma DNA as a screening tool for lung cancer. Chinese Medical Journal 117(10):1485-1488 (Oct. 2004).
Yoon et al. Comparison of Circulating Plasma DNA Levels between Lung Cancer Patients and Healthy Controls. Journal of Molecular Diagnostics 11(3):182-185 (May 2009).
Zachariah et al. Circulating cell-free DNA as a potential biomarker for minimal and mild endometriosis. Reprod Biomed Online 18(3):407-411 (Mar. 2009).
Zachariah et al. Levels of circulating cell-free nuclear and mitochondrial DNA in benign and malignant ovarian tumors. Obstet. Gynecol. 112(4):843-850 (Oct. 2008).
Zhang et al. Individually addressable microelectrode arrays fabricated with gold-coated pencil graphite particles for multiplexed and high sensitive impedance immunoassays. Biosensors And Bioelectronics 25(1):34-40 (2009).
Zhou et al. Circulating cell-free nucleic acids: promising biomarkers of hepatocellular carcinoma. Semin Oncol. 39(4):440-448 (Aug. 2012).

(56) References Cited

OTHER PUBLICATIONS

Ziegler et al. Circulating DNA: a new diagnostic gold mine? Cancer Treat Rev. 28:255-271 (2002).
Zurita et al. Hypermethylated 14-3-3-σ and ESR1 gene promoters in serum as candidate biomarkers for the diagnosis and treatment efficacy of breast cancer metastasis. BMC Cancer 10(217) 9 pgs (May 2010).
Berg et al. Cellphone-Based Hand-Held Microplate Reader for Point-of-Care Testing of Enzyme-Linked Immunosorbent Assays. ACS NANO 9(8):7857-7866 (2015).
Quesada-Gonzalez et al. Mobile phone-based biosensing: An emerging "diagnostic and communication" technology. Biosensors And Bioelectronics 92:549-562 (2016).
U.S. Appl. No. 16/355,462 Office Action dated Jan. 21, 2021.
U.S. Appl. No. 17/045,146 Non-Final Office Action dated Mar. 6, 2023.
Cohen, et al., Detection and localization of surgically resectable cancers with a multi-analyte blood test. Science Feb. 23, 2018: vol. 359, Issue 6378, pp. 926-930. DOI: 10.1126/science.aar3247.
Dvorak: Vascular permeability factor/vascular endothelial growth factor: a critical cytokine in tumor angiogenesis and a potential target for diagnosis and therapy. J Clin Oncol. 20(21):4368-4380 doi:10.1200/JCO.2002.10.088 (2002).
Gao et al.: Increased integrity of circulating cell-free DNA in plasma of patients with acute leukemia. Clin Chem Lab Med. 48(11):1651-1656 doi:10.1515/CCLM.2010.311. (2010).
Hinestrosa et al.: Simultaneous Isolation of Circulating Nucleic Acids and EV-Associated Protein Biomarkers From Unprocessed Plasma Using an AC Electrokinetics-Based Platform. Front Bioeng Biotechnol. 8(581157):1-13 doi:10.3389/fbioe.2020.581157 (2020).
Hoshino et al.: Extracellular Vesicle and Particle Biomarkers Define Multiple Human Cancers. Cell 182(4):1044-1061.E18. doi:10.1016/j.cell.2020.07.009 (2020).
Hoshino et al.: Tumour exosome integrins determine organotropic metastasis. Nature 527(7578):329-335 doi:10.1038/nature15756 (2015).
JUPPNER. Functional properties of the PTH/PTHrP receptor. Bone. Aug. 1995; 17(2):Supplement 39S-42S.
Kjaergaard et al.: The use of the soluble adhesion molecules sE-selectin, sICAM-1, sVCAM-1, sPECAM-1 and their ligands CD11a and CD49d as diagnostic and prognostic biomarkers in septic and critically ill non-septic ICU patients. APMIS 124(10):846-855 doi:10.1111/apm.12585 (2016).
Krishnan et al.: Alternating current electrokinetic separation and detection of DNA nanoparticles in high-conductance solutions. Electrophoresis 29(9):1765-1774 doi:10.1002/elps.200800037 (2008).
Krishnan et al.: An AC electrokinetic method for enhanced detection of DNA nanoparticles. J Biophotonics. 2(4):253-261 doi:10.1002/jbio.200910007 (2009).
Krishnan et al.: Interaction of Nanoparticles at the DEP Microelectrode Interface under High Conductance Conditions, lectrochem commun. 11(8):1661-1666 doi:10.1016/j.elecom.2009.06.033 (2009).
Lennartsson et al.: Stem cell factor receptor/c-Kit: from basic science to clinical implications. Physiol Rev. 92(4):1619-1649 doi:10.1152/physrev.00046.2011 (2012).
Lida et al. Relation between serum levels of cell-free DNA and inflammation status in hepatitis C virus-related hepatocellular carcinoma. Oncol Rep. 20(4):761-5 (2008).
Liu et al. Sensitive and Specific Multi-Cancer Detection and Localization Using Methylation Signatures in Cell-Free DNA. Annals of Oncology 31(6):745-759 (2020).
Lu et al.: Abstract: AC electrokinetic isolation of cell free high molecular weight DNA (CF-HMW DNA) from serum. American Association for Cancer Research Publication 72(8):1704 URL: https://doi.org/10.1158/1538-7445.AM2012-1704 (2012).
Moasser: The oncogene HER2: its signaling and transforming functions and its role in human cancer pathogenesis. Oncogene 26(45):6469-6487 doi:10.1038/sj.onc.1210477 (2007).
Moreira, et al. Cell-free DNA as a noninvasive acute rejection marker in renal transplantation. Clin Chem. Nov. 2009;55(11):1958-66. doi: 10.1373/clinchem.2009.129072. Epub Sep. 3, 2009.
Mouliere et al. High fragmentation characterizes tumour-derived circulating DNA. PLoS ONE 6(9):e23418 (2011).
Niland et al.: Neuropilins in the Context of Tumor Vasculature. Int J Mol Sci. 20(3):639, pp. 1-44 doi:10.3390/ijms20030639 (2019).
PCT/US2021/041177 International Search Report and Written Opinion dated Oct. 19, 2021.
PCT/US2022/012149 International Search Report and Written Opinion dated Apr. 11, 2022.
Ross et al.: Binding affinity of surface functionalized gold nanoparticles to hydroxyapatite. J Biomed Mater Res A. 99(1):58-66 (2011).
Sonnenberg et al.: Dielectrophoretic isolation and detection of cancer-related circulating cell-free DNA biomarkers from blood and plasma. Electrophoresis. 2014 35(12-13):1828-1836 (2014).
Turner et al.: Cancer Detection at your Fingertips: Smartphone-Enabled DNA Testing. Annu Int Conf IEEE Eng Med Biol Soc. 2018:5418-5421 doi:10.1109/EMBC.2018.8513553 (2018).
U.S. Appl. No. 16/355,462 Final Office Action dated Mar. 8, 2022.
U.S. Appl. No. 16/955,732 Final Office Action dated Apr. 29, 2022.
U.S. Appl. No. 16/955,732 Non-Final Office Action dated Nov. 19, 2021.
U.S. Appl. No. 17/033,427 Non-Final Office Action dated Oct. 6, 2022.
U.S. Appl. No. 16/355,462 Office Action dated Aug. 18, 2021.
Xue et al. Optimizing the yield and utility of circulating cell-free DNA from plasma and serum. Clin Chim Acta 404(2):100-4 (2009).
OHWAKI: Characterization of native oxide on aluminum by infrared spectroscopy. 54(1):31-36. doi:10.2464/jilm.54.31 [with English Machine Translation] (2004).
U.S. Appl. No. 16/955,732 Non-Final Office Action dated Mar. 23, 2023.
U.S. Appl. No. 17/033,427 Final Office Action dated Apr. 21, 2023.

* cited by examiner cfDNA (green) and PD-L1 protein (red)

NSCLC, Adenocarcinoma, IV, M, 72
PS111

Ovarian, IIC, F, 72
BD2-18A

NSCLC, Squamous Cell, II, M, 61
PS125

Healthy Normal, F, 55
PS186

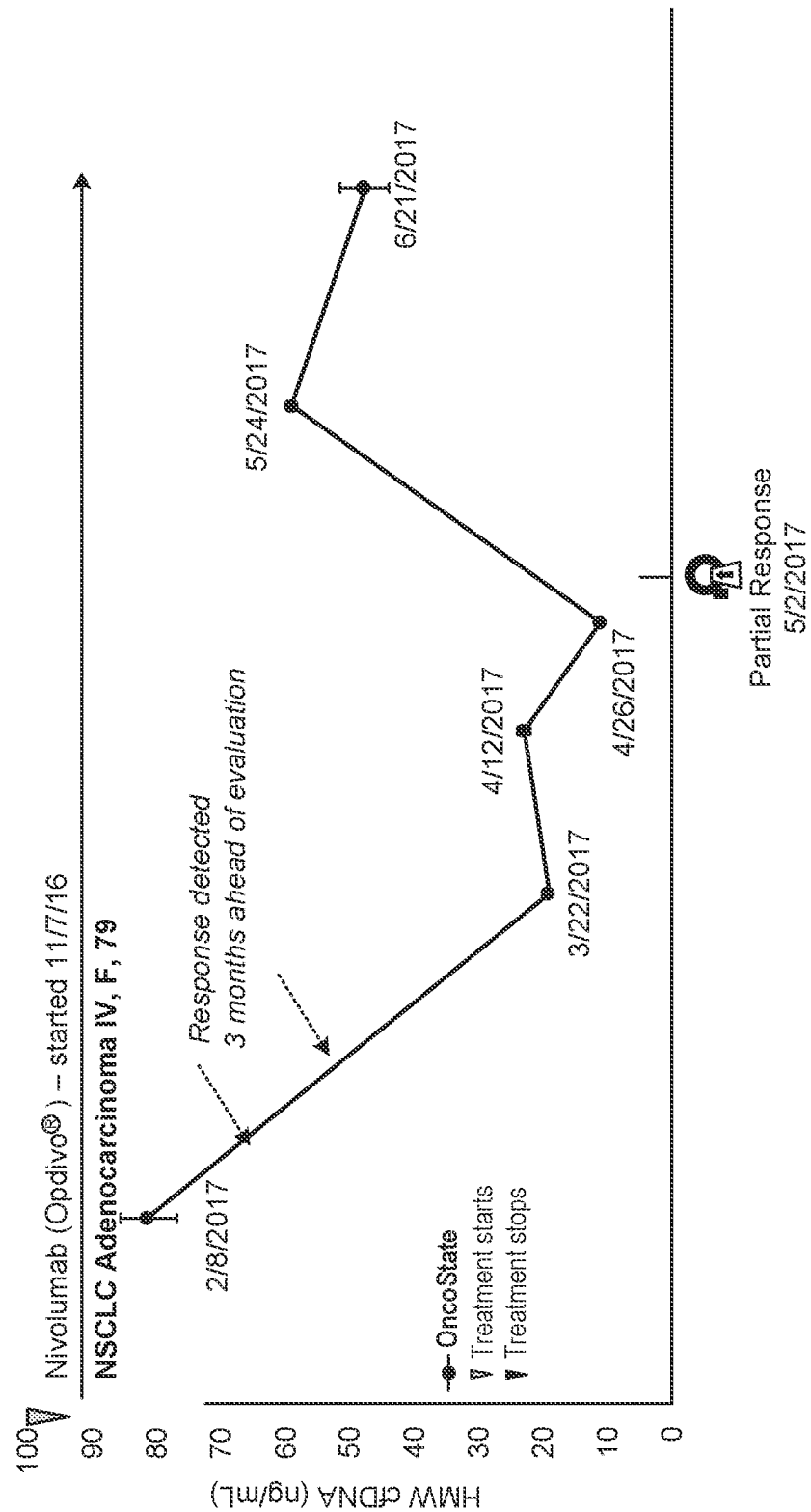

METHODS AND DEVICES FOR DETECTION OF MULTIPLE ANALYTES FROM A BIOLOGICAL SAMPLE

CROSS-REFERENCE

This patent application is a U.S. National Phase Entry of International Application No. PCT/US2018/066602, which claims the benefit of U.S. Provisional Patent Application No. 62/607,873, filed Dec. 19, 2017, which is incorporated herein by reference in its entirety.

BACKGROUND OF THE INVENTION

Many biological assays, whether for research or diagnostic uses, are capable of analyzing a single type of biologically relevant analyte. Current methods and devices often begin to analyze samples by isolating target molecules from a complex biological sample. New methods and devices are needed that can analyze a variety of macromolecules from a complex sample at once without the need to separate the different types of macromolecules from each other. Such methods can lead to increases in assay accuracy.

SUMMARY OF THE INVENTION

The devices, methods, and kits disclosed herein fulfill a need for improved analysis of complex biological samples. Some of the embodiments described herein can isolate, detect, quantify, and/or analyze a variety of macromolecules or cellular components found in biological samples, including samples obtained from subjects. Examples of such macromolecules and cellular components include DNA, including cell-free DNA and DNA fragments, RNA, nucleosomes, exosomes, extracellular vesicles, proteins, cell membrane fragments, mitochondria or cellular vesicles. As will be described herein, the ability to detect multiple types of macromolecules using the same devices and methods can simplify the processes of generating data, reduce or eliminate biases introduced by isolating and analyzing macromolecules from the same sample separately, and can increase the power and accuracy of sample analysis by increasing the number and types of molecules that can be simultaneously detected and analyzed. As a result, the embodiments described herein can increase the accuracy, precision, and confidence of results produced. These attributes can be enormously beneficial in assays used to detect, diagnose, classify, identify a disease or condition, determine a prognosis of a subject with a disease or condition, or evaluate the progress or efficacy of a treatment regimen for a subject with a disease or condition, including cancer.

Disclosed herein are methods for analyzing a biological sample. In some embodiments, the method comprises capturing a plurality of analytes in the biological sample using an electrode configured to generate an AC dielectrophoretic field, wherein the plurality analytes comprises at least two types of analytes selected from the group consisting of DNA, RNA, nucleosomes, exosomes, extracellular vesicles, proteins, cell membrane fragments, mitochondria and cellular vesicles; and detecting the plurality of analytes.

In some embodiments, capturing the plurality of analytes in the biological sample comprises using electrodes configured to generate a dielectrophoretic low field region and a dielectrophoretic high field region. In some embodiments, capturing the plurality of analytes in the biological sample comprises preferentially capturing a first analyte using a first electrode and a second analyte using a second electrode. In some embodiments, capturing the plurality of analytes in the biological sample comprises capturing more than one analyte on the same electrode.

In some embodiments, the DNA comprises cell-free DNA.

In some embodiments, the detecting comprises quantifying at least two types of analytes in the plurality of analytes. In some embodiments, detecting the plurality of analytes comprises detecting at least two different species of DNA, RNA, nucleosomes, exosomes, extracellular vesicles, proteins, cell membrane fragments, mitochondria or cellular vesicles. In some embodiments, quantifying the at least two types of analytes increases a diagnostic or predictive power or accuracy of the method by at least 10%, 20%, 30%, 40%, 50%, 60%, 70%, 80%, 90%, 100%, 150%, 200%, 300%, 400%, 500%, 1000% or more compared to a method in which only one type of analyte is quantified. In some embodiments, quantifying the at least two types of analytes decreases a false positive rate by at least 10%, 20%, 30%, 40%, 50%, 60%, 70%, 80%, 90%, 100%, 150%, 200%, 300%, 400%, 500%, 1000% or more compared to a method in which only one type of analyte is quantified. In some embodiments, quantifying the at least two types of analytes decreases a false negative rate by at least 10%, 20%, 30%, 40%, 50%, 60%, 70%, 80%, 90%, 100%, 150%, 200%, 300%, 400%, 500%, 1000% or more compared to a method in which only one type of analyte is quantified. In some embodiments, performance of the method is characterized by an area under the receiver operating characteristic (ROC) curve (AUC) ranging from 0.60 to 0.70, 0.70 to 0.79, 0.80 to 0.89, or 0.90 to 1.00.

In some embodiments, the biological sample is obtained from a subject. In some embodiments, the biological sample comprises a bodily fluid, blood, serum, plasma, urine, saliva, cells, tissue, or a combination thereof. In some embodiments, the biological sample comprises cells and the method further comprises lysing the cells.

In some embodiments, the method further comprises detecting a disease or condition in the subject using the at least two types of analytes detected in the biological sample. In some embodiments, the disease or condition is cancer. In some embodiments, detecting further comprises determining a type of cancer, a stage of cancer, an increase in tumor burden relative to an earlier time point, a decrease in tumor burden relative to an earlier time point, no change in tumor burden relative to an earlier time point, or the efficacy of a cancer therapy, or the absence of cancer.

In some embodiments, detecting comprises contacting an analyte of the plurality of analytes with an antibody that specifically binds to an analyte. In some embodiments, the antibody comprises a detectable label. In some embodiments, the detectable label comprises a fluorescent moiety. In some embodiments, an analyte of the plurality of analytes is selected from the group consisting of PD-L1, CA19.9, CA125, GPC-1, CEA, CA 15.3, Prolactin, Ki-67, estrogen receptor alpha, CD30, CD30L, CD10, Alpha-fetoprotein, survivin, prostate-specific antigen, AZU1, beta-human chorionic gonadotropin, and CYFRA-21.

In some embodiments, the detecting comprises contacting an analyte of the plurality of analytes with an oligonucleotide. In some embodiments, detecting comprises contacting an analyte of the plurality of analytes with an intercalating dye, a dye that preferentially binds to a major groove, or a dye that preferentially binds to a minor groove.

In some embodiments, the plurality of analytes comprises at least one of DNA and RNA and wherein the method further comprises amplifying at least one of the DNA or RNA by polymerase chain reaction. In some embodiments, the plurality of analytes comprises at least one of DNA and RNA and wherein detecting comprises sequencing the at least of DNA and RNA. In some embodiments, detecting comprises at least one of the group consisting of Quantitative Real Time PCR, enzyme-linked immunosorbent assay (ELISA), direct SYBR gold assay, direct PicoGreen assay, loss of heterozygosity (LOH) of microsatellite marker assay, electrophoresis, methylation analysis, MALDI-ToF, PCR, and digital PCR.

In some embodiments, the biological sample comprises fluid. In some embodiments, the method further comprises eluting the analytes from the electrode after the capturing.

In some embodiments, the dielectrophoretic low field region is produced using an alternating current having a voltage of 1 volt to 40 volts peak-peak; and/or a frequency of 5 Hz to 5,000,000 Hz. In some embodiments, the dielectrophoretic high field region is produced using an alternating current having a voltage of 1 volt to 40 volts peak-peak; and/or a frequency of 5 Hz to 5,000,000 Hz.

In some embodiments, the array of electrodes is coated with a hydrogel. In some embodiments, the hydrogel comprises two or more layers of a synthetic polymer. In some embodiments, the hydrogel is spin-coated onto the electrodes. In some embodiments, the hydrogel has a viscosity between about 0.5 cP to about 5 cP prior to spin-coating. In some embodiments, the hydrogel has a thickness between about 0.01 microns and 1 micron.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11A and FIG. 11B show the concentration of cfDNA in two patients as they undergo treatment for cancer. The figures show the concentration of cdDNA on the Y axis as ng/mL and the X axis represents time.

FIG. 12A shows RNA isolated on microelectrode devices from the ASPC-1 pancreatic cancer cell line. FIG. 12B shows RNA isolated from plasma samples obtained from patients with non-small cell lung cancer or healthy patients.

FIG. 13 shows carcinoembryonic antigen (CEA) isolated from plasma obtained from patients with adenocarcinoma. Some samples were artificially spiked with 2 g/mL of naked CEA protein. The staining is most prominent in exosome-bound CEA.

FIG. 14 shows cell-free DNA isolated from plasma obtained from patients with and without sepsis.

FIG. 15 shows a comparison of cfDNA concentrations for the healthy patient and each of the two sepsis patients. The results show an increase in cfDNA concentrations for fragments above 300 bp in size in sepsis patients as compared to healthy controls.

DETAILED DESCRIPTION OF THE INVENTION

Figure 1:
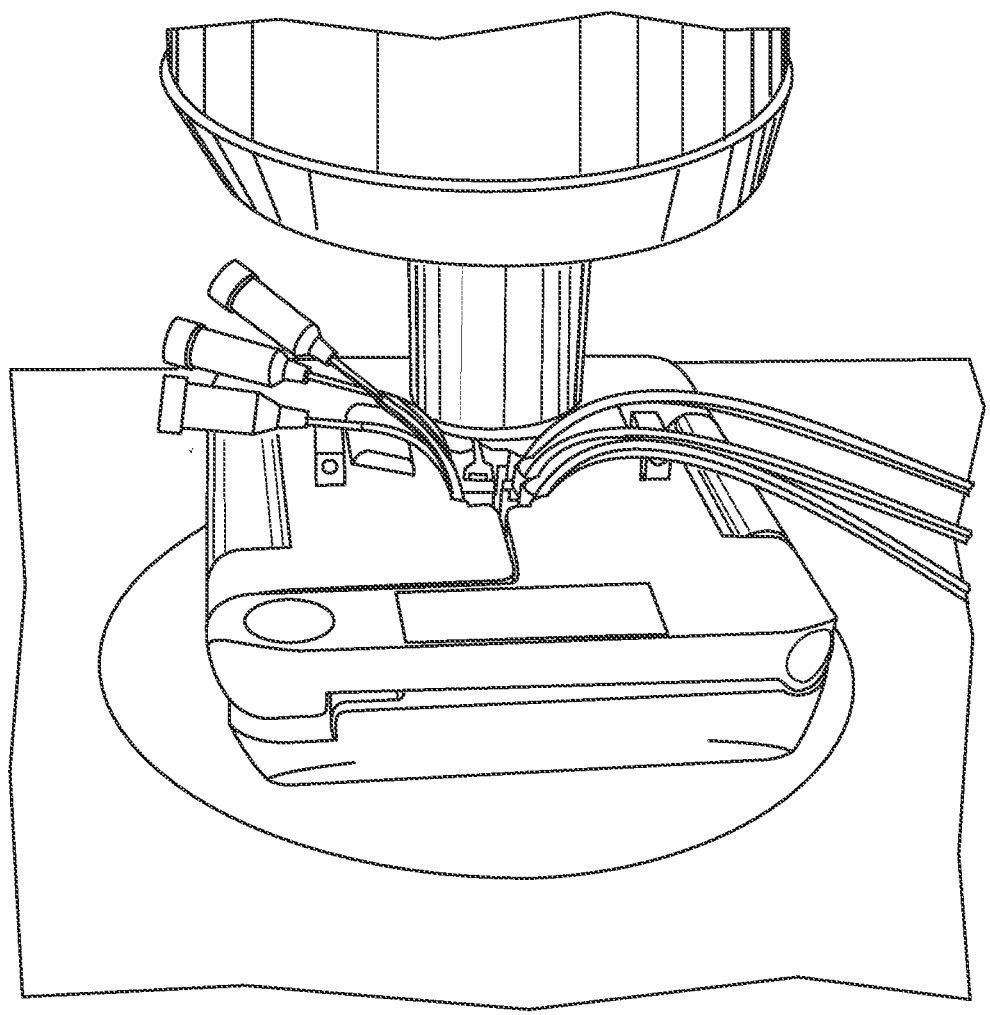
FIG. 1 shows a top view of an exemplary device.

Described herein are methods, devices and systems suitable for isolating or separating cellular components or molecules from a fluid composition. Examples of such components and molecules include DNA, including cell-free DNA and DNA fragments, RNA, nucleosomes, exosomes, extracellular vesicles, proteins, cell membrane fragments, mitochondria or cellular vesicles.

In specific embodiments, provided herein are methods of detecting and quantifying the components and molecules isolated from a fluid composition. In some embodiments, more than one type of component or molecule is isolated, detected, or quantified from the fluid composition. Many assays are traditionally directed to the detection and quantification of only a specific type of analyte. For example, QPCR is capable of detecting and quantifying nucleic acids but not proteins. ELISA, in contrast, is capable of detecting and quantifying proteins, but not nucleic acids. As a result, studies or tests that rely on data from different types of analytes are often performed as a series of separate tests. In one exemplarily advantage of the methods, devices, and systems described herein, several different types of analytes can be isolated, detected, and quantified at once. This can allow, for example, DNA, including cell-free DNA and DNA fragments, RNA, including cell-free RNA, nucleosomes, exosomes, extracellular vesicles, proteins (including proteins expressed on the surface of endosomes), protein fragments, cell membrane fragments, mitochondria, cellular vesicles, and vesicles of endosomal origin to be detected and quantified as part of the same assay. In some embodiments, the various analytes can be processed together, stained together, and visualized together. As a result, the workflows needed to detect a variety of analytes can be vastly simplified.

In another exemplary advantage, some assays benefit from the use of multiple variables and the detection of multiple biomarkers. In cancer, for example, there are a variety of different biomarkers that may indicate the presence of cancer. The quantities of cell-free DNA fragments of particular sizes present in a sample can be indicative of a likelihood of the presence of cancer. Likewise, the presence of specific proteins, including PD-L1 or CA125, can also indicate a likelihood of a presence of cancer. Other diseases or conditions are also contemplated. These include, for example, infectious diseases or conditions, sepsis, alloimmune and autoimmune diseases or conditions, including those related to transplant complications or rejection, inflammatory diseases or conditions, or hear disease or heart conditions.

The inventors have discovered that these tests may sometimes be inconclusive when done in isolation. A patient with a normal cell-free DNA profile may be high for PD-L1 expression. This can sometimes be true if tests yield results that are on the edge of being classified as either cancer or non-cancer. The inventors have surprisingly discovered that tests that can simultaneously detect more than one analyte can be more accurate, more precise, more selective, more specific, and more comprehensive than tests that can only detect one of protein, nucleic acid, or other cellular component. The surprising results presented herein show that the analysis of multiple types of analytes may be able to better diagnose and detect diseases or conditions in patients who might otherwise be classified as normal by traditional tests. In some aspects, the performance of the methods described herein can be characterized by an area under the receiver operating characteristic (ROC) curve (AUC) ranging from 0.60 to 0.69, 0.70 to 0.79, 0.80 to 0.89, or 0.90 to 1.00. In some aspects, the methods described herein can be 5%, 10%, 20%, 30%, 40%, 50%, 60%, 70%, 80%, 90%, 100%, 200%, 300%, 400%, 500%, 600%, 700%, 800%, 900%, 1000%, or more than 1000% more accurate, selective, precise, specific or comprehensive than other tests used to detect, diagnose or analyze diseases or conditions in a patient, such as pathology, ELISA, QPCR, or DNA sequencing.

Provided in certain embodiments herein are methods, devices and systems for isolating or separating particles or molecules from a fluid composition, the methods, devices, and systems comprising applying the fluid to a device comprising an array of electrodes and being capable of generating AC electrokinetic forces (e.g., when the array of electrodes are energized). In some embodiments, the dielectrophoretic field, is a component of AC electrokinetic force effects. In other embodiments, the component of AC electrokinetic force effects is AC electroosmosis or AC electrothermal effects. In some embodiments the AC electrokinetic force, including dielectrophoretic fields, comprises high-field regions (positive DEP, i.e. area where there is a strong concentration of electric field lines due to a non-uniform electric field) and/or low-field regions (negative DEP, i.e. area where there is a weak concentration of electric field lines due to a non-uniform electric field).

In specific instances, the particles, cellular components, or molecules (e.g., nucleic acid) are isolated (e.g., isolated or separated from cells) in a field region (e.g., a high field region) of the dielectrophoretic field. In some embodiments, the particles, cellular components, or molecules are isolated from a bodily fluid, blood, serum, plasma, urine, saliva, cells, tissue, or a combination thereof. In some embodiments, the particles, cellular components, or molecules are isolated from a fluid or a portion of a fluid that is cell-free. In some embodiments, the particles, cellular components, or molecules are or comprise DNA, including cell-free DNA, RNA, nucleosomes, exosomes, extracellular vesicles, proteins, cell membrane fragments, mitochondria or cellular vesicles, as well as fragments or portions of any of the above.

One would understand that any analyte may be detected using the methods described herein. Analytes include, in some instances, biological markers which may, in turn, be protein markers. Markers also include, in some instances, viruses or cells. In some embodiments, the analyte is detected using an antibody. In some embodiments, the antibody is labeled with a detectable marker. In some embodiments, the detectable marker is a fluorescent marker.

A fluorescent or luminescent tag to be used in the methods described herein may be any suitable fluorescent or luminescent protein used for labeling nucleic acids (DNA, RNA) and proteins, including, luciferase, horseradish peroxidase, acridine dyes, cyanine dyes, fluorone dyes, oxazine dyes, phenanthridine dyes and rhodamine dyes, which includes but is not limited to, rhodamine, Cy2, Cy3, Cy5 Alexa fluorophores, luciferin, fura-2 dyes, green fluorescent protein (GFP), cyan fluorescent protein, and yellow fluorescent protein. The antibodies disclosed herein can be custom synthesized with a variety of fluorescent tags and fluorophores.

It would be understood that the primary and secondary antibodies, including conjugated primary and secondary antibodies, utilized in the methods described herein specifically bind to an analyte to be detected or to an antibody that binds to an analyte to be detected. The term "specifically binds" means that an antibody bind to an epitope with greater affinity than it binds an unrelated amino acid sequence. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody for an unrelated amino acid sequence.

"Epitope" refers to that portion of an antigen or other macromolecule capable of forming a binding interaction with the variable region binding pocket of an antibody.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains (Fc) that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("κ" or "K") and lambda or ("λ"), based on the amino acid sequences of their constant domains.

The terms "antigen-binding portion of an antibody," "antigen-binding fragment," "antigen-binding domain," "antibody fragment" or a "functional fragment of an antibody" are used interchangeably herein to refer to one or more fragments of an antibody that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment containing two Fab fragments linked by a disulfide bridge at the hinge region; (iii) a Fd fragment consisting of the $V_H$ and $C_{H1}$ domains; (iv) a Fv fragment containing the $V_L$ and $V_H$ domains of a single arm of an antibody, (v) a dAb fragment (Ward et al., (1989) Nature 341:544 546), which containing a $V_H$ domain; and (vi) an isolated CDR. Additionally included in this definition are "one-half" antibodies comprising a single heavy chain and a single light chain. Other forms of single chain antibodies, such as diabodies are also encompassed herein.

A control antibody to be used in a method described herein does not specifically bind to an analyte to be detected.

The immunoassays described herein may be conducted in a device described herein.

Other assays that may be utilized for this assessment include, but are not limited to, fluorescence resonance energy transfer (FRET), in situ hybridization (ISH), fluorescent in situ hybridization (FISH), and Comparative Genomic Hybridization (CGH).

Application of an AC electrokinetic field in the methods described herein comprises dielectrophoresis. Applying the AC electrokinetic field creates areas of low and high dielectrophoresis. This application separates bound analyte by size and bound analyte can be detected and, in some instances, quantified using methods known in the art.

In certain instances, calibrators can be run along with a sample of interest in order to make a direct quantification of the isolated protein marker. The calibrator can be a spiked protein of interest at a fixed concentration in a controlled buffer.

In some embodiments, the detectable marker is detected by fluorescent microscopy.

Non-limiting examples of markers include, for example, cancer markers and markers of inflammation. While cancer markers and markers of inflammation are exemplified herein, one would understand that the described methods are not limited to the disclosed markers. The immunoassays disclosed herein can be used with other markers, including but not limited to tumor markers, cardiac markers, anemia markers, metabolic markers, kidney markers, diabetes markers, thyroid hormone markers, reproductive hormone markers and combinations thereof.

Protein markers for detection using the methods described herein include, but are not limited to, carcinoembryonic antigen (CEA), CA125, CA27.29, CA15-3, CA19.9, Prolactin, Ki-67, estrogen receptor alpha, CD30, CD30L, CD10, surviving, AZU1, alpha-fetoprotein (αFP), β-human chorionic gonadotropin. (βHCG), glypican-1 (GPC-1), CYFRA-21, RNA-based markers and prostate specific antigen (PSA).

Additional cancer markers that may be detected using the methods described herein include, but are not limited to, BRAF, BRCA1, BRCA2, CD20, Calcitonin, Calretinin, CD34, CD99MIC 2, CD117, Chromogranin, Cytokeratin (various types), Desmin, Epithelial membrane antigen (EMA), Factor VIII, CD31 FL1, Glial fibrillary acidic protein (GFAP), Gross cystic disease fluid protein (GCDFP-15), HER2/neu, HER3, HMB-45, Human chorionic gonadotropin (hCG), inhibin, keratin (various types), lymphocyte marker, MART-1 (Melan-A), Mesothelin, Myo D1, MUC-1, MUC-16 neuron-specific enolase (NSE), placental alkaline phosphatase (PLAP), leukocyte common antigen (CD45), S100 protein, synaptophysin, thyroglobulin, thyroid transcription factor-1, Tumor M2-PK, and vimentin.

Additional markers of inflammation that may be detecting using the methods described herein include, but are not limited to, Carcinoembryonic antigen (CEA), plasma α-fetoprotein (αFP), β human chorionic gonadotrophin (βHCG), C-reactive protein (CRP), Lysosome granules, Histamine, IFN-gamma, Interleukin (IL)-8, Leukotriene B4, Nitric oxide, Prostaglandins, TNF-α, and IL-1.

Cardiac markers include Creatine Kinase (CKMB), Myoglobin and Troponin 1. Markers for anemia include Ferritin. Metabolic markers include Cortisol (CORT) and Human Growth Hormone (HGH). Kidney markers include Cystatin C (CysC), $β_2$ Microglobulin (BMG), intact Parathyroid Hormone (iPTH). Diabetes markers include C-peptide, Glycated Homoglobin (HbAlc) and Insulin (IRI). Thyroid hormone markers include Tyroid-Stimulating Hormone (TSH) while reproductive hormone markers include PHCG, Follicle-stimulating hormone (FSH), Luteinizing Hormone II (LH II) and Prolactatin (PRL).

In some embodiments, the method, device, or system further includes one or more of the following steps: concentrating cells of interest in a first dielectrophoretic field region (e.g., a high field DEP region), lysing cells in the first dielectrophoretic field region, and/or concentrating nucleic acid in a first or second dielectrophoretic field region. In other embodiments, the method, device, or system includes one or more of the following steps: concentrating cells in a first dielectrophoretic field region (e.g., a low field DEP region), concentrating nucleic acid in a second dielectrophoretic field region (e.g., a high field DEP region), and washing away the cells and residual material. The method also optionally includes devices and/or systems capable of performing one or more of the following steps: washing or otherwise removing residual (e.g., cellular) material from the nucleic acid (e.g., rinsing the array with water or buffer while the nucleic acid is concentrated and maintained within a high field DEP region of the array), degrading residual proteins (e.g., residual proteins from lysed cells and/or other sources, such degradation occurring according to any suitable mechanism, such as with heat, a protease, or a chemical), flushing degraded proteins from the nucleic acid, and collecting the nucleic acid. In some embodiments, the result of the methods, operation of the devices, and operation of the systems described herein is an isolated nucleic acid, optionally of suitable quantity and purity for DNA sequencing.

In some instances, it is advantageous that the methods described herein are performed in a short amount of time, the devices are operated in a short amount of time, and the systems are operated in a short amount of time. In some embodiments, the period of time is short with reference to the "procedure time" measured from the time between adding the fluid to the device and obtaining isolated nucleic acid. In some embodiments, the procedure time is less than 3 hours, less than 2 hours, less than 1 hour, less than 30 minutes, less than 20 minutes, less than 10 minutes, or less than 5 minutes.

In another aspect, the period of time is short with reference to the "hands-on time" measured as the cumulative amount of time that a person must attend to the procedure from the time between adding the fluid to the device and obtaining isolated nucleic acid. In some embodiments, the hands-on time is less than 40 minutes, less than 20 minutes, less than 10 minutes, less than 5 minute, less than 1 minute, or less than 30 seconds.

In some instances, it is advantageous that the devices described herein comprise a single vessel, the systems described herein comprise a device comprising a single vessel and the methods described herein can be performed in a single vessel, e.g., in a dielectrophoretic device as described herein. In some aspects, such a single-vessel embodiment minimizes the number of fluid handling steps and/or is performed in a short amount of time. In some instances, the present methods, devices and systems are contrasted with methods, devices and systems that use one or more centrifugation steps and/or medium exchanges. In some instances, centrifugation increases the amount of hands-on time required to isolate nucleic acids. In another aspect, the single-vessel procedure or device isolates nucleic acids using a minimal amount of consumable reagents.

Devices and Systems

In some embodiments, described herein are devices for collecting cellular material from a fluid. In one aspect, described herein are devices for collecting a cellular material from a fluid comprising cells, from a cell-free portion of a fluid, or other particulate material.

In some embodiments, disclosed herein is a device for isolating cellular material, the device comprising: a. a housing; b. a heater or thermal source and/or a reservoir comprising a protein degradation agent; and c. a plurality of alternating current (AC) electrodes within the housing, the AC electrodes configured to be selectively energized to establish AC electrokinetic high field and AC electrokinetic low field regions, whereby AC electrokinetic effects provide for concentration of cells in low field regions of the device. In some embodiments, the plurality of electrodes is configured to be selectively energized to establish a dielectrophoretic high field and dielectrophoretic low field regions. In some embodiments, the protein degradation agent is a protease. In some embodiments, the protein degradation agent is Proteinase K. In some embodiments, the device further comprises a second reservoir comprising an eluant.

In some embodiments, disclosed herein is a device comprising: a. a plurality of alternating current (AC) electrodes, the AC electrodes configured to be selectively energized to establish AC electrokinetic high field and AC electrokinetic low field regions; and b. a module capable of thermocycling and performing PCR or other enzymatic reactions.

In some embodiments, disclosed herein is a device comprising: a. a plurality of alternating current (AC) electrodes, the AC electrodes configured to be selectively energized to establish AC electrokinetic high field and AC electrokinetic low field regions; and b. a module capable of imaging the material captured or isolated by the AC electrodes. Some embodiments also include chambers and fluidics for adding reagents and removing that allow for the visualization of the captured materials.

In some embodiments, the plurality of electrodes is configured to be selectively energized to establish a dielectrophoretic high field and dielectrophoretic low field regions. In some embodiments, the device is capable of isolating DNA, including cell-free DNA and DNA fragments, RNA, nucleosomes, exosomes, extracellular vesicles, proteins, cell membrane fragments, mitochondria and cellular vesicles from a biological sample comprising fluid. In some embodiments, the device is capable of isolating these materials from cells in the biological sample. In some embodiments, the device is capable of performing PCR amplification or other enzymatic reactions. In some embodiments, DNA is isolated and PCR or other enzymatic reaction is performed in a single chamber. In some embodiments, DNA is isolated and PCR or other enzymatic reaction is performed in multiple regions of a single chamber. In some embodiments, DNA is isolated and PCR or other enzymatic reaction is performed in multiple chambers.

In some embodiments, the device further comprises at least one of an elution tube, a chamber and a reservoir to perform PCR amplification or other enzymatic reaction. In some embodiments, PCR amplification or other enzymatic reaction is performed in a serpentine microchannel comprising a plurality of temperature zones. In some embodiments, PCR amplification or other enzymatic reaction is performed in aqueous droplets entrapped in immiscible fluids (i.e., digital PCR). In some embodiments, the thermocycling comprises convection. In some embodiments, the device comprises a surface contacting or proximal to the electrodes, wherein the surface is functionalized with biological ligands that are capable of selectively capturing biomolecules.

In some embodiments, disclosed herein is a system for isolating a cellular material from a biological sample, the system comprising: a. a device comprising a plurality of alternating current (AC) electrodes, the AC electrodes configured to be selectively energized to establish AC electrokinetic high field and AC electrokinetic low field regions, whereby AC electrokinetic effects provide for concentration of cells in high field regions of the device; and b. a sequencer, thermocycler or other device for performing enzymatic reactions on isolated or collected nucleic acid. In some embodiments, the plurality of electrodes is configured to be selectively energized to establish a dielectrophoretic high field and dielectrophoretic low field regions.

In various embodiments, DEP fields are created or capable of being created by selectively energizing an array of electrodes as described herein. The electrodes are optionally made of any suitable material resistant to corrosion, including metals, such as noble metals (e.g. platinum, platinum iridium alloy, palladium, gold, and the like). In various embodiments, electrodes are of any suitable size, of any suitable orientation, of any suitable spacing, energized or capable of being energized in any suitable manner, and the like such that suitable DEP and/or other electrokinetic fields are produced.

In some embodiments described herein are methods, devices and systems in which the electrodes are placed into separate chambers and positive DEP regions and negative DEP regions are created within an inner chamber by passage of the AC DEP field through pore or hole structures. Various geometries are used to form the desired positive DEP (high field) regions and DEP negative (low field) regions for carrying cellular, microparticle, nanoparticle, and nucleic acid separations. In some embodiments, pore or hole structures contain (or are filled with) porous material (hydrogels) or are covered with porous membrane structures. In some embodiments, by segregating the electrodes into separate chambers, such pore/hole structure DEP devices reduce electrochemistry effects, heating, or chaotic fluidic movement from occurring in the inner separation chamber during the DEP process.

In one aspect, described herein is a device comprising electrodes, wherein the electrodes are placed into separate chambers and DEP fields are created within an inner chamber by passage through pore structures. The exemplary device includes a plurality of electrodes and electrode-containing chambers within a housing. A controller of the device independently controls the electrodes, as described further in PCT patent publication WO 2009/146143 A2, which is incorporated herein for such disclosure.

In some embodiments, chambered devices are created with a variety of pore and/or hole structures (nanoscale, microscale and even macroscale) and contain membranes, gels or filtering materials which control, confine or prevent cells, nanoparticles or other entities from diffusing or being transported into the inner chambers while the AC/DC electric fields, solute molecules, buffer and other small molecules can pass through the chambers.

In various embodiments, a variety of configurations for the devices are possible. For example, a device comprising a larger array of electrodes, for example in a square or rectangular pattern configured to create a repeating non-uniform electric field to enable AC electrokinetics. For illustrative purposes only, a suitable electrode array may include, but is not limited to, a 10×10 electrode configuration, a 50×50 electrode configuration, a 10×100 electrode configuration, 20×100 electrode configuration, or a 20×80 electrode configuration.

Such devices include, but are not limited to, multiplexed electrode and chambered devices, devices that allow reconfigurable electric field patterns to be created, devices that combine DC electrophoretic and fluidic processes; sample preparation devices, sample preparation, enzymatic manipulation of isolated nucleic acid molecules and diagnostic devices that include subsequent detection and analysis, lab-on-chip devices, point-of-care and other clinical diagnostic systems or versions.

In some embodiments, a planar platinum electrode array device comprises a housing through which a sample fluid flows. In some embodiments, fluid flows from an inlet end to an outlet end, optionally comprising a lateral analyte outlet. The exemplary device includes multiple AC electrodes. In some embodiments, the sample consists of a combination of micron-sized entities or cells, larger nanoparticulates and smaller nanoparticulates or biomolecules. In some instances, the larger nanoparticulates are cellular debris dispersed in the sample. In some embodiments, the smaller nanoparticulates are proteins, smaller DNA, RNA and cellular fragments. In some embodiments, the planar electrode array device is a 60×20 electrode array that is optionally sectioned into three 20×20 arrays that can be separately controlled but operated simultaneously. The optional auxiliary DC electrodes can be switched on to positive charge, while the optional DC electrodes are switched on to negative charge for electrophoretic purposes. In some instances, each of the controlled AC and DC systems is used in both a continuous and/or pulsed manner (e.g., each can be pulsed on and off at relatively short time intervals) in various embodiments. The optional planar electrode arrays along the sides of the sample flow, when over-layered with nanoporous material (e.g., a hydrogel of synthetic polymer), are optionally used to generate DC electrophoretic forces as well as AC DEP. Additionally, microelectrophoretic separation processes is optionally carried out within the nanopore layers using planar electrodes in the array and/or auxiliary electrodes in the x-y-z dimensions.

In various embodiments these methods, devices and systems are operated in the AC frequency range of from 1,000 Hz to 100 MHz, at voltages which could range from approximately 1 volt to 2000 volts pk-pk; at DC voltages from 1 volt to 1000 volts, at flow rates of from 10 microliters per minute to 10 milliliter per minute, and in temperature ranges from 1° C. to 120° C. In some embodiments, the methods, devices and systems are operated in AC frequency ranges of from about 3 to about 15 kHz. In some embodiments, the methods, devices, and systems are operated at voltages of from 5-25 volts pk-pk. In some embodiments, the methods, devices and systems are operated at voltages of from about 1 to about 50 volts/cm. In some embodiments, the methods, devices and systems are operated at DC voltages of from about 1 to about 5 volts. In some embodiments, the methods, devices and systems are operated at a flow rate of from about 10 microliters to about 500 microliters per minute. In some embodiments, the methods, devices and systems are operated in temperature ranges of from about 20° C. to about 60° C. In some embodiments, the methods, devices and systems are operated in AC frequency ranges of from 1,000 Hz to 10 MHz. In some embodiments, the methods, devices and systems are operated in AC frequency ranges of from 1,000 Hz to 1 MHz. In some embodiments, the methods, devices and systems are operated in AC frequency ranges of from 1,000 Hz to 100 kHz. In some embodiments, the methods, devices and systems are operated in AC frequency ranges of from 1,000 Hz to 10 kHz. In some embodiments, the methods, devices and systems are operated in AC frequency ranges of from 10 kHz to 100 kHz. In some embodiments, the methods, devices and systems are operated in AC frequency ranges of from 100 kHz to 1 MHz. In some embodiments, the methods, devices and systems are operated at voltages from approximately 1 volt to 1500 volts pk-pk. In some embodiments, the methods, devices and systems are operated at voltages from approximately 1 volt to 1500 volts pk-pk. In some embodiments, the methods, devices and systems are operated at voltages from approximately 1 volt to 1000 volts pk-pk. In some embodiments, the methods, devices and systems are operated at voltages from approximately 1 volt to 500 volts pk-pk. In some embodiments, the methods, devices and systems are operated at voltages from approximately 1 volt to 250 volts pk-pk. In some embodiments, the methods, devices and systems are operated at voltages from approximately 1 volt to 100 volts pk-pk. In some embodiments, the methods, devices and systems are operated at voltages from approximately 1 volt to 50 volts pk-pk. In some embodiments, the methods, devices and systems are operated at DC voltages from 1 volt to 1000 volts. In some embodiments, the methods, devices and systems are operated at DC voltages from 1 volt to 500 volts. In some embodiments, the methods, devices and systems are operated at DC voltages from 1 volt to 250 volts. In some embodiments, the methods, devices and systems are operated at DC voltages from 1 volt to 100 volts. In some embodiments, the methods, devices and systems are operated at DC voltages from 1 volt to 50 volts. In some embodiments, the methods, devices, and systems are operated at flow rates of from 10 microliters per minute to 1 ml per minute. In some embodiments, the methods, devices, and systems are operated at flow rates of from 0.1 microliters per minute to 500 microliters per minute. In some embodiments, the methods, devices, and systems are operated at flow rates of from 0.1 microliters per minute to 250 microliters per minute. In some embodiments, the methods, devices, and systems are operated at flow rates of from 0.1 microliters per minute to 100 microliters per minute. In some embodiments, the methods, devices, and systems are operated in temperature ranges from 1° C. to 100° C. In some embodiments, the methods, devices, and systems are operated in temperature ranges from 20° C. to 95° C. In some embodiments, the methods, devices, and systems are operated in temperature ranges from 25° C. to 100° C. In some embodiments, the methods, devices, and systems are operated at room temperature.

In some embodiments, the controller independently controls each of the electrodes. In some embodiments, the controller is externally connected to the device such as by a socket and plug connection, or is integrated with the device housing.

Also described herein are scaled sectioned (x-y dimensional) arrays of robust electrodes and strategically placed (x-y-z dimensional) arrangements of auxiliary electrodes that combine DEP, electrophoretic, and fluidic forces, and use thereof. In some embodiments, clinically relevant volumes of blood, serum, plasma, or other samples are more directly analyzed under higher ionic strength and/or conductance conditions. Described herein is the overlaying of robust electrode structures (e.g. platinum, palladium, gold, etc.) with one or more porous layers of materials (natural or synthetic porous hydrogels, membranes, controlled nanopore materials, and thin dielectric layered materials) to reduce the effects of any electrochemistry (electrolysis) reactions, heating, and chaotic fluid movement that may occur on or near the electrodes, and still allow the effective separation of cells, bacteria, virus, nanoparticles, DNA, and other biomolecules to be carried out. In some embodiments, in addition to using AC frequency crossover points to achieve higher resolution separations, on-device (on-array) DC microelectrophoresis is used for secondary separations. For example, the separation of DNA nanoparticulates (20-50 kb), high molecular weight DNA (5-20 kb), intermediate molecular weight DNA (1-5 kb), and lower molecular weight DNA (0.1-1 kb) fragments may be accomplished through DC microelectrophoresis on the array. In some embodiments, the device is sub-sectioned, optionally for purposes of concurrent separations of different blood cells, bacteria and virus, and DNA carried out simultaneously on such a device.

In some embodiments, the device comprises a housing and a heater or thermal source and/or a reservoir comprising a protein degradation agent. In some embodiments, the heater or thermal source is capable of increasing the temperature of the fluid to a desired temperature (e.g., to a temperature suitable for degrading proteins, about 30° C., 40° C., 50° C., 60° C., 70° C., or the like). In some embodiments, the heater or thermal source is suitable for operation as a PCR thermocycler. IN other embodiments, the heater or thermal source is used to maintain a constant temperature (isothermal conditions). In some embodiments, the protein degradation agent is a protease. In other embodiments, the protein degradation agent is Proteinase K and the heater or thermal source is used to inactivate the protein degradation agent.

In some embodiments, the device also comprises a plurality of alternating current (AC) electrodes within the housing, the AC electrodes capable of being configured to be selectively energized to establish dielectrophoretic (DEP) high field and dielectrophoretic (DEP) low field regions, whereby AC electrokinetic effects provide for concentration of cells in low field regions of the device. In some embodiments, the electrodes are selectively energized to provide the first AC electrokinetic field region and subsequently or continuously selectively energized to provide the second AC electrokinetic field region. For example, further description of the electrodes and the concentration of cells in DEP fields is found in PCT patent publication WO 2009/146143 A2, which is incorporated herein for such disclosure.

In some embodiments, the device comprises a second reservoir comprising an eluant. The eluant is any fluid suitable for eluting the isolated cellular material from the device. In some instances the eluant is water or a buffer. In some instances, the eluant comprises reagents required for a DNA sequencing method.

In some embodiments, the device comprises a plurality of reservoirs, each reservoir containing a reagents useful in the staining and washing of the isolated cellular material in the device. Examples include antibodies, oligonucleotides, probes, and dyes, buffers, washes, water, detergents, and solvents.

Also provided herein are systems and devices comprising a plurality of alternating current (AC) electrodes, the AC electrodes configured to be selectively energized to establish dielectrophoretic (DEP) high field and dielectrophoretic (DEP) low field regions. In some instances, AC electrokinetic effects provide for concentration of cells in low field regions and/or concentration (or collection or isolation) of molecules (e.g., macromolecules, such as nucleic acid) in high field regions of the DEP field.

Also provided herein are systems and devices comprising a plurality of direct current (DC) electrodes. In some embodiments, the plurality of DC electrodes comprises at least two rectangular electrodes, spread throughout the array. In some embodiments, the electrodes are located at the edges of the array. In some embodiments, DC electrodes are interspersed between AC electrodes.

In some embodiments, a system or device described herein comprises a means for manipulating nucleic acid. In some embodiments, a system or device described herein includes a means of performing enzymatic reactions. In other embodiments, a system or device described herein includes a means of performing polymerase chain reaction, isothermal amplification, ligation reactions, restriction analysis, nucleic acid cloning, transcription or translation assays, or other enzymatic-based molecular biology assay.

In some embodiments, a system or device described herein comprises a nucleic acid sequencer. The sequencer is optionally any suitable DNA sequencing device including but not limited to a Sanger sequencer, pyro-sequencer, ion semiconductor sequencer, polony sequencer, sequencing by ligation device, DNA nanoball sequencing device, or single molecule sequencing device.

In some embodiments, a system or device described herein is capable of maintaining a constant temperature. In some embodiments, a system or device described herein is capable of cooling the array or chamber. In some embodiments, a system or device described herein is capable of heating the array or chamber. In some embodiments, a system or device described herein comprises a thermocycler. In some embodiments, the devices disclosed herein comprises a localized temperature control element. In some embodiments, the devices disclosed herein are capable of both sensing and controlling temperature.

In some embodiments, the devices further comprise heating or thermal elements. In some embodiments, a heating or thermal element is localized underneath an electrode. In some embodiments, the heating or thermal elements comprise a metal. In some embodiments, the heating or thermal elements comprise tantalum, aluminum, tungsten, or a combination thereof. Generally, the temperature achieved by a heating or thermal element is proportional to the current running through it. In some embodiments, the devices disclosed herein comprise localized cooling elements. In some embodiments, heat resistant elements are placed directly under the exposed electrode array. In some embodiments, the devices disclosed herein are capable of achieving and maintaining a temperature between about 20° C. and about 120° C. In some embodiments, the devices disclosed herein are capable of achieving and maintaining a temperature between about 30° C. and about 100° C. In other embodiments, the devices disclosed herein are capable of achieving and maintaining a temperature between about 20° C. and about 95° C. In some embodiments, the devices disclosed herein are capable of achieving and maintaining a temperature between about 25° C. and about 90° C., between about 25° C. and about 85° C., between about 25° C. and about 75° C., between about 25° C. and about 65° C. or between about 25° C. and about 55° C. In some embodiments, the devices disclosed herein are capable of achieving and maintaining a temperature of about 20° C., about 30° C., about 40° C., about 50° C., about 60° C., about 70° C., about 80° C., about 90° C., about 100° C., about 110° C. or about 120° C.

Electrodes

The plurality of alternating current electrodes are optionally configured in any manner suitable for the separation processes described herein. For example, further description of the system or device including electrodes and/or concentration of cells in DEP fields is found in PCT patent publication WO 2009/146143, which is incorporated herein for such disclosure.

In some embodiments, the electrodes disclosed herein can comprise any suitable metal. In some embodiments, the electrodes can include but are not limited to: aluminum, copper, carbon, iron, silver, gold, palladium, platinum, iridium, platinum iridium alloy, ruthenium, rhodium, osmium, tantalum, titanium, tungsten, polysilicon, and indium tin oxide, or combinations thereof, as well as silicide materials such as platinum silicide, titanium silicide, gold silicide, or tungsten silicide. In some embodiments, the electrodes can comprise a conductive ink capable of being screen-printed.

In some embodiments, the edge to edge (E2E) to diameter ratio of an electrode is about 0.5 mm to about 5 mm. In some embodiments, the E2E to diameter ratio is about 1 mm to about 4 mm. In some embodiments, the E2E to diameter ratio is about 1 mm to about 3 mm. In some embodiments, the E2E to diameter ratio is about 1 mm to about 2 mm. In some embodiments, the E2E to diameter ratio is about 2 mm to about 5 mm. In some embodiments, the E2E to diameter ratio is about 1 mm. In some embodiments, the E2E to diameter ratio is about 2 mm. In some embodiments, the E2E to diameter ratio is about 3 mm. In some embodiments, the E2E to diameter ratio is about 4 mm. In some embodiments, the E2E to diameter ratio is about 5 mm.

In some embodiments, the electrodes disclosed herein are dry-etched. In some embodiments, the electrodes are wet etched. In some embodiments, the electrodes undergo a combination of dry etching and wet etching.

In some embodiments, each electrode is individually site-controlled.

In some embodiments, an array of electrodes is controlled as a unit.

In some embodiments, a passivation layer is employed. In some embodiments, a passivation layer can be formed from any suitable material known in the art. In some embodiments, the passivation layer comprises silicon nitride. In some embodiments, the passivation layer comprises silicon dioxide. In some embodiments, the passivation layer has a relative electrical permittivity of from about 2.0 to about 8.0. In some embodiments, the passivation layer has a relative electrical permittivity of from about 3.0 to about 8.0, about 4.0 to about 8.0 or about 5.0 to about 8.0. In some embodiments, the passivation layer has a relative electrical permittivity of about 2.0 to about 4.0. In some embodiments, the passivation layer has a relative electrical permittivity of from about 2.0 to about 3.0. In some embodiments, the passivation layer has a relative electrical permittivity of about 2.0, about 2.5, about 3.0, about 3.5 or about 4.0.

In some embodiments, the passivation layer is between about 0.1 microns and about 10 microns in thickness. In some embodiments, the passivation layer is between about 0.5 microns and 8 microns in thickness. In some embodiments, the passivation layer is between about 1.0 micron and 5 microns in thickness. In some embodiments, the passivation layer is between about 1.0 micron and 4 microns in thickness. In some embodiments, the passivation layer is between about 1.0 micron and 3 microns in thickness. In some embodiments, the passivation layer is between about 0.25 microns and 2 microns in thickness. In some embodiments, the passivation layer is between about 0.25 microns and 1 micron in thickness.

In some embodiments, the passivation layer is comprised of any suitable insulative low k dielectric material, including but not limited to silicon nitride or silicon dioxide. In some embodiments, the passivation layer is chosen from the group consisting of polyamids, carbon, doped silicon nitride, carbon doped silicon dioxide, fluorine doped silicon nitride, fluorine doped silicon dioxide, porous silicon dioxide, or any combinations thereof. In some embodiments, the passivation layer can comprise a dielectric ink capable of being screen-printed.

Electrode Geometry

In some embodiments, the electrodes disclosed herein can be arranged in any manner suitable for practicing the methods disclosed herein.

In some embodiments, the electrodes are in a dot configuration, e.g. the electrodes comprises a generally circular or round configuration. In some embodiments, the angle of orientation between dots is from about 250 to about 60°. In some embodiments, the angle of orientation between dots is from about 300 to about 55°. In some embodiments, the angle of orientation between dots is from about 300 to about 50°. In some embodiments, the angle of orientation between dots is from about 35 to about 45°. In some embodiments, the angle of orientation between dots is about 25°. In some embodiments, the angle of orientation between dots is about 30°. In some embodiments, the angle of orientation between dots is about 35°. In some embodiments, the angle of orientation between dots is about 40°. In some embodiments, the angle of orientation between dots is about 45°. In some embodiments, the angle of orientation between dots is about 50°. In some embodiments, the angle of orientation between dots is about 55°. In some embodiments, the angle of orientation between dots is about 60°.

In some embodiments, the electrodes are in a substantially elongated configuration.

Figure 8:
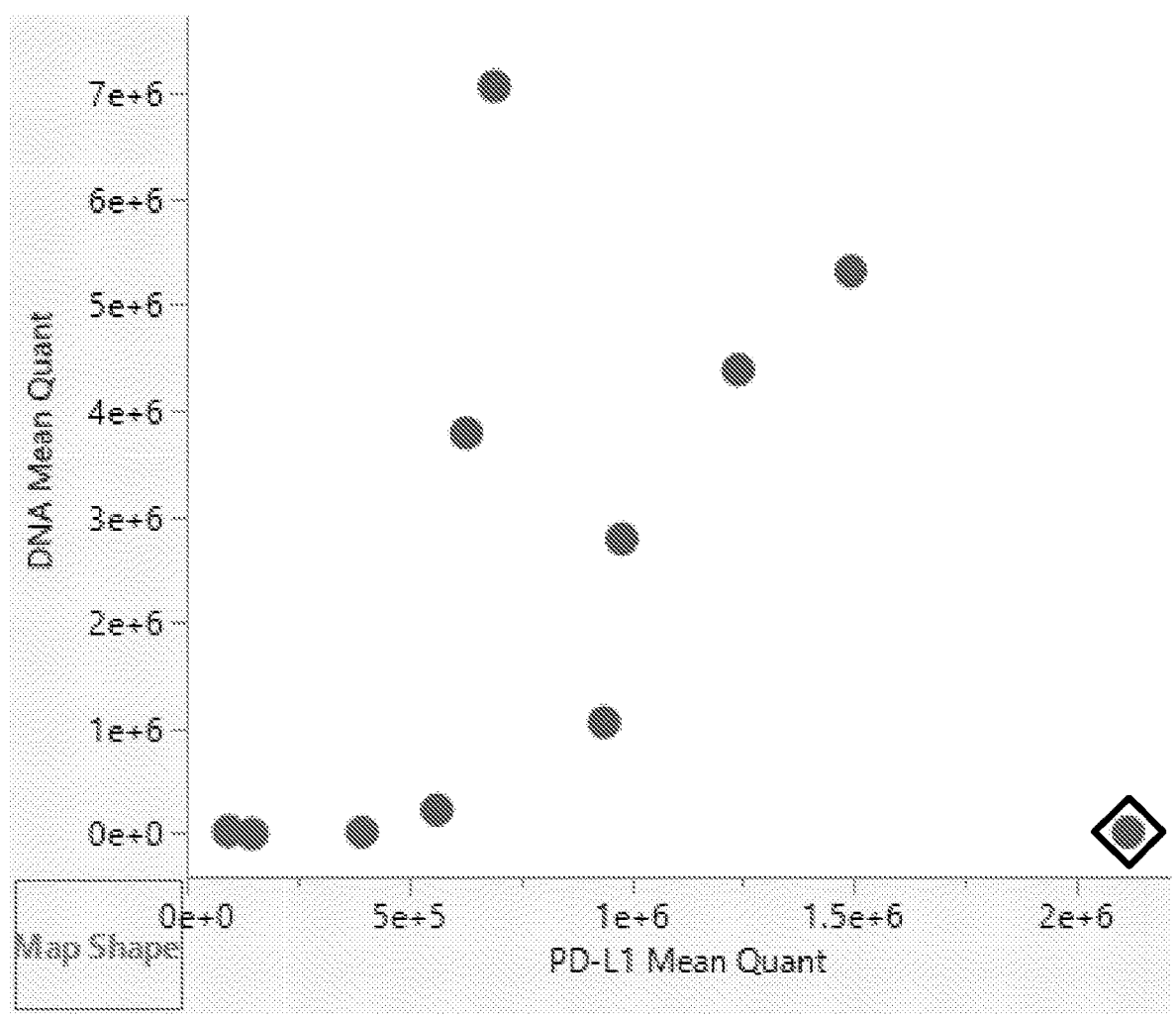
FIG. 8 shows a chart of the amounts of cfDNA and PD-L1 protein detected in a series of samples from healthy controls and patients with non-small cell lung cancer. The amounts were detected by running each samples over an electrode array, staining the cfDNA and PD-L1, imaging the resulting stained materials, and quantifying the amounts of cfDNA and PD-L1.

In some embodiments, the electrodes are in a configuration resembling wavy or nonlinear lines. In some embodiments, the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant. In some embodiments, the electrodes are strips resembling wavy lines, as depicted in FIG. 8. In some embodiments, the edge to edge distance between the electrodes is equidistant, or roughly equidistant throughout the wavy line configuration. In some embodiments, the use of wavy line electrodes, as disclosed herein, lead to an enhanced DEP field gradient.

In some embodiments, the electrodes disclosed herein are in a planar configuration. In some embodiments, the electrodes disclosed herein are in a non-planar configuration.

In some embodiments, the devices disclosed herein surface selectively captures biomolecules on its surface. For example, the devices disclosed herein may capture biomolecules, such as nucleic acids, by, for example, a. nucleic acid hybridization; b. antibody-antigen interactions; c. biotin-avidin interactions; d. ionic or electrostatic interactions; or e. any combination thereof. The devices disclosed herein, therefore, may incorporate a functionalized surface which includes capture molecules, such as complementary nucleic acid probes, antibodies or other protein captures capable of capturing biomolecules (such as nucleic acids), biotin or other anchoring captures capable of capturing complementary target molecules such as avidin, capture molecules capable of capturing biomolecules (such as nucleic acids) by ionic or electrostatic interactions, or any combination thereof.

In some embodiments, the surface is functionalized to minimize and/or inhibit nonspecific binding interactions by: a. polymers (e.g., polyethylene glycol PEG); b. ionic or electrostatic interactions; c. surfactants; or d. any combination thereof. In some embodiments, the methods disclosed herein include use of additives which reduce non-specific binding interactions by interfering in such interactions, such as Tween 20 and the like, bovine serum albumin, nonspecific immunoglobulins, etc.

In some embodiments, the device comprises a plurality of microelectrode devices oriented (a) flat side by side, (b) facing vertically, or (c) facing horizontally. In other embodiments, the electrodes are in a sandwiched configuration, e.g. stacked on top of each other in a vertical format.

Hydrogels

Overlaying electrode structures with one or more layers of materials can reduce the deleterious electrochemistry effects, including but not limited to electrolysis reactions, heating, and chaotic fluid movement that may occur on or near the electrodes, and still allow the effective separation of cells, bacteria, virus, nanoparticles, DNA, and other biomolecules to be carried out. In some embodiments, the materials layered over the electrode structures may be one or more porous layers. In other embodiments, the one or more porous layers is a polymer layer. In other embodiments, the one or more porous layers is a hydrogel.

In general, the hydrogel should have sufficient mechanical strength and be relatively chemically inert such that it will be able to endure the electrochemical effects at the electrode surface without disconfiguration or decomposition. In general, the hydrogel is sufficiently permeable to small aqueous ions, but keeps biomolecules away from the electrode surface.

In some embodiments, the hydrogel is a single layer, or coating.

In some embodiments, the hydrogel comprises a gradient of porosity, wherein the bottom of the hydrogel layer has greater porosity than the top of the hydrogel layer.

In some embodiments, the hydrogel comprises multiple layers or coatings. In some embodiments, the hydrogel comprises two coats. In some embodiments, the hydrogel comprises three coats. In some embodiments, the bottom (first) coating has greater porosity than subsequent coatings. In some embodiments, the top coat is has less porosity than the first coating. In some embodiments, the top coat has a mean pore diameter that functions as a size cut-off for particles of greater than 100 picometers in diameter.

In some embodiments, the hydrogel has a conductivity from about 0.001 S/m to about 10 S/m. In some embodiments, the hydrogel has a conductivity from about 0.01 S/m to about 10 S/m. In some embodiments, the hydrogel has a conductivity from about 0.1 S/m to about 10 S/m. In some embodiments, the hydrogel has a conductivity from about 1.0 S/m to about 10 S/m. In some embodiments, the hydrogel has a conductivity from about 0.01 S/m to about 5 S/m. In some embodiments, the hydrogel has a conductivity from about 0.01 S/m to about 4 S/m. In some embodiments, the hydrogel has a conductivity from about 0.01 S/m to about 3 S/m. In some embodiments, the hydrogel has a conductivity from about 0.01 S/m to about 2 S/m. In some embodiments, the hydrogel has a conductivity from about 0.1 S/m to about 5 S/m. In some embodiments, the hydrogel has a conductivity from about 0.1 S/m to about 4 S/m. In some embodiments, the hydrogel has a conductivity from about 0.1 S/m to about 3 S/m. In some embodiments, the hydrogel has a conductivity from about 0.1 S/m to about 2 S/m. In some embodiments, the hydrogel has a conductivity from about 0.1 S/m to about 1.5 S/m. In some embodiments, the hydrogel has a conductivity from about 0.1 S/m to about 1.0 S/m.

In some embodiments, the hydrogel has a conductivity of about 0.1 S/m. In some embodiments, the hydrogel has a conductivity of about 0.2 S/m. In some embodiments, the hydrogel has a conductivity of about 0.3 S/m. In some embodiments, the hydrogel has a conductivity of about 0.4 S/m. In some embodiments, the hydrogel has a conductivity of about 0.5 S/m. In some embodiments, the hydrogel has a conductivity of about 0.6 S/m. In some embodiments, the hydrogel has a conductivity of about 0.7 S/m. In some embodiments, the hydrogel has a conductivity of about 0.8 S/m. In some embodiments, the hydrogel has a conductivity of about 0.9 S/m. In some embodiments, the hydrogel has a conductivity of about 1.0 S/m.

In some embodiments, the hydrogel has a thickness from about 0.1 microns to about 10 microns. In some embodiments, the hydrogel has a thickness from about 0.1 microns to about 5 microns. In some embodiments, the hydrogel has a thickness from about 0.1 microns to about 4 microns. In some embodiments, the hydrogel has a thickness from about 0.1 microns to about 3 microns. In some embodiments, the hydrogel has a thickness from about 0.1 microns to about 2 microns. In some embodiments, the hydrogel has a thickness from about 1 micron to about 5 microns. In some embodiments, the hydrogel has a thickness from about 1 micron to about 4 microns. In some embodiments, the hydrogel has a thickness from about 1 micron to about 3 microns. In some embodiments, the hydrogel has a thickness from about 1 micron to about 2 microns. In some embodiments, the hydrogel has a thickness from about 0.5 microns to about 1 micron.

In some embodiments, the viscosity of a hydrogel solution prior to spin-coating ranges from about 0.5 cP to about 5 cP. In some embodiments, a single coating of hydrogel solution has a viscosity of between about 0.75 cP and 5 cP prior to spin-coating. In some embodiments, in a multi-coat hydrogel, the first hydrogel solution has a viscosity from about 0.5 cP to about 1.5 cP prior to spin coating. In some embodiments, the second hydrogel solution has a viscosity from about 1 cP to about 3 cP. The viscosity of the hydrogel solution is based on the polymers concentration (0.1%-10%) and polymers molecular weight (10,000 to 300,000) in the solvent and the starting viscosity of the solvent.

In some embodiments, the first hydrogel coating has a thickness between about 0.5 microns and 1 micron. In some embodiments, the first hydrogel coating has a thickness between about 0.5 microns and 0.75 microns. In some embodiments, the first hydrogel coating has a thickness between about 0.75 and 1 micron. In some embodiments, the second hydrogel coating has a thickness between about 0.2 microns and 0.5 microns. In some embodiments, the second hydrogel coating has a thickness between about 0.2 and 0.4 microns. In some embodiments, the second hydrogel coating has a thickness between about 0.2 and 0.3 microns. In some embodiments, the second hydrogel coating has a thickness between about 0.3 and 0.4 microns.

In some embodiments, the hydrogel comprises any suitable synthetic polymer forming a hydrogel. In general, any sufficiently hydrophilic and polymerizable molecule may be utilized in the production of a synthetic polymer hydrogel for use as disclosed herein. Polymerizable moieties in the monomers may include alkenyl moieties including but not limited to substituted or unsubstituted α,β,unsaturated carbonyls wherein the double bond is directly attached to a carbon which is double bonded to an oxygen and single bonded to another oxygen, nitrogen, sulfur, halogen, or carbon; vinyl, wherein the double bond is singly bonded to an oxygen, nitrogen, halogen, phosphorus or sulfur; allyl, wherein the double bond is singly bonded to a carbon which is bonded to an oxygen, nitrogen, halogen, phosphorus or sulfur; homoallyl, wherein the double bond is singly bonded to a carbon which is singly bonded to another carbon which is then singly bonded to an oxygen, nitrogen, halogen, phosphorus or sulfur; alkynyl moieties wherein a triple bond exists between two carbon atoms. In some embodiments, acryloyl or acrylamido monomers such as acrylates, methacrylates, acrylamides, methacrylamides, etc., are useful for formation of hydrogels as disclosed herein. More preferred acrylamido monomers include acrylamides, N-substituted acrylamides, N-substituted methacrylamides, and methacrylamide. In some embodiments, a hydrogel comprises polymers such as epoxide-based polymers, vinyl-based polymers, allyl-based polymers, homoallyl-based polymers, cyclic anhydride-based polymers, ester-based polymers, ether-based polymers, alkylene-glycol based polymers (e.g., polypropylene glycol), and the like.

In some embodiments, the hydrogel comprises polyhydroxyethylmethacrylate (pHEMA), cellulose acetate, cellulose acetate phthalate, cellulose acetate butyrate, or any appropriate acrylamide or vinyl-based polymer, or a derivative thereof.

In some embodiments, the hydrogel is applied by vapor deposition.

In some embodiments, the hydrogel is polymerized via atom-transfer radical-polymerization via (ATRP).

In some embodiments, the hydrogel is polymerized via reversible addition-fragmentation chain-transfer (RAFT) polymerization.

In some embodiments, additives are added to a hydrogel to increase conductivity of the gel. In some embodiments, hydrogel additives are conductive polymers (e.g., PEDOT: PSS), salts (e.g., copper chloride), metals (e.g., gold), plasticizers (e.g., PEG200, PEG 400, or PEG 600), or co-solvents.

In some embodiments, the hydrogel also comprises compounds or materials which help maintain the stability of the DNA hybrids, including, but not limited to histidine, histidine peptides, polyhistidine, lysine, lysine peptides, and other cationic compounds or substances.

Dielectrophoretic Fields

In some embodiments, the methods, devices and systems described herein provide a mechanism to collect, separate, and/or isolate cells, particles, and/or molecules (such as nucleic acid) from a fluid material (which optionally contains other materials, such as contaminants, residual cellular material, or the like).

In some embodiments, an AC electrokinetic field is generated to collect, separate or isolate biomolecules, such as nucleic acids. In some embodiments, the AC electrokinetic field is a dielectrophoretic field. Accordingly, in some embodiments dielectrophoresis (DEP) is utilized in various steps of the methods described herein.

In some embodiments, the devices and systems described herein are capable of generating DEP fields, and the like. In specific embodiments, DEP is used to concentrate cells and/or nucleic acids (e.g., concurrently or at different times). In certain embodiments, methods described herein further comprise energizing the array of electrodes so as to produce the first, second, and any further optional DEP fields. In some embodiments, the devices and systems described herein are capable of being energized so as to produce the first, second, and any further optional DEP fields.

DEP is a phenomenon in which a force is exerted on a dielectric particle when it is subjected to a non-uniform electric field. Depending on the step of the methods described herein, aspects of the devices and systems described herein, and the like, the dielectric particle in various embodiments herein is a biological cell and/or a molecule, such as a nucleic acid molecule. Different steps of the methods described herein or aspects of the devices or systems described herein may be utilized to isolate and separate different components, such as intact cells or other particular material; further, different field regions of the DEP field may be used in different steps of the methods or aspects of the devices and systems described herein. This dielectrophoretic force does not require the particle to be charged. In some instances, the strength of the force depends on the medium and the specific particles' electrical properties, on the particles' shape and size, as well as on the frequency of the electric field. In some instances, fields of a particular frequency selectivity manipulate particles. In certain aspects described herein, these processes allow for the separation of cells and/or smaller particles (such as molecules, including nucleic acid molecules) from other components (e.g., in a fluid medium) or each other.

In various embodiments provided herein, a method or device described herein comprises producing a plurality of DEP field regions. For example, a method or device comprises a first DEP field region and a second DEP field region with the array. In various embodiments provided herein, a device or system described herein is capable of producing a first DEP field region and a second DEP field region with the array. In some instances, the first and second field regions are part of a single field (e.g., the first and second regions are present at the same time, but are found at different locations within the device and/or upon the array). In some embodiments, the first and second field regions are different fields (e.g. the first region is created by energizing the electrodes at a first time, and the second region is created by energizing the electrodes a second time). In specific aspects, the first DEP field region is suitable for concentrating or isolating cells (e.g., into a low field DEP region). In some embodiments, the second DEP field region is suitable for concentrating smaller particles, such as molecules (e.g., nucleic acid, including cell-free nucleic acid), for example into a high field DEP region. In some instances, a method described herein optionally excludes use of either the first or second DEP field region.

As is described below, in some instances, the first DEP field is suitable for concentrating or isolating nucleic acids, including cell-free nucleic acids, above a size, below a size, or within a range of sizes. In some instances, the second DEP field is suitable for concentrating or isolating nucleic acids, including cell-free nucleic acids, above a size, below a size, or within a range of sizes. The first and second DEP fields can be configured to concentrate or isolate the same or different size nucleic acids. As such, the methods and devices disclosed herein can be used to assess nucleic acids of a variety of different sizes.

Also described herein are embodiments comprising three or more DEP field regions, wherein each of the field regions can be configured to operate in the same or different many as at least one other field regions. Thus, the embodiments can concentrate or isolate a variety of materials in the biological samples based upon a variety of properties. For example, a first DEP field region can be configured to isolate cells, a second DEP field region can be configured to isolate or concentrate cell-free DNA above 500 bp, a third DEP field region can be configured to isolate or concentrate cell-free DNA between 300 bp and 500 bp, and a fourth DEP field region can be configured to isolate or concentrate cell-free DNA below 300 bp. Some of such embodiments can include quantitating the amount of DNA isolated or concentrated within each field region.

In some embodiments, the first DEP field region is in the same chamber of a device as disclosed herein as the second DEP field region. In some embodiments, the first DEP field region and the second DEP field region occupy the same area of the array of electrodes.

In some embodiments, the first DEP field region is in a separate chamber of a device as disclosed herein, or a separate device entirely, from the second DEP field region.

First DEP Field Region

In some aspects, e.g., high conductance buffers (>100 mS/m), the method described herein comprises applying a fluid comprising cells or other particulate material to a device comprising an array of electrodes, and, thereby, concentrating the cells in a first DEP field region. In some aspects, the devices and systems described herein are capable of applying a fluid comprising cells or other particulate material to the device comprising an array of electrodes, and, thereby, concentrating the cells in a first DEP field region. Subsequent or concurrent second, or optional third and fourth DEP regions, may collect or isolate other fluid components, including biomolecules, such as nucleic acids.

The first DEP field region may be any field region suitable for concentrating cells from a fluid. For this application, the cells are generally concentrated near the array of electrodes. In some embodiments, the first DEP field region is a dielectrophoretic low field region. In some embodiments, the first DEP field region is a dielectrophoretic high field region. In some aspects, e.g. low conductance buffers (<100 mS/m), the method described herein comprises applying a fluid comprising cells to a device comprising an array of electrodes, and, thereby, concentrating the cells or other particulate material in a first DEP field region.

In some aspects, the devices and systems described herein are capable of applying a fluid comprising cells or other particulate material to the device comprising an array of electrodes, and concentrating the cells in a first DEP field region. In various embodiments, the first DEP field region may be any field region suitable for concentrating cells from a fluid. In some embodiments, the cells are concentrated on the array of electrodes. In some embodiments, the cells are captured in a dielectrophoretic high field region. In some embodiments, the cells are captured in a dielectrophoretic low-field region. High versus low field capture is generally dependent on the conductivity of the fluid, wherein generally, the crossover point is between about 300-500 mS/m. In some embodiments, the first DEP field region is a dielectrophoretic low field region performed in fluid conductivity of greater than about 300 mS/m. In some embodiments, the first DEP field region is a dielectrophoretic low field region performed in fluid conductivity of less than about 300 mS/m. In some embodiments, the first DEP field region is a dielectrophoretic high field region performed in fluid conductivity of greater than about 300 mS/m. In some embodiments, the first DEP field region is a dielectrophoretic high field region performed in fluid conductivity of less than about 300 mS/m. In some embodiments, the first DEP field region is a dielectrophoretic low field region performed in fluid conductivity of greater than about 500 mS/m. In some embodiments, the first DEP field region is a dielectrophoretic low field region performed in fluid conductivity of less than about 500 mS/m. In some embodiments, the first DEP field region is a dielectrophoretic high field region performed in fluid conductivity of greater than about 500 mS/m. In some embodiments, the first DEP field region is a dielectrophoretic high field region performed in fluid conductivity of less than about 500 mS/m.

In some embodiments, the first dielectrophoretic field region is produced by an alternating current. The alternating current has any amperage, voltage, frequency, and the like suitable for concentrating cells. In some embodiments, the first dielectrophoretic field region is produced using an alternating current having an amperage of 0.1 micro Amperes-10 Amperes; a voltage of 1-50 Volts peak to peak; and/or a frequency of 1-10,000,000 Hz. In some embodiments, the first DEP field region is produced using an alternating current having a voltage of 5-25 volts peak to peak. In some embodiments, the first DEP field region is produced using an alternating current having a frequency of from 3-15 kHz. In some embodiments, the first DEP field region is produced using an alternating current having an amperage of 1 milliamp to 1 amp. In some embodiments, the first DEP field region is produced using an alternating current having an amperage of 0.1 micro Amperes-1 Ampere. In some embodiments, the first DEP field region is produced using an alternating current having an amperage of 1 micro Amperes-1 Ampere. In some embodiments, the first DEP field region is produced using an alternating current having an amperage of 100 micro Amperes-1 Ampere. In some embodiments, the first DEP field region is produced using an alternating current having an amperage of 500 micro Amperes-500 milli Amperes. In some embodiments, the first DEP field region is produced using an alternating current having a voltage of 1-25 Volts peak to peak. In some embodiments, the first DEP field region is produced using an alternating current having a voltage of 1-10 Volts peak to peak. In some embodiments, the first DEP field region is produced using an alternating current having a voltage of 25-50 Volts peak to peak. In some embodiments, the first DEP field region is produced using a frequency of from 10-1,000,000 Hz. In some embodiments, the first DEP field region is produced using a frequency of from 100-100,000 Hz. In some embodiments, the first DEP field region is produced using a frequency of from 100-10,000 Hz. In some embodiments, the first DEP field region is produced using a frequency of from 10,000-100,000 Hz. In some embodiments, the first DEP field region is produced using a frequency of from 100,000-1,000,000 Hz.

In some embodiments, the first dielectrophoretic field region is produced by a direct current. The direct current has any amperage, voltage, frequency, and the like suitable for concentrating cells. In some embodiments, the first dielectrophoretic field region is produced using a direct current having an amperage of 0.1 micro Amperes-1 Amperes; a voltage of 10 milli Volts-10 Volts; and/or a pulse width of 1 milliseconds-1000 seconds and a pulse frequency of 0.001-1000 Hz. In some embodiments, the first DEP field region is produced using a direct current having an amperage of 1 micro Amperes-1 Amperes. In some embodiments, the first DEP field region is produced using a direct current having an amperage of 100 micro Amperes-500 milli Amperes. In some embodiments, the first DEP field region is produced using a direct current having an amperage of 1 milli Amperes-1 Amperes. In some embodiments, the first DEP field region is produced using a direct current having an amperage of 1 micro Amperes-1 milli Amperes. In some embodiments, the first DEP field region is produced using a direct current having a pulse width of 500 milliseconds-500 seconds. In some embodiments, the first DEP field region is produced using a direct current having a pulse width of 500 milliseconds-100 seconds. In some embodiments, the first DEP field region is produced using a direct current having a pulse width of 1 second-1000 seconds. In some embodiments, the first DEP field region is produced using a direct current having a pulse width of 500 milliseconds-1 second. In some embodiments, the first DEP field region is produced using a pulse frequency of 0.01-1000 Hz. In some embodiments, the first DEP field region is produced using a pulse frequency of 0.1-100 Hz. In some embodiments, the first DEP field region is produced using a pulse frequency of 1-100 Hz. In some embodiments, the first DEP field region is produced using a pulse frequency of 100-1000 Hz.

In some embodiments, the fluid comprises a mixture of cell types. For example, blood comprises red blood cells and white blood cells. Environmental samples comprise many types of cells and other particulate material over a wide range of concentrations. In some embodiments, one cell type (or any number of cell types less than the total number of cell types comprising the sample) is preferentially concentrated in the first DEP field. Without limitation, this embodiment is beneficial for focusing the nucleic acid isolation procedure on a particular environmental contaminant, such as a fecal coliform bacterium, whereby DNA sequencing may be used to identify the source of the contaminant. In another non-limiting example, the first DEP field is operated in a manner that specifically concentrates viruses and not cells (e.g., in a fluid with conductivity of greater than 300 mS/m, viruses concentrate in a DEP high field region, while larger cells will concentrate in a DEP low field region).

In some embodiments, a method, device or system described herein is suitable for isolating or separating specific cell types. In some embodiments, the DEP field of the method, device or system is specifically tuned to allow for the separation or concentration of a specific type of cell into a field region of the DEP field. In some embodiments, a method, device or system described herein provides more than one field region wherein more than one type of cell is isolated or concentrated. In some embodiments, a method, device, or system described herein is tunable so as to allow isolation or concentration of different types of cells within the DEP field regions thereof. In some embodiments, a method provided herein further comprises tuning the DEP field. In some embodiments, a device or system provided herein is capable of having the DEP field tuned. In some instances, such tuning may be in providing a DEP particularly suited for the desired purpose. For example, modifications in the array, the energy, or another parameter are optionally utilized to tune the DEP field. Tuning parameters for finer resolution include electrode diameter, edge to edge distance between electrodes, voltage, frequency, fluid conductivity and hydrogel composition.

In some embodiments, the first DEP field region comprises the entirety of an array of electrodes. In some embodiments, the first DEP field region comprises a portion of an array of electrodes. In some embodiments, the first DEP field region comprises about 90%, about 80%, about 70%, about 60%, about 50%, about 40%, about 30%, about 25%, about 20%, or about 10% of an array of electrodes. In some embodiments, the first DEP field region comprises about a third of an array of electrodes.

Second DEP Field Region

The second DEP field region can be configured to be the same or different than the first DEP field region. As described above, the second DEP field region can be configured to isolate or concentrate the same or different macromolecules and cellular components as the first DEP field region. These include macromolecules and cellular components include DNA, including cell-free DNA and DNA fragments, RNA, nucleosomes, exosomes, extracellular vesicles, proteins, cell membrane fragments, mitochondria or cellular vesicles.

In some aspects, the first DEP field region and second DEP field region can be configured to isolate or concentrate different subsets of the same type of macromolecule or cellular component. For example, in some embodiments, the first DEP field region can be configured to isolate or concentrate a first macromolecule or first cellular component of a first size or first range of sizes and the second DEP field region can be configured to isolate or concentrate the first macromolecule or first cellular component of a second size or second range of sizes. In one example, the first DEP field region can be configured to isolate or concentrate cell-free DNA between 300-500 bp and the second DEP field region can be configured to isolate or concentrate cell-free DNA smaller than 300 bp. Thus, the plurality of field regions can be used to discriminate between subsets of the same type of macromolecule or cellular components. In an exemplary advantage, use of a plurality of field regions can also allow for the quantification of one or more subsets of the same type of macromolecule or cellular component.

In one aspect, following lysis of the cells (as provided below), the methods described herein involve concentrating the nucleic acid in a second DEP field region. In another aspect, the devices and systems described herein are capable of concentrating the nucleic acid in a second DEP field region. In some embodiments, the second DEP field region is any field region suitable for concentrating nucleic acids. In some embodiments, the nucleic acids are concentrated on the array of electrodes. In some embodiments, the second DEP field region is a dielectrophoretic high field region. The second DEP field region is, optionally, the same as the first DEP field region.

In some embodiments, the second dielectrophoretic field region is produced by an alternating current. In some embodiments, the alternating current has any amperage, voltage, frequency, and the like suitable for concentrating nucleic acids. In some embodiments, the second dielectrophoretic field region is produced using an alternating current having an amperage of 0.1 micro Amperes-10 Amperes; a voltage of 1-50 Volts peak to peak; and/or a frequency of 1-10,000,000 Hz. In some embodiments, the second DEP field region is produced using an alternating current having an amperage of 0.1 micro Amperes-1 Ampere. In some embodiments, the second DEP field region is produced using an alternating current having an amperage of 1 micro Amperes-1 Ampere. In some embodiments, the second DEP field region is produced using an alternating current having an amperage of 100 micro Amperes-1 Ampere. In some embodiments, the second DEP field region is produced using an alternating current having an amperage of 500 micro Amperes-500 milli Amperes. In some embodiments, the second DEP field region is produced using an alternating current having a voltage of 1-25 Volts peak to peak. In some embodiments, the second DEP field region is produced using an alternating current having a voltage of 1-10 Volts peak to peak. In some embodiments, the second DEP field region is produced using an alternating current having a voltage of 25-50 Volts peak to peak. In some embodiments, the second DEP field region is produced using a frequency of from 10-1,000,000 Hz. In some embodiments, the second DEP field region is produced using a frequency of from 100-100,000 Hz. In some embodiments, the second DEP field region is produced using a frequency of from 100-10,000 Hz. In some embodiments, the second DEP field region is produced using a frequency of from 10,000-100,000 Hz. In some embodiments, the second DEP field region is produced using a frequency of from 100,000-1,000,000 Hz.

In some embodiments, the second dielectrophoretic field region is produced by a direct current. In some embodiments, the direct current has any amperage, voltage, frequency, and the like suitable for concentrating nucleic acids. In some embodiments, the second dielectrophoretic field region is produced using a direct current having an amperage of 0.1 micro Amperes-1 Amperes; a voltage of 10 milli Volts-10 Volts; and/or a pulse width of 1 milliseconds-1000 seconds and a pulse frequency of 0.001-1000 Hz. In some embodiments, the second DEP field region is produced using an alternating current having a voltage of 5-25 volts peak to peak. In some embodiments, the second DEP field region is produced using an alternating current having a frequency of from 3-15 kHz. In some embodiments, the second DEP field region is produced using an alternating current having an amperage of 1 milliamp to 1 amp. In some embodiments, the second DEP field region is produced using a direct current having an amperage of 1 micro Amperes-1 Amperes. In some embodiments, the second DEP field region is produced using a direct current having an amperage of 100 micro Amperes-500 milli Amperes. In some embodiments, the second DEP field region is produced using a direct current having an amperage of 1 milli Amperes-1 Amperes. In some embodiments, the second DEP field region is produced using a direct current having an amperage of 1 micro Amperes-1 milli Amperes. In some embodiments, the second DEP field region is produced using a direct current having a pulse width of 500 milliseconds-500 seconds. In some embodiments, the second DEP field region is produced using a direct current having a pulse width of 500 milliseconds-100 seconds. In some embodiments, the second DEP field region is produced using a direct current having a pulse width of 1 second-1000 seconds. In some embodiments, the second DEP field region is produced using a direct current having a pulse width of 500 milliseconds-1 second. In some embodiments, the second DEP field region is produced using a pulse frequency of 0.01-1000 Hz. In some embodiments, the second DEP field region is produced using a pulse frequency of 0.1-100 Hz. In some embodiments, the second DEP field region is produced using a pulse frequency of 1-100 Hz. In some embodiments, the second DEP field region is produced using a pulse frequency of 100-1000 Hz.

In some embodiments, the second DEP field region comprises the entirety of an array of electrodes. In some embodiments, the second DEP field region comprises a portion of an array of electrodes. In some embodiments, the second DEP field region comprises about 90%, about 80%, about 70%, about 60%, about 50%, about 40%, about 30%, about 25%, about 20%, or about 10% of an array of electrodes. In some embodiments, the second DEP field region comprises about a third of an array of electrodes.

Isolating Nucleic Acids

In one aspect, described herein is a method for isolating a nucleic acid from a fluid. In some embodiments, the nucleic acids are cell-free nucleic acids. In some embodiments, disclosed herein is method for isolating a cell-free nucleic acid from a fluid, the method comprising: a. applying the fluid to a device, the device comprising an array of electrodes; b. concentrating a plurality of cellular materials in a first AC electrokinetic (e.g., dielectrophoretic) field region; c. isolating nucleic acid in a second AC electrokinetic (e.g., dielectrophoretic) field region; and d. flushing the cellular materials away. In some instances, residual cellular material is concentrated near the low field region. In some embodiments, the residual material is washed from the device and/or washed from the nucleic acids. In some embodiments, the nucleic acid is concentrated in the second AC electrokinetic field region.

Figure 3:
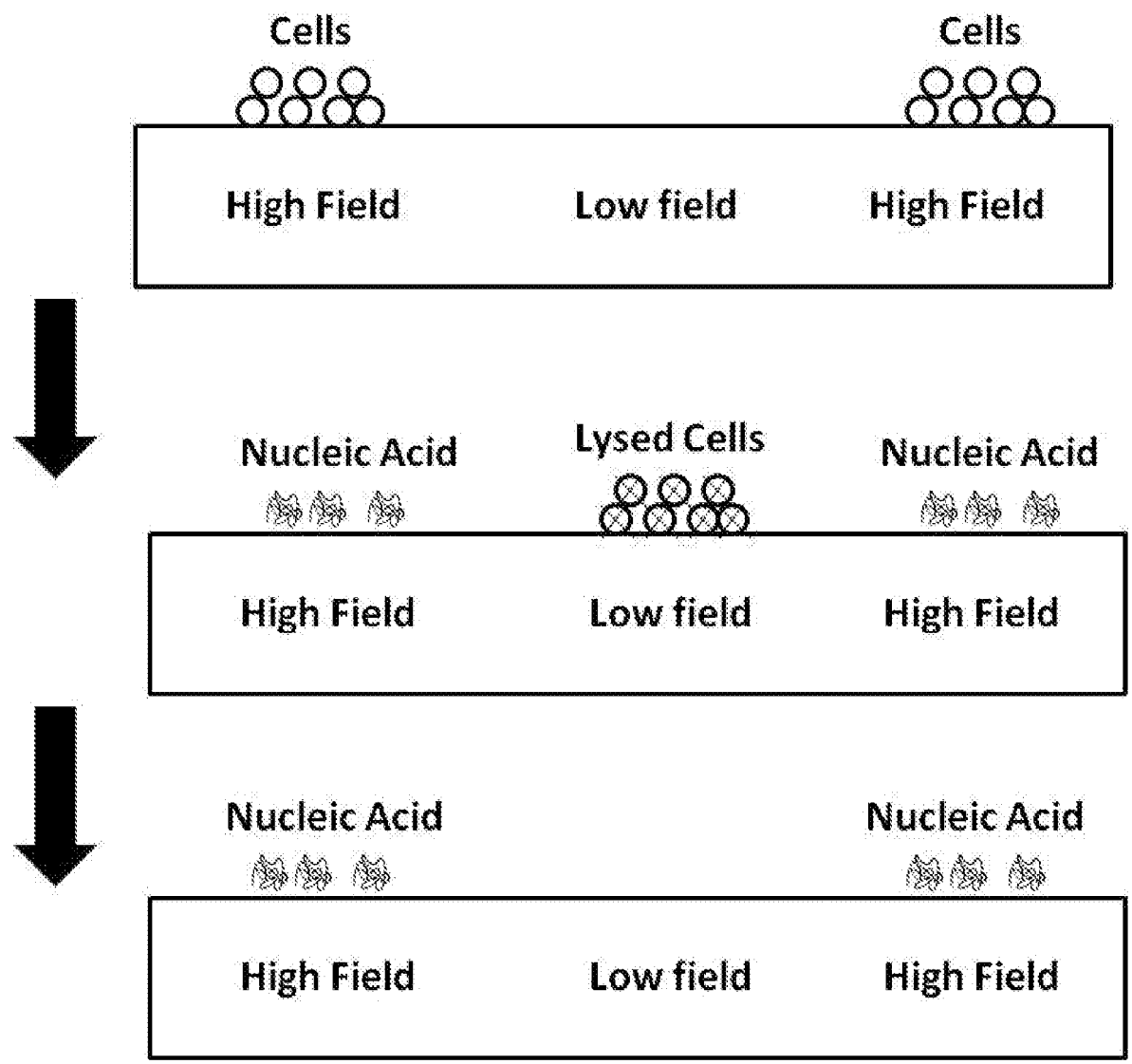
FIG. 3 shows an exemplary method for isolating nucleic acids from cells.

In some embodiments, the nucleic acids are initially inside the cells. As seen in FIG. 3, the method comprises concentrating the cells near a high field region in some instances. In some embodiments, disclosed herein is method for isolating a nucleic acid from a fluid comprising cells, the method comprising: a. applying the fluid to a device, the device comprising an array of electrodes; b. concentrating a plurality of cells in a first AC electrokinetic (e.g., dielectrophoretic) field region; c. isolating nucleic acid in a second AC electrokinetic (e.g., dielectrophoretic) field region; and d. flushing cells away. In some instances, the cells are lysed in the high field region. Following lysis, the nucleic acids remain in the high field region and/or are concentrated in the high field region. In some instances, residual cellular material is concentrated near the low field region. In some embodiments, the residual material is washed from the device and/or washed from the nucleic acids. In some embodiments, the nucleic acid is concentrated in the second AC electrokinetic field region.

Figure 4:
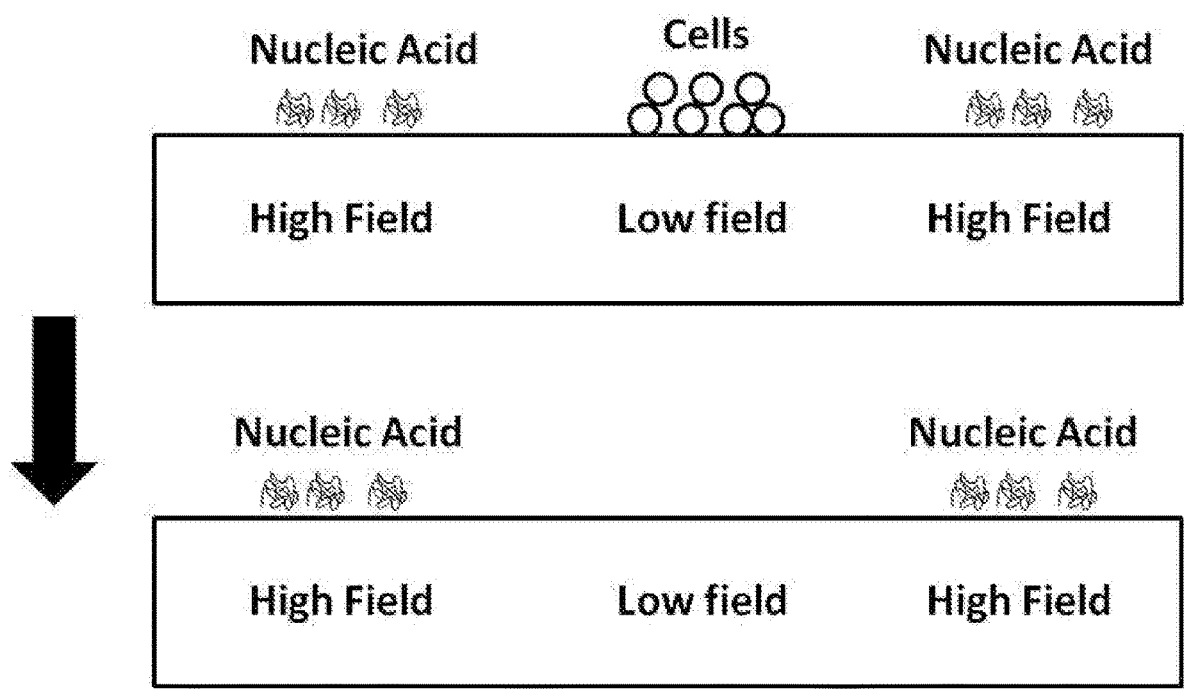
FIG. 4 shows an exemplary method for isolating extracellular nucleic acids from a fluid comprising cells.
Figure 5:
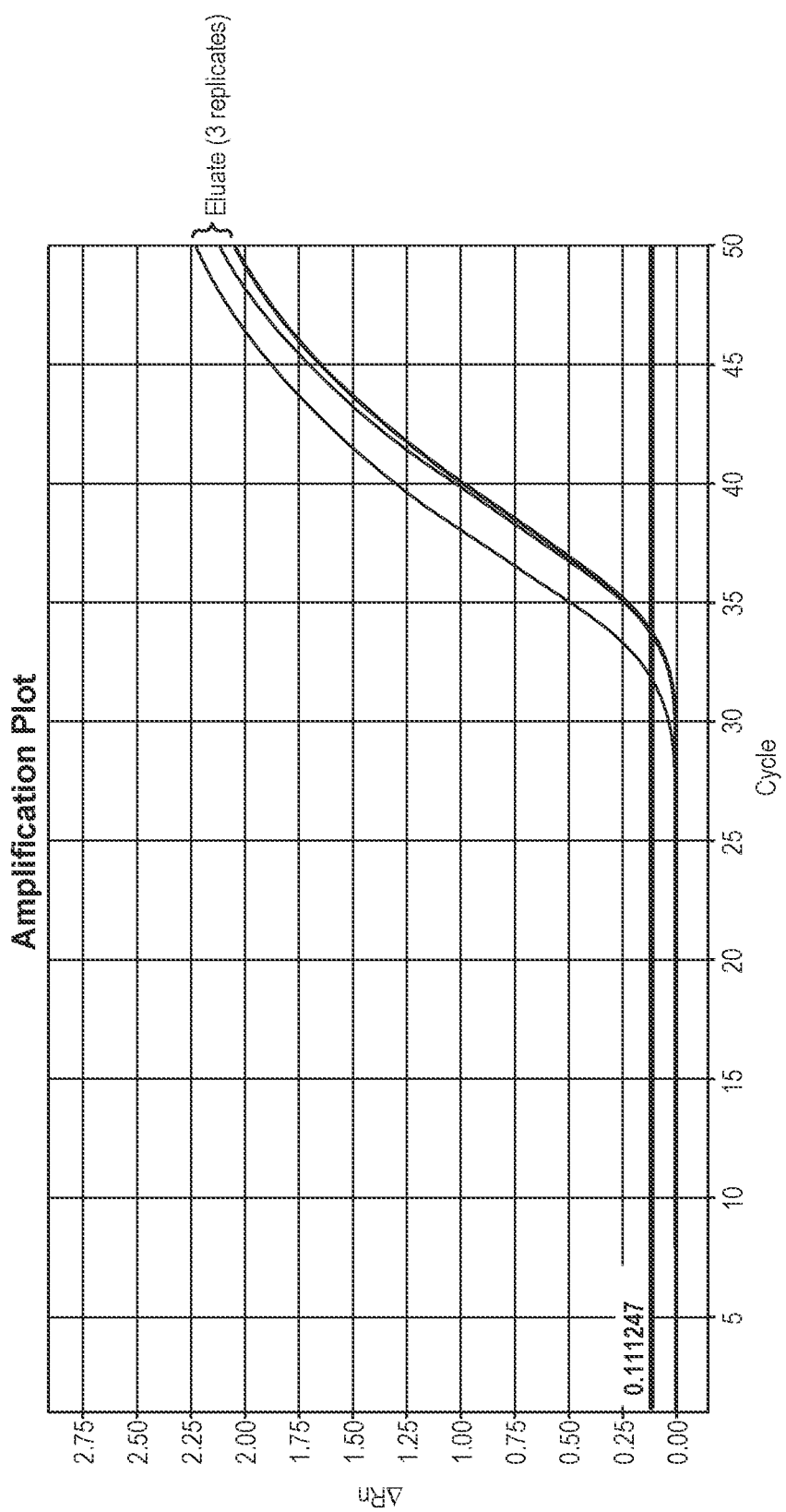
FIG. 5 shows PCR amplification of DNA eluted from a microelectrode array.
Figure 6:
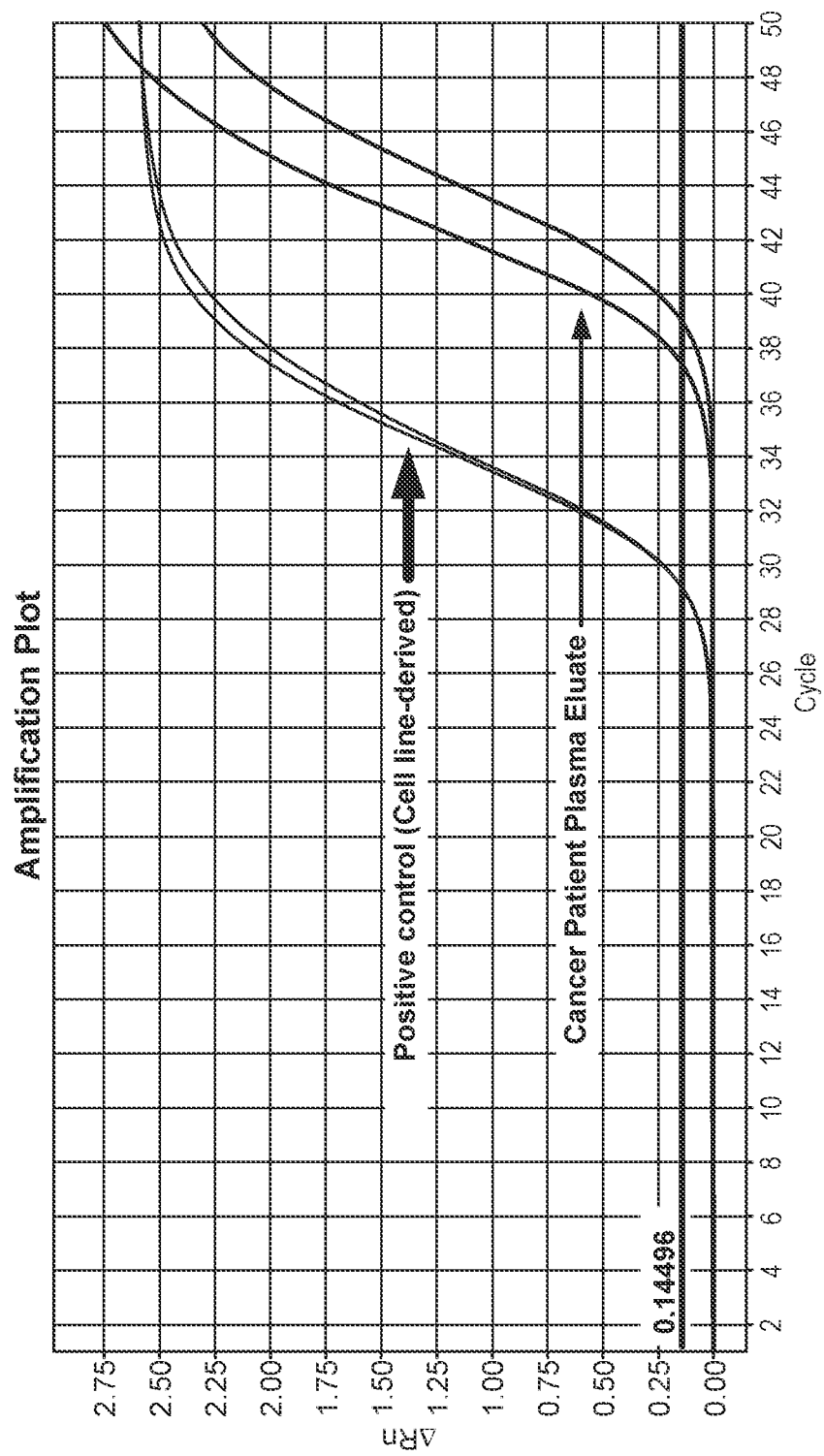
FIG. 6 shows RT-PCR amplification of RNA eluted from a microelectrode array.

In one aspect, described herein is a method for isolating a nucleic acid from a fluid comprising cells or other particulate material. In some embodiments, the nucleic acids are not inside the cells (e.g., cell-free DNA in fluid). In some embodiments, disclosed herein is a method for isolating a nucleic acid from a fluid comprising cells or other particulate material, the method comprising: a. applying the fluid to a device, the device comprising an array of electrodes; b. concentrating a plurality of cells in a first AC electrokinetic (e.g., dielectrophoretic) field region; c. isolating nucleic acid in a second AC electrokinetic (e.g., dielectrophoretic) field region; and d. flushing cells away. In some embodiments, the method further comprises degrading residual proteins after flushing cells away. FIG. 4 shows an exemplary method for isolating extra-cellular nucleic acids from a fluid comprising cells. In some embodiments, cells are concentrated on or near a low field region and nucleic acids are concentrated on or near a high field region. In some instances, the cells are washed from the device and/or washed from the nucleic acids.

In one aspect, the methods, systems and devices described herein isolate nucleic acid from a fluid comprising cells or other particulate material. In one aspect, dielectrophoresis is used to concentrate cells. In some embodiments, the fluid is a liquid, optionally water or an aqueous solution or dispersion. In some embodiments, the fluid is any suitable fluid including a bodily fluid. Exemplary bodily fluids include blood, serum, plasma, bile, milk, cerebrospinal fluid, gastric juice, ejaculate, mucus, peritoneal fluid, saliva, sweat, tears, urine, and the like. In some embodiments, nucleic acids are isolated from bodily fluids using the methods, systems or devices described herein as part of a medical therapeutic or diagnostic procedure, device or system. In some embodiments, the fluid is tissues and/or cells solubilized and/or dispersed in a fluid. For example, the tissue can be a cancerous tumor from which nucleic acid can be isolated using the methods, devices or systems described herein.

In some embodiments, the fluid is water.

In some embodiments, the fluid may also comprise other particulate material. Such particulate material may be, for example, inclusion bodies (e.g., ceroids or Mallory bodies), cellular casts (e.g., granular casts, hyaline casts, cellular casts, waxy casts and pseudo casts), Pick's bodies, Lewy bodies, fibrillary tangles, fibril formations, cellular debris and other particulate material. In some embodiments, particulate material is an aggregated protein (e.g., beta-amyloid).

The fluid can have any conductivity including a high or low conductivity. In some embodiments, the conductivity is between about 1 µS/m to about 10 mS/m. In some embodiments, the conductivity is between about 10 µS/m to about 10 mS/m. In other embodiments, the conductivity is between about 50 µS/m to about 10 mS/m. In yet other embodiments, the conductivity is between about 100 µS/m to about 10 mS/m, between about 100 µS/m to about 8 mS/m, between about 100 µS/m to about 6 mS/m, between about 100 µS/m to about 5 mS/m, between about 100 µS/m to about 4 mS/m, between about 100 µS/m to about 3 mS/m, between about 100 µS/m to about 2 mS/m, or between about 100 µS/m to about 1 mS/m.

In some embodiments, the conductivity is about 1 µS/m. In some embodiments, the conductivity is about 10 µS/m. In some embodiments, the conductivity is about 100 µS/m. In some embodiments, the conductivity is about 1 mS/m. In other embodiments, the conductivity is about 2 mS/m. In some embodiments, the conductivity is about 3 mS/m. In yet other embodiments, the conductivity is about 4 mS/m. In some embodiments, the conductivity is about 5 mS/m. In some embodiments, the conductivity is about 10 mS/m. In still other embodiments, the conductivity is about 100 mS/m. In some embodiments, the conductivity is about 1 S/m. In other embodiments, the conductivity is about 10 S/m.

In some embodiments, the conductivity is at least 1 µS/m. In yet other embodiments, the conductivity is at least 10 µS/m. In some embodiments, the conductivity is at least 100 µS/m. In some embodiments, the conductivity is at least 1 mS/m. In additional embodiments, the conductivity is at least 10 mS/m. In yet other embodiments, the conductivity is at least 100 mS/m. In some embodiments, the conductivity is at least 1 S/m. In some embodiments, the conductivity is at least 10 S/m. In some embodiments, the conductivity is at most 1 µS/m. In some embodiments, the conductivity is at most 10 µS/m. In other embodiments, the conductivity is at most 100 µS/m. In some embodiments, the conductivity is at most 1 mS/m. In some embodiments, the conductivity is at most 10 mS/m. In some embodiments, the conductivity is at most 100 mS/m. In yet other embodiments, the conductivity is at most 1 S/m. In some embodiments, the conductivity is at most 10 S/m.

In some embodiments, the fluid is a small volume of liquid including less than 10 ml. In some embodiments, the fluid is less than 8 ml. In some embodiments, the fluid is less than 5 ml. In some embodiments, the fluid is less than 2 ml. In some embodiments, the fluid is less than 1 ml. In some embodiments, the fluid is less than 500 µl. In some embodiments, the fluid is less than 200 µl. In some embodiments, the fluid is less than 100 µl. In some embodiments, the fluid is less than 50 µl. In some embodiments, the fluid is less than 10 µl. In some embodiments, the fluid is less than 5 µl. In some embodiments, the fluid is less than 1 µl.

In some embodiments, the quantity of fluid applied to the device or used in the method comprises less than about 100,000,000 cells. In some embodiments, the fluid comprises less than about 10,000,000 cells. In some embodiments, the fluid comprises less than about 1,000,000 cells. In some embodiments, the fluid comprises less than about 100,000 cells. In some embodiments, the fluid comprises less than about 10,000 cells. In some embodiments, the fluid comprises less than about 1,000 cells. In some embodiments, the fluid is cell-free.

In some embodiments, isolation of nucleic acid from a fluid comprising cells or other particulate material with the devices, systems and methods described herein takes less than about 30 minutes, less than about 20 minutes, less than about 15 minutes, less than about 10 minutes, less than about 5 minutes or less than about 1 minute. In other embodiments, isolation of nucleic acid from a fluid comprising cells or other particulate material with the devices, systems and methods described herein takes not more than 30 minutes, not more than about 20 minutes, not more than about 15 minutes, not more than about 10 minutes, not more than about 5 minutes, not more than about 2 minutes or not more than about 1 minute. In additional embodiments, isolation of nucleic acid from a fluid comprising cells or other particulate material with the devices, systems and methods described herein takes less than about 15 minutes, preferably less than about 10 minutes or less than about 5 minutes.

In some instances, extra-cellular DNA, cell-free DNA fragments, or other nucleic acids (outside cells) are isolated from a fluid comprising cells of other particulate material. In some embodiments, the fluid comprises cells. In some embodiments, the fluid does not comprise cells.

Cell Lysis

In one aspect, following concentrating the cells in a first dielectrophoretic field region, the method involves freeing nucleic acids from the cells. In another aspect, the devices and systems described herein are capable of freeing nucleic acids from the cells. In some embodiments, the nucleic acids are freed from the cells in the first DEP field region.

In some embodiments, the methods described herein free nucleic acids from a plurality of cells by lysing the cells. In some embodiments, the devices and systems described herein are capable of freeing nucleic acids from a plurality of cells by lysing the cells. One method of cell lysis involves applying a direct current to the cells after isolation of the cells on the array. The direct current has any suitable amperage, voltage, and the like suitable for lysing cells. In some embodiments, the current has a voltage of about 1 Volt to about 500 Volts. In some embodiments, the current has a voltage of about 10 Volts to about 500 Volts. In other embodiments, the current has a voltage of about 10 Volts to about 250 Volts. In still other embodiments, the current has a voltage of about 50 Volts to about 150 Volts. Voltage is generally the driver of cell lysis, as high electric fields result in failed membrane integrity.

In some embodiments, the direct current used for lysis comprises one or more pulses having any duration, frequency, and the like suitable for lysing cells. In some embodiments, a voltage of about 100 volts is applied for about 1 millisecond to lyse cells. In some embodiments, the voltage of about 100 volts is applied 2 or 3 times over the source of a second.

In some embodiments, the frequency of the direct current depends on volts/cm, pulse width, and the fluid conductivity. In some embodiments, the pulse has a frequency of about 0.001 to about 1000 Hz. In some embodiments, the pulse has a frequency from about 10 to about 200 Hz. In other embodiments, the pulse has a frequency of about 0.01 Hz-1000 Hz. In still other embodiments, the pulse has a frequency of about 0.1 Hz-1000 Hz, about 1 Hz-1000 Hz, about 1 Hz-500 Hz, about 1 Hz-400 Hz, about 1 Hz-300 Hz, or about 1 Hz-about 250 Hz. In some embodiments, the pulse has a frequency of about 0.1 Hz. In other embodiments, the pulse has a frequency of about 1 Hz. In still other embodiments, the pulse has a frequency of about 5 Hz, about 10 Hz, about 50 Hz, about 100 Hz, about 200 Hz, about 300 Hz, about 400 Hz, about 500 Hz, about 600 Hz, about 700 Hz, about 800 Hz, about 900 Hz or about 1000 Hz.

In other embodiments, the pulse has a duration of about 1 millisecond (ms)-1000 seconds (s). In some embodiments, the pulse has a duration of about 10 ms-1000 s. In still other embodiments, the pulse has a duration of about 100 ms-1000 s, about 1 s-1000 s, about 1 s-500 s, about 1 s-250 s or about 1 s-150 s. In some embodiments, the pulse has a duration of about 1 ms, about 10 ms, about 100 ms, about 1 s, about 2 s, about 3 s, about 4 s, about 5 s, about 6 s, about 7 s, about 8 s, about 9 s, about 10 s, about 20 s, about 50 s, about 100 s, about 200 s, about 300 s, about 500 s or about 1000s. In some embodiments, the pulse has a frequency of 0.2 to 200 Hz with duty cycles from 10-50%.

In some embodiments, the direct current is applied once, or as multiple pulses. Any suitable number of pulses may be applied including about 1-20 pulses. There is any suitable amount of time between pulses including about 1 millisecond-1000 seconds. In some embodiments, the pulse duration is 0.01 to 10 seconds.

In some embodiments, the cells are lysed using other methods in combination with a direct current applied to the isolated cells. In yet other embodiments, the cells are lysed without use of direct current. In various aspects, the devices and systems are capable of lysing cells with direct current in combination with other means, or may be capable of lysing cells without the use of direct current. Any method of cell lysis known to those skilled in the art may be suitable including, but not limited to application of a chemical lysing agent (e.g., an acid), an enzymatic lysing agent, heat, pressure, shear force, sonic energy, osmotic shock, or combinations thereof. Lysozyme is an example of an enzymatic-lysing agent.

Removal of Residual Material

In some embodiments, following concentration of the targeted cellular material in the second DEP field region, the method includes optionally flushing residual material from the targeted cellular material. In some embodiments, the devices or systems described herein are capable of optionally comprising a reservoir comprising a fluid suitable for flushing residual material from the targeted cellular material.

In some embodiments, the targeted cellular material is held near the array of electrodes, such as in the second DEP field region, by continuing to energize the electrodes. "Residual material" is anything originally present in the fluid, originally present in the cells, added during the procedure, created through any step of the process including but not limited to lysis of the cells (i.e. residual cellular material), and the like. For example, residual material includes non-lysed cells, cell wall fragments, proteins, lipids, carbohydrates, minerals, salts, buffers, plasma, and undesired nucleic acids. In some embodiments, the lysed cellular material comprises residual protein freed from the plurality of cells upon lysis. It is possible that not all of the targeted cellular material will be concentrated in the second DEP field. In some embodiments, a certain amount of targeted cellular material is flushed with the residual material.

In some embodiments, the residual material is flushed in any suitable fluid, for example in water, TBE buffer, or the like. In some embodiments, the residual material is flushed with any suitable volume of fluid, flushed for any suitable period of time, flushed with more than one fluid, or any other variation. In some embodiments, the method of flushing residual material is related to the desired level of isolation of the targeted cellular material with higher purity targeted cellular material requiring more stringent flushing and/or washing. In other embodiments, the method of flushing residual material is related to the particular starting material and its composition. In some instances, a starting material that is high in lipid requires a flushing procedure that involves a hydrophobic fluid suitable for solubilizing lipids.

In some embodiments, the method includes degrading residual material including residual protein. In some embodiments, the devices or systems are capable of degrading residual material including residual protein. For example, proteins are degraded by one or more of chemical degradation (e.g. acid hydrolysis) and enzymatic degradation. In some embodiments, the enzymatic degradation agent is a protease. In other embodiments, the protein degradation agent is Proteinase K. The optional step of degradation of residual material is performed for any suitable time, temperature, and the like. In some embodiments, the degraded residual material (including degraded proteins) is flushed from the nucleic acid.

In some embodiments, the agent used to degrade the residual material is inactivated or degraded. In some embodiments, the devices or systems are capable of degrading or inactivating the agent used to degrade the residual material. In some embodiments, an enzyme used to degrade the residual material is inactivated by heat (e.g., 50 to 95° C. for 5-15 minutes). For example, enzymes including proteases, (for example, Proteinase K) are degraded and/or inactivated using heat (typically, 15 minutes, 70° C.). In some embodiments wherein the residual proteins are degraded by an enzyme, the method further comprises inactivating the degrading enzyme (e.g., Proteinase K) following degradation of the proteins. In some embodiments, heat is provided by a heating module in the device (temperature range, e.g., from 30 to 95° C.).

The order and/or combination of certain steps of the method can be varied. In some embodiments, the devices or methods are capable of performing certain steps in any order or combination. For example, in some embodiments, the residual material and the degraded proteins are flushed in separate or concurrent steps. That is, the residual material is flushed, followed by degradation of residual proteins, followed by flushing degraded proteins from the nucleic acid. In some embodiments, one first degrades the residual proteins, and then flush both the residual material and degraded proteins from the nucleic acid in a combined step.

In some embodiments, the targeted cellular materials are retained in the device and optionally used in further procedures such as PCR or other procedures manipulating or amplifying nucleic acid. In some embodiments, the devices and systems are capable of performing PCR or other optional procedures. In other embodiments, the targeted cellular materials are collected and/or eluted from the device. In some embodiments, the devices and systems are capable of allowing collection and/or elution of targeted cellular material from the device or system. In some embodiments, the isolated cellular material is collected by (i) turning off the second dielectrophoretic field region; and (ii) eluting the material from the array in an eluant. Exemplary eluants include water, TE, TBE and L-Histidine buffer.

Nucleic Acids and Yields Thereof

In some embodiments, the method, device, or system described herein is optionally utilized to obtain, isolate, or separate any desired nucleic acid that may be obtained from such a method, device or system. Nucleic acids isolated by the methods, devices and systems described herein include DNA (deoxyribonucleic acid), RNA (ribonucleic acid), and combinations thereof. DNA can include cell-free DNA and DNA fragments. In some embodiments, the nucleic acid is isolated in a form suitable for sequencing or further manipulation of the nucleic acid, including amplification, ligation or cloning.

In some embodiments, the isolated, separated, or captured nucleic acid comprises DNA fragments that are selectively or preferentially isolated, separated, or captured based on their sizes. In some embodiments, the DNA fragments that are selectively or preferentially isolated, separated, or captured are between 250-600 bp, 250-275 bp, 275-300 bp, 300-325 bp, 325-350 bp, 350-375 bp, 375-400 bp, 400-425 bp, 425-450 bp, 450-475 bp, 475-500 bp, 500-525 bp, 525-550 bp, 550-575 bp, 575-600 bp, 300-400 bp, 400-500 bp, and/or 300-500 bp in length. In some embodiments, the DNA fragments that are selectively or preferentially isolated, separated, or captured are between 600-700 bp, 700-800 bp, 800-900 bp, 900-1000 bp, 1-2 kbp, 2-3 kbp, 3-4 kbp, 4-5 kbp, 5-6 kbp, 6-7 kbp, 7-8 kbp, 8-9 kbp, or 9-10 kbp. In some embodiments, the DNA fragments that are selectively or preferentially isolated, separated, or captured are greater than 300, 400, 500, 600, 700, 800, 900, or 1000 bp in size.

In some embodiments, the DNA fragments are cell-free DNA fragments.

In various embodiments, an isolated or separated nucleic acid is a composition comprising nucleic acid that is free from at least 99% by mass of other materials, free from at least 99% by mass of residual cellular material (e.g., from lysed cells from which the nucleic acid is obtained), free from at least 98% by mass of other materials, free from at least 98% by mass of residual cellular material, free from at least 95% by mass of other materials, free from at least 95% by mass of residual cellular material, free from at least 90% by mass of other materials, free from at least 90% by mass of residual cellular material, free from at least 80% by mass of other materials, free from at least 80% by mass of residual cellular material, free from at least 70% by mass of other materials, free from at least 70% by mass of residual cellular material, free from at least 60% by mass of other materials, free from at least 60% by mass of residual cellular material, free from at least 50% by mass of other materials, free from at least 50% by mass of residual cellular material, free from at least 30% by mass of other materials, free from at least 30% by mass of residual cellular material, free from at least 10% by mass of other materials, free from at least 10% by mass of residual cellular material, free from at least 5% by mass of other materials, or free from at least 5% by mass of residual cellular material.

In various embodiments, the nucleic acid has any suitable purity. For example, if a DNA sequencing procedure can work with nucleic acid samples having about 20% residual cellular material, then isolation of the nucleic acid to 80% is suitable. In some embodiments, the isolated nucleic acid comprises less than about 80%, less than about 70%, less than about 60%, less than about 50%, less than about 40%, less than about 30%, less than about 20%, less than about 10%, less than about 5%, or less than about 2% non-nucleic acid cellular material and/or protein by mass. In some embodiments, the isolated nucleic acid comprises greater than about 99%, greater than about 98%, greater than about 95%, greater than about 90%, greater than about 80%, greater than about 70%, greater than about 60%, greater than about 50%, greater than about 40%, greater than about 30%, greater than about 20%, or greater than about 10% nucleic acid by mass.

The nucleic acids are isolated in any suitable form including unmodified, derivatized, fragmented, non-fragmented, and the like. In some embodiments, the nucleic acid is collected in a form suitable for sequencing. In some embodiments, the nucleic acid is collected in a fragmented form suitable for shotgun-sequencing, amplification or other manipulation. The nucleic acid may be collected from the device in a solution comprising reagents used in, for example, a DNA sequencing procedure, such as nucleotides as used in sequencing by synthesis methods.

In some embodiments, the methods described herein result in an isolated nucleic acid sample that is approximately representative of the nucleic acid of the starting sample. In some embodiments, the devices and systems described herein are capable of isolating nucleic acid from a sample that is approximately representative of the nucleic acid of the starting sample. That is, the population of nucleic acids collected by the method, or capable of being collected by the device or system, are substantially in proportion to the population of nucleic acids present in the cells in the fluid. In some embodiments, this aspect is advantageous in applications in which the fluid is a complex mixture of many cell types and the practitioner desires a nucleic acid-based procedure for determining the relative populations of the various cell types.

In some embodiments, the nucleic acid isolated using the methods described herein or capable of being isolated by the devices described herein is high-quality and/or suitable for using directly in downstream procedures such as DNA sequencing, nucleic acid amplification, such as PCR, or other nucleic acid manipulation, such as ligation, cloning or further translation or transformation assays. In some embodiments, the collected nucleic acid comprises at most 0.01% protein. In some embodiments, the collected nucleic acid comprises at most 0.5% protein. In some embodiments, the collected nucleic acid comprises at most 0.1% protein. In some embodiments, the collected nucleic acid comprises at most 1% protein. In some embodiments, the collected nucleic acid comprises at most 2% protein. In some embodiments, the collected nucleic acid comprises at most 3% protein. In some embodiments, the collected nucleic acid comprises at most 4% protein. In some embodiments, the collected nucleic acid comprises at most 5% protein.

In some embodiments, the nucleic acid isolated by the methods described herein or capable of being isolated by the devices described herein has a concentration of at least 0.5 ng/mL. In some embodiments, the nucleic acid isolated by the methods described herein or capable of being isolated by the devices described herein has a concentration of at least 1 ng/mL. In some embodiments, the nucleic acid isolated by the methods described herein or capable of being isolated by the devices described herein has a concentration of at least 5 ng/mL. In some embodiments, the nucleic acid isolated by the methods described herein or capable of being isolated by the devices described herein has a concentration of at least 10 ng/ml.

In some embodiments, about 50 pico-grams of nucleic acid is isolated from about 5,000 cells using the methods, systems or devices described herein. In some embodiments, the methods, systems or devices described herein yield at least 10 pico-grams of nucleic acid from about 5,000 cells. In some embodiments, the methods, systems or devices described herein yield at least 20 pico-grams of nucleic acid from about 5,000 cells. In some embodiments, the methods, systems or devices described herein yield at least 50 pico-grams of nucleic acid from about 5,000 cells. In some embodiments, the methods, systems or devices described herein yield at least 75 pico-grams of nucleic acid from about 5,000 cells. In some embodiments, the methods, systems or devices described herein yield at least 100 pico-grams of nucleic acid from about 5,000 cells. In some embodiments, the methods, systems or devices described herein yield at least 200 pico-grams of nucleic acid from about 5,000 cells. In some embodiments, the methods, systems or devices described herein yield at least 300 pico-grams of nucleic acid from about 5,000 cells. In some embodiments, the methods, systems or devices described herein yield at least 400 pico-grams of nucleic acid from about 5,000 cells. In some embodiments, the methods, systems or devices described herein yield at least 500 pico-grams of nucleic acid from about 5,000 cells. In some embodiments, the methods, systems or devices described herein yield at least 1,000 pico-grams of nucleic acid from about 5,000 cells. In some embodiments, the methods, systems or devices described herein yield at least 10,000 pico-grams of nucleic acid from about 5,000 cells.

Assays and Applications

In some embodiments, the methods described herein further comprise optionally amplifying the isolated nucleic acid by polymerase chain reaction (PCR). In some embodiments, the PCR reaction is performed on or near the array of electrodes or in the device. In some embodiments, the device or system comprise a heater and/or temperature control mechanisms suitable for thermocycling.

PCR is optionally done using traditional thermocycling by placing the reaction chemistry analytes in between two efficient thermoconductive elements (e.g., aluminum or silver) and regulating the reaction temperatures using TECs. Additional designs optionally use infrared heating through optically transparent material like glass or thermo polymers. In some instances, designs use smart polymers or smart glass that comprise conductive wiring networked through the substrate. This conductive wiring enables rapid thermal conductivity of the materials and (by applying appropriate DC voltage) provides the required temperature changes and gradients to sustain efficient PCR reactions. In certain instances, heating is applied using resistive chip heaters and other resistive elements that will change temperature rapidly and proportionally to the amount of current passing through them.

In some embodiments, used in conjunction with traditional fluorometry (ccd, pmt, other optical detector, and optical filters), fold amplification is monitored in real-time or on a timed interval. In certain instances, quantification of final fold amplification is reported via optical detection converted to AFU (arbitrary fluorescence units correlated to analyze doubling) or translated to electrical signal via impedance measurement or other electrochemical sensing.

Given the small size of the micro electrode array, these elements are optionally added around the micro electrode array and the PCR reaction will be performed in the main sample processing chamber (over the DEP array) or the analytes to be amplified are optionally transported via fluidics to another chamber within the fluidic cartridge to enable on-cartridge Lab-On-Chip Processing In some instances, light delivery schemes are utilized to provide the optical excitation and/or emission and/or detection of fold amplification. In certain embodiments, this includes using the flow cell materials (thermal polymers like acrylic (PMMA) cyclic olefin polymer (COP), cyclic olefin co-polymer, (COC), etc. . . . ) as optical wave guides to remove the need to use external components. In addition, in some instances light sources—light emitting diodes—LEDs, vertical-cavity surface-emitting lasers—VCSELs, and other lighting schemes are integrated directly inside the flow cell or built directly onto the micro electrode array surface to have internally controlled and powered light sources. Miniature PMTs, CCDs, or CMOS detectors can also be built into the flow cell. This minimization and miniaturization enables compact devices capable of rapid signal delivery and detection while reducing the footprint of similar traditional devices (i.e. a standard bench top PCR/QPCR/Fluorometer).

Amplification on Chip

In some instances, silicon microelectrode arrays can withstand thermal cycling necessary for PCR. In some applications, on-chip PCR is advantageous because small amounts of target nucleic acids can be lost during transfer steps. In certain embodiments of devices, systems or processes described herein, any one or more of multiple PCR techniques are optionally used, such techniques optionally including any one or more of the following: thermal cycling in the flowcell directly; moving the material through microchannels with different temperature zones; and moving volume into a PCR tube that can be amplified on system or transferred to a PCR machine. In some instances, droplet PCR is performed if the outlet contains a T-junction that contains an immiscible fluid and interfacial stabilizers (surfactants, etc). In certain embodiments, droplets are thermal cycled in by any suitable method.

In some embodiments, amplification is performed using an isothermal reaction, for example, transcription mediated amplification, nucleic acid sequence-based amplification, signal mediated amplification of RNA technology, strand displacement amplification, rolling circle amplification, loop-mediated isothermal amplification of DNA, isothermal multiple displacement amplification, helicase-dependent amplification, single primer isothermal amplification or circular helicase-dependent amplification.

In various embodiments, amplification is performed in homogenous solution or as heterogeneous system with anchored primer(s). In some embodiments of the latter, the resulting amplicons are directly linked to the surface for higher degree of multiplex. In some embodiments, the amplicon is denatured to render single stranded products on or near the electrodes. Hybridization reactions are then optionally performed to interrogate the genetic information, such as single nucleotide polymorphisms (SNPs), Short Tandem Repeats (STRs), mutations, insertions/deletions, methylation, etc. Methylation is optionally determined by parallel analysis where one DNA sample is bisulfite treated and one is not. Bisulfite depurinates unmodified C becoming a U. Methylated C is unaffected in some instances. In some embodiments, allele specific base extension is used to report the base of interest.

Rather than specific interactions, the surface is optionally modified with nonspecific moieties for capture. For example, surface could be modified with polycations, i.e., polylysine, to capture DNA molecules which can be released by reverse bias (−V). In some embodiments, modifications to the surface are uniform over the surface or patterned specifically for functionalizing the electrodes or non electrode regions. In certain embodiments, this is accomplished with photolithography, electrochemical activation, spotting, and the like.

In some applications, a chip may include multiple regions, each region configured to capture DNA fragments of a specific or different size. Chip regions can sometimes vary with respect to voltage, amperage, frequency, pitch, electrode diameter, the depth of the well, or other factors to selectively capture fragments of different sizes in different regions. In some embodiments, each region comprises an array of multiple electrodes.

In various embodiments, devices or regions are run sequentially or in parallel. In some embodiments, multiple chip designs are used to narrow the size range of material collected creating a band pass filter. In some instances, current chip geometry (e.g., 80 um diameter electrodes on 200 um center-center pitch (80/200) acts as 500 bp cutoff filter (e.g., using voltage and frequency conditions around 10 Vpp and 10 kHz). In such instances, a nucleic acid of greater than 500 bp is captured, and a nucleic acid of less than 500 bp is not. Alternate electrode diameter and pitch geometries have different cutoff sizes such that a combination of chips should provide a desired fragment size. In some instances, a 40 um diameter electrode on 100 um center-center pitch (40/100) has a lower cutoff threshold, whereas a 160 um diameter electrode on 400 um center-center pitch (160/400) has a higher cutoff threshold relative to the 80/200 geometry, under similar conditions. In various embodiments, geometries on a single chip or multiple chips are combined to select for a specific sized fragments or particles. For example a 600 bp cutoff chip would leave a nucleic acid of less than 600 bp in solution, then that material is optionally recaptured with a 500 bp cutoff chip (which is opposing the 600 bp chip). This leaves a nucleic acid population comprising 500-600 bp in solution. This population is then optionally amplified in the same chamber, a side chamber, or any other configuration. In some embodiments, size selection is accomplished using a single electrode geometry, wherein nucleic acid of >500 bp is isolated on the electrodes, followed by washing, followed by reduction of the ACEK high field strength (change voltage, frequency, conductivity) in order to release nucleic acids of <600 bp, resulting in a supernatant nucleic acid population between 500-600 bp. In some embodiments, the device is configured to selectively capture nucleic acid fragments between 250-600 bp, 250-275 bp, 275-300 bp, 300-325 bp, 325-350 bp, 350-375 bp, 375-400 bp, 400-425 bp, 425-450 bp, 450-475 bp, 475-500 bp, 500-525 bp, 525-550 bp, 550-575 bp, 575-600 bp, 300-400 bp, 400-500 bp, and/or 300-500 bp in length.

In some embodiments, the chip device is oriented vertically with a heater at the bottom edge which creates a temperature gradient column. In certain instances, the bottom is at denaturing temperature, the middle at annealing temperature, the top at extension temperature. In some instances, convection continually drives the process. In some embodiments, provided herein are methods or systems comprising an electrode design that specifically provides for electrothermal flows and acceleration of the process. In some embodiments, such design is optionally on the same device or on a separate device positioned appropriately. In some instances, active or passive cooling at the top, via fins or fans, or the like, provides a steep temperature gradient. In some instances the device or system described herein comprises, or a method described herein uses, temperature sensors on the device or in the reaction chamber monitor temperature and such sensors are optionally used to adjust temperature on a feedback basis. In some instances, such sensors are coupled with materials possessing different thermal transfer properties to create continuous and/or discontinuous gradient profiles.

In some embodiments, the amplification proceeds at a constant temperature (i.e, isothermal amplification).

In some embodiments, the methods disclosed herein further comprise sequencing the nucleic acid isolated as disclosed herein. In some embodiments, the nucleic acid is sequenced by Sanger sequencing or next generation sequencing (NGS). In some embodiments, the next generation sequencing methods include, but are not limited to, pyrosequencing, ion semiconductor sequencing, polony sequencing, sequencing by ligation, DNA nanoball sequencing, sequencing by ligation, or single molecule sequencing.

In some embodiments, the isolated nucleic acids disclosed herein are used in Sanger sequencing. In some embodiments, Sanger sequencing is performed within the same device as the nucleic acid isolation (Lab-on-Chip). Lab-on-Chip workflow for sample prep and Sanger sequencing results would incorporate the following steps: a) sample extraction using ACE chips; b) performing amplification of target sequences on chip; c) capture PCR products by ACE; d) perform cycle sequencing to enrich target strand; e) capture enriched target strands; f) perform Sanger chain termination reactions; perform electrophoretic separation of target sequences by capillary electrophoresis with on chip multi-color fluorescence detection. Washing nucleic acids, adding reagent, and turning off voltage is performed as necessary. Reactions can be performed on a single chip with plurality of capture zones or on separate chips and/or reaction chambers.

In some embodiments, the method disclosed herein further comprise performing a reaction on the nucleic acids (e.g., fragmentation, restriction digestion, ligation of DNA or RNA). In some embodiments, the reaction occurs on or near the array or in a device, as disclosed herein.

Other Assays

The isolated nucleic acids disclosed herein may be further utilized in a variety of assay formats. For instance, devices which are addressed with nucleic acid probes or amplicons may be utilized in dot blot or reverse dot blot analyses, base-stacking single nucleotide polymorphism (SNP) analysis, SNP analysis with electronic stringency, or in STR analysis. In addition, such devices disclosed herein may be utilized in formats for enzymatic nucleic acid modification, or protein-nucleic acid interaction, such as, e.g., gene expression analysis with enzymatic reporting, anchored nucleic acid amplification, or other nucleic acid modifications suitable for solid-phase formats including restriction endonuclease cleavage, endo- or exo-nuclease cleavage, minor groove binding protein assays, terminal transferase reactions, polynucleotide kinase or phosphatase reactions, ligase reactions, topoisomerase reactions, and other nucleic acid binding or modifying protein reactions.

In addition, the devices disclosed herein can be useful in immunoassays. For instance, in some embodiments, locations of the devices can be linked with antigens (e.g., peptides, proteins, carbohydrates, lipids, proteoglycans, glycoproteins, etc.) in order to assay for antibodies in a bodily fluid sample by sandwich assay, competitive assay, or other formats. Alternatively, the locations of the device may be addressed with antibodies, in order to detect antigens in a sample by sandwich assay, competitive assay, or other assay formats. As the isoelectric point of antibodies and proteins can be determined fairly easily by experimentation or pH/charge computations, the electronic addressing and electronic concentration advantages of the devices may be utilized by simply adjusting the pH of the buffer so that the addressed or analyte species will be charged.

In some embodiments, the isolated nucleic acids are useful for use in immunoassay-type arrays or nucleic acid arrays.

Definitions and Abbreviations

The articles "a", "an" and "the" are non-limiting. For example, "the method" includes the broadest definition of the meaning of the phrase, which can be more than one method.

"Vp-p" is the peak-to-peak voltage.

"TBE" is a buffer solution containing a mixture of Tris base, boric acid and EDTA.

"TE" is a buffer solution containing a mixture of Tris base and EDTA.

"L-Histidine buffer" is a solution containing L-histidine.

"DEP" is an abbreviation for dielectrophoresis.

EXAMPLES

Example 1: Chip Construction

A 45×20 custom 80 μm diameter circular platinum microelectrode array on 200 um center-center pitch was fabricated based upon previous results (see references 1-3, below). All 900 microelectrodes are activated together and AC biased to form a checkerboard field geometry. The positive DEP regions occur directly over microelectrodes, and negative low field regions occur between microelectrodes. The array is over-coated with a 200 nm-500 nm thick porous poly-Hema hydrogel layer (Procedure: 12% pHema in ethanol stock solution, purchased from PolySciences Inc., that is diluted to 5% using ethanol. 70 uL of the 5% solution is spun on the above mentioned chip at a 6K RPM spin speed using a spin coater. The chip+hydrogel layer is then put in a 60° C. oven for 45 minutes) and enclosed in a microfluidic cartridge, forming a 50 μL sample chamber covered with an acrylic window. Electrical connections to microelectrodes are accessed from Molex connectors from the PCB board in the flow cell. A function generator (HP 3245A) provided sinusoidal electrical signal at 10 KHz and 10-14V peak-peak, depending on solution conductivity. Images were captured with a fluorescent microscope (Leica) and an EGFP cube (485 nm emission and 525 nm excitation bandpass filters). The excitation source was a PhotoFluor II 200 W Hg arc lamp.

[1] R. Krishnan, B. D. Sullivan, R. L. Mifflin, S. C. Esener, and M. J. Heller, "Alternating current electrokinetic separation and detection of DNA nanoparticles in high-conductance solutions." Electrophoresis, vol. 29, pages 1765-1774, 2008.

[2] R. Krishnan and M. J. Heller, "An AC electrokinetic method for enhanced detection of DNA nanoparticles." J. Biophotonics, vol. 2, pages 253-261, 2009.

[3] R. Krishnan, D. A. Dehlinger, G. J. Gemmen, R. L. Mifflin, S. C. Esener, and M. J. Heller, "Interaction of nanoparticles at the DEP microelectrode interface under high conductance conditions" Electrochem. Comm., vol. 11, pages 1661-1666, 2009.

Example 2: Isolation of Human Genomic DNA

Figure 2:
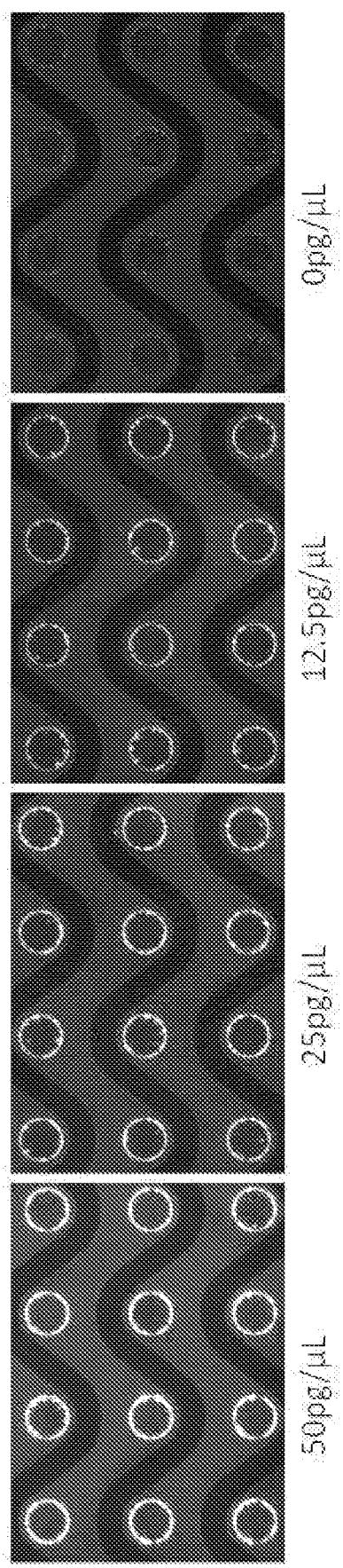
FIG. 2 shows the electrodes associated with various amounts of genomic DNA.

Human Genomic DNA (gDNA) was purchased from Promega (Promega, Madison, Wis.) and was sized to 20-40 kbp. (Sizing gel not shown.) The gDNA was diluted in DI water to the following concentrations: 50 nanograms, 5 nanograms, 1 nanogram, and 50 picograms. The gDNA was stained using 1×SYBR Green I green fluorescent double stranded DNA dye purchased from Invitrogen (Life Technologies, Carlsbad, Calif.). This mixture was then inserted into the microelectrode arrays and run at 14 Volts peak to peak (Vp-p), at 10 kHz sine wave for 1 minute. At the conclusion of 1 minute, a picture of the microelectrode pads was taken using a CCD camera with a 10× objective on a microscope using green fluorescence filters (FITC) so that the gDNA could be visualized (FIG. 2) The chip was able to identify down to 50 pg of gDNA in 50 μL water, i.e. 1 ng/mL concentration. Additionally, at 50 picograms, each microelectrode had on average ~60 femtograms of DNA since there are 900 microelectrodes on the array. The low-level concentration ability of the ACE device is well within the range of 1-10 ng/mL needed to identify Cfc-DNA biomarkers in plasma and serum (see references 4-6 below).

[4] T. L. Wu et al, "Cell-free DNA: measurement in various carcinomas and establishment of normal reference range." Clin Chim Acta., vol. 21, pages 77-87, 2002.

[5] R. E. Board et al, "DNA Methylation in Circulating Tumour DNA as a Biomarker for Cancer", Biomarker Insights, vol. 2, pages 307-319, 2007.

[6] O. Gautschi et al, "Circulating deoxyribonucleic Acid as prognostic marker in non-small-cell lung cancer patients undergoing chemotherapy." J Clin Oncol., vol. 22, pages 4157-4164, 2004.

Example 3: Formation of Hydrogel with GVD

Hydrogel, such as polyhydroxyethylmethacrylate (pHEMA) may also be layered onto the chip surface via vapor deposition using proprietary assays developed by GVD Corporation (Cambridge, Mass.) (see www.gvdcorp.com). Hydrogels such as pHEMA were deposited in various thickness (100, 200, 300, 400 nm) and crosslinking (5, 25, 40%) density on electrode chips was performed using technology developed by GVD Corporation. The hydrogel films were tested using a standard ACE protocol (no pretreatment, 7 Vp-p, 10 KHz, 2 minutes, 0.5×PBS, 500 ng/ml gDNA labeled with Sybr Green 1). Fluorescence on the electrodes was captured by imaging. The process could also be optimized by changing the deposition rate or anchoring growth to the surface of the microelectrode array (i.e., to the passivation layer and exposed electrodes), using an adhesion promoter such as a silane derivative.

Example 4: Performance of Disclosed Device and Method v. Conventional Method

QIAGEN® circulating nucleic acid Purification kit (cat #55114) was used to purify 1 ml of plasma from chronic lymphocytic leukemia (CLL) patients, according to manufacturer's protocol. Briefly, incubation of 1 ml plasma with Proteinase K solution was performed for 30 minutes at 60° C. The reaction was quenched on ice and the entire volume was applied to a QIAamp Mini column connected to a vacuum. The liquid was pulled through the column and washed with 3 different buffers (600-750 ul each). The column was centrifuged at 20,000×g, 3 minutes and baked at 56° C. for 10 minutes to remove excess liquid. The sample was eluted in 55 µl of elution buffer with 20,000×g, 1 minute centrifugation. Total processing time was ~2.5 hours.

The chip die size was 10×12 mm, with 60-80 µm diameter Pt electrodes on 180-200 µm center-to-center pitch, respectively. The array was overcoated with a 5% pHEMA hydrogel layer (spun cast 6000 rpm from Ethanol solution, 12% pHEMA stock from Polysciences). The chip was pretreated using 0.5×PBS, 2V rms, 5 Hz, 15 seconds. The buffer was removed and 25 µl of CLL patient plasma was added. DNA was isolated for 3 minutes at 11 V p-p, 10 Khz, then washed with 500 µl of TE buffer at a 100 µl/min flow rate, with power ON. The voltage was turned off and the flow cell volume was eluted into a microcentrifuge tube. Total processing time was ~10 minutes.

The same process can be applied to fresh whole blood without modification. Ability to extract and purify DNA from whole undiluted blood is uniquely enabled by the chip technology disclosed herein.

DNA quantitation was performed on the Qiagen and chip elutes using PicoGreen according to manufacturer's protocol (Life Tech) (Table 2).

Subsequent gel electrophoresis, PCR and Sanger sequencing reactions showed similar performance for both extraction techniques with the chip being able to process whole blood as well as plasma. Mann-Whitney U non-parametric statistical test was also run between DNA amounts isolated from plasma using the Qiagen and chip techniques. There was no statistical difference (p<0.05 two-tailed) using either method of DNA purification.

TABLE 2

DNA purification, chip v. Qiagen
Values are in ng/ml and normalized to original
plasma sample volume for comparison purposes.

| Patient | Chip - plasma | Qiagen - plasma | Chip - blood |
|---|---|---|---|
| normal A | 139 | 39 | 274 |
| normal B | 206 | 80 | 114 |
| normal C | 133 | 32 | 97 |
| BD 528 | 320 | 547 | 167 |
| BD 851 | 218 | 393 | 307 |
| BD 1044 | 285 | 424 | 794 |
| BD 334 | 261 | 1387 | 666 |
| BD 613 | 179 | 53 | 257 |
| BD 762 | 145 | 367 | 314 |
| BD 847 | 886 | 1432 | 811 |
| BD 248 | 84 | 119 | 448 |
| BD 1024 | 302 | 169 | 332 |
| BD 1206 | 584 | 396 | 1435 |
| BD 1217 | 496 | 146 | 584 |
| BD 1262 | 87 | 84 | 1592 |
| BD 1311 | 119 | 257 | 1825 |

Example 5: Detection of Multiple Biomarkers

Plasma was isolated from a whole-blood sample from a series of patients using standard techniques. Some of the patients were healthy controls while other patients were known to have non-small cell lung cancer.

Cell-free DNA fragments in each sample were stained using 1×SYBR Green I green fluorescent double stranded DNA dye purchased from Invitrogen (Life Technologies, Carlsbad, Calif.). Each mixture was then inserted into a microelectrode array and run at 14 Volts peak to peak (Vp-p), at 10 kHz sine wave for 1 minute. The samples were subsequently stained with a rabbit anti-human PD-L1 (28-8) antibody conjugated to Alexa Fluor 594.

Figure 7:
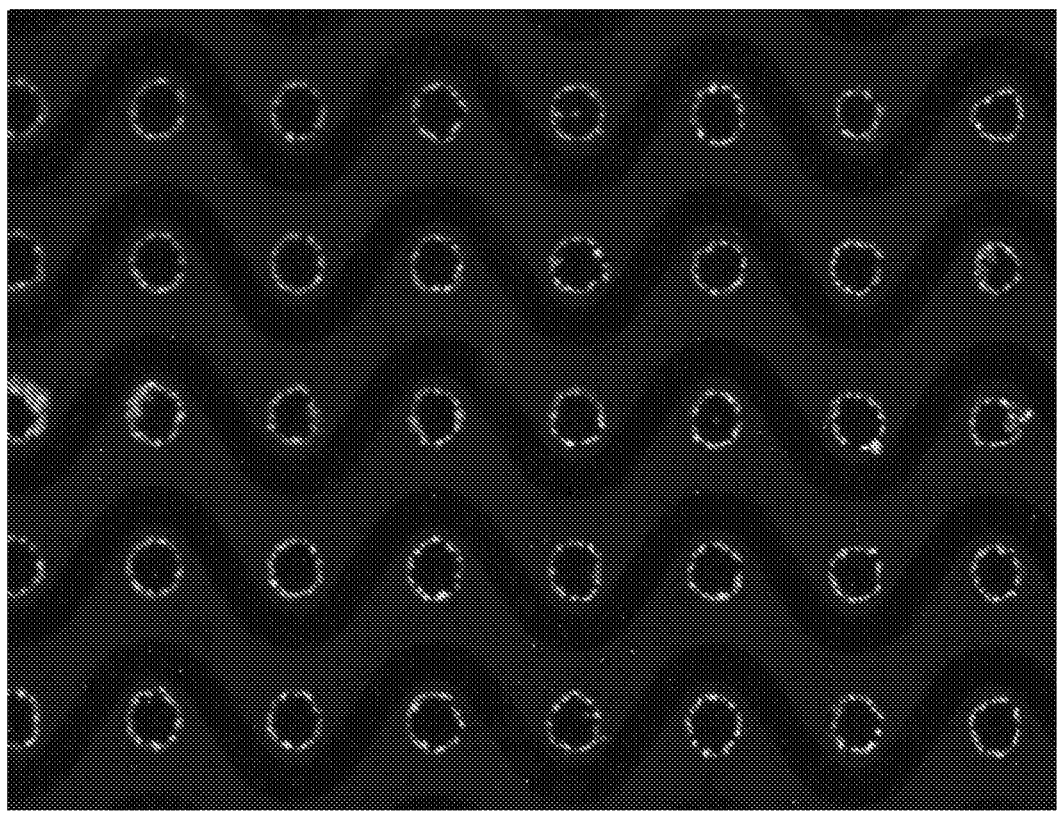
FIG. 7 shows a merged image of cfDNA (green) and PD-L1 protein staining (red) as visualized on an electrode array. The sample is from a patient with non-small cell lung cancer.

Pictures of the microelectrode pads were taken using a CMOS camera with a 4× objective on a microscope using blue/green fluorescence filters (FITC) so that the cfDNA could be visualized and green/orange fluorescence filters (TRITC) to image the Alexa Fluor 594. The amounts of cfDNA and PD-L1 were determined for each sample and the images were merged (FIG. 7). The quantities of cfDNA and PD-L1 in each sample were plotted on an XY scatter chart (FIG. 8). The results show that the samples from healthy controls contained low amounts of cfDNA and PD-L1. In contrast, most of the samples from cancer patients were high for both cfDNA and PD-L1. Surprisingly, some samples only showed elevated levels of one of the two markers. For example, one sample was particularly high for PD-L1 staining but had relatively normal levels of cfDNA (dot notated with a diamond, bottom right of plot). The ability to simultaneously detect both cfDNA and PD-L1 levels allowed this sample to be correctly determined to be from a patient with cancer.

Example 6: Isolation and Quantification of Cell-Free DNA from Plasma Obtained from Healthy Patients and Cancer Patients Plasma samples were obtained from 52 healthy patients and 53 cancer patients. Cell-free DNA fragments greater than 300 bp in size were isolated from the plasma on the devices disclosed herein as described in Example 1. The DNA was labeled using SYBR Green staining and quantified using a CMOS sensor attached to a 4× objective. The amount of cell-free DNA was then quantified for each sample in pictograms per microliter of plasma.

Figure 9:
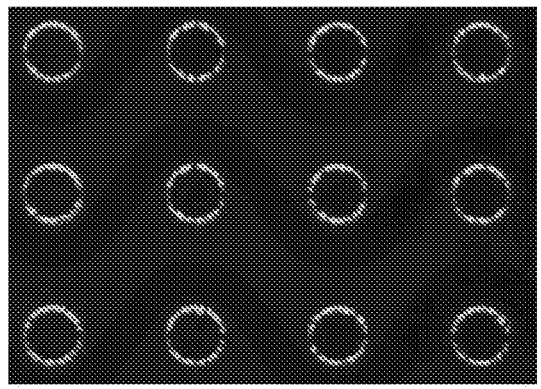
FIG. 9 shows the results of plasma samples from patients with adenocarcinoma, squamous cell cancer, and ovarian cancer, and a healthy control, that were isolated using the devices described herein.
Figure 9:
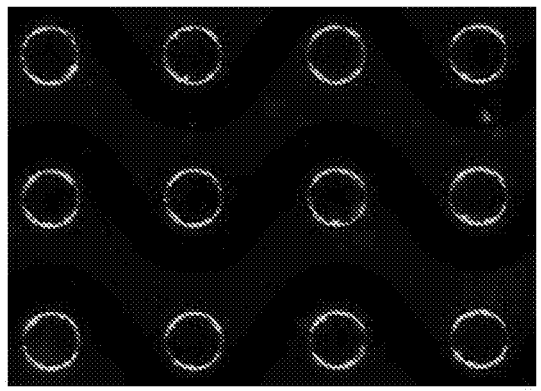
Figure 9:
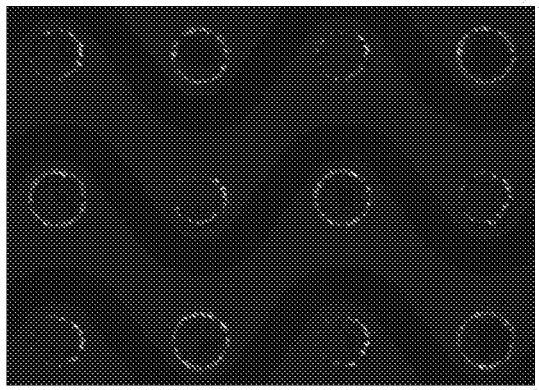
Figure 9:
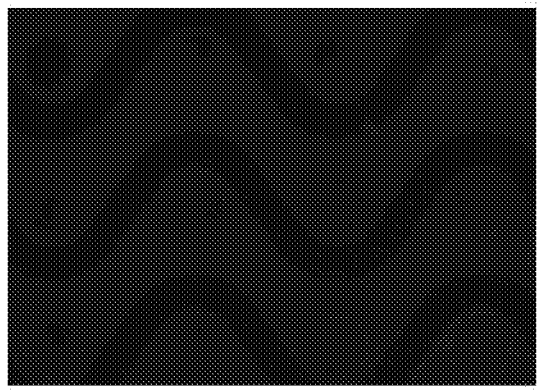
Figure 10:
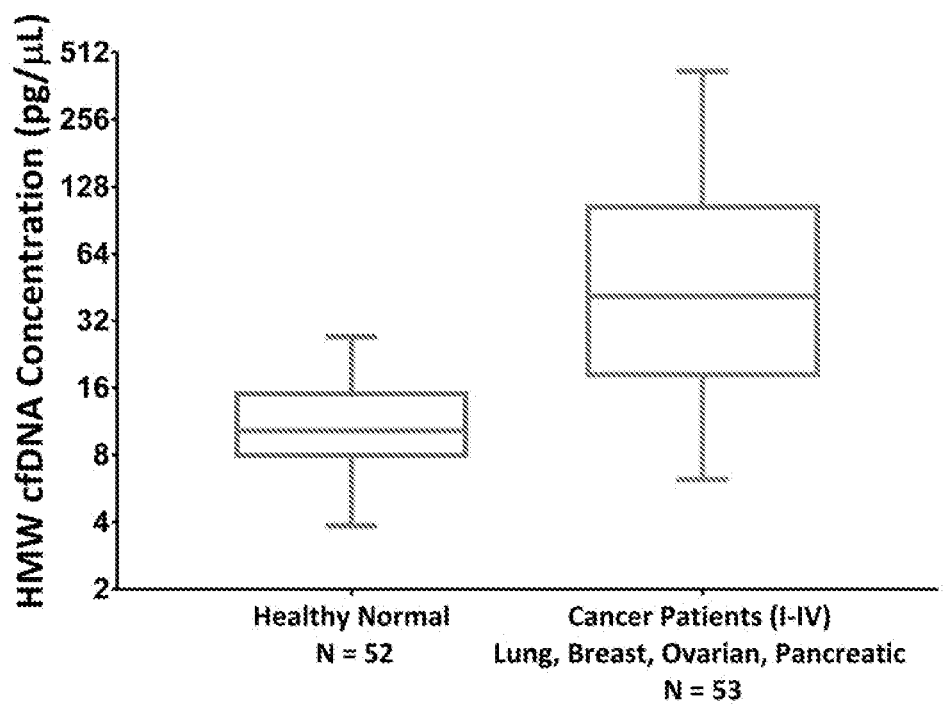
FIG. 10 shows a comparison of cfDNA concentrations for 52 healthy patients and 53 cancer patients (lung, breast, ovarian, and pancreatic cancers).

FIG. 9 shows the results of samples from patients with adenocarcinoma, squamous cell cancer, and ovarian cancer, and a healthy control. FIG. 10 shows a comparison of cfDNA concentrations for 52 healthy patients and 53 cancer patients (lung, breast, ovarian, and pancreatic cancers). The results show an increase in cfDNA concentrations for fragments above 300 bp in size in cancer patients as compared to healthy controls.

Example 7: Tracking Therapeutic Response Using Cell-Free DNA Quantification

Figure 11A:
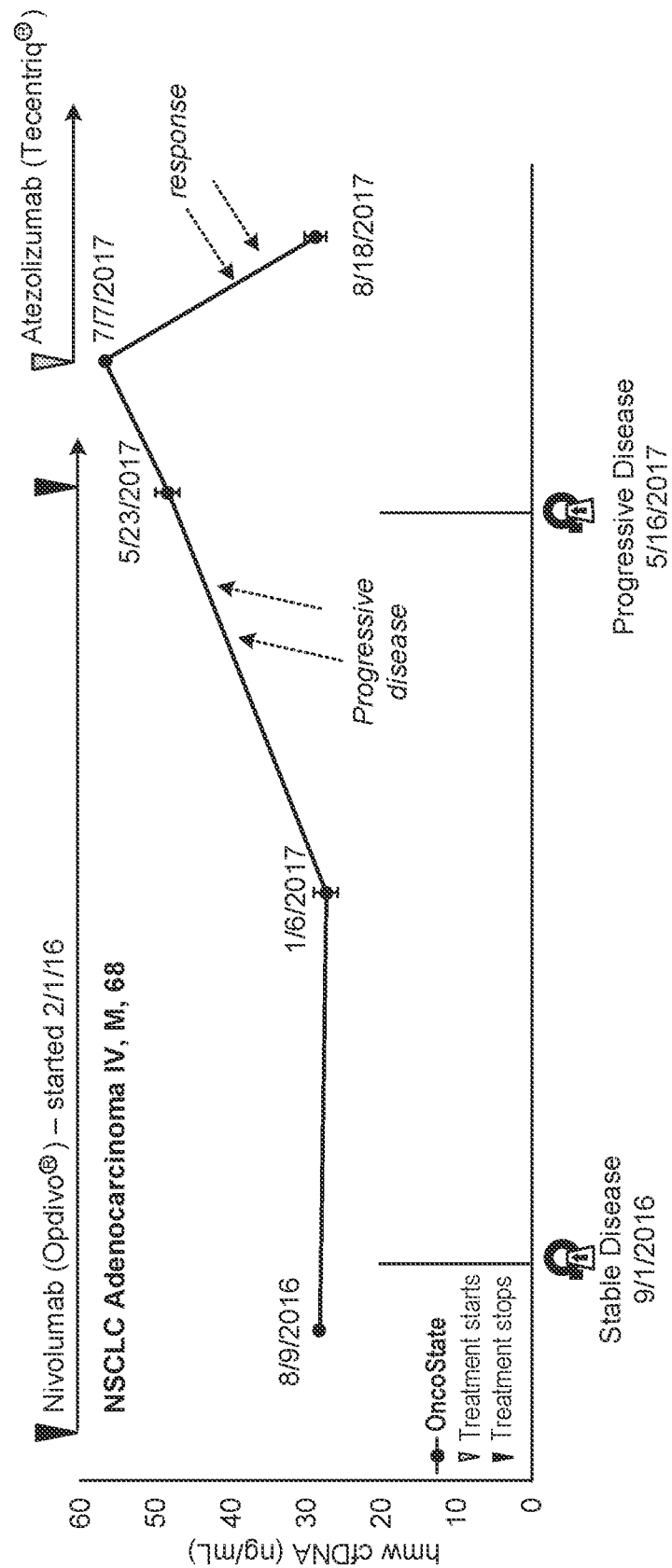

Plasma samples were obtained over the course of treatment for two patients with stage IV adenocarcinoma receiving nivolumab (Opdivo) therapy. The samples were processed and analyzed as described in Example 2. The results are shown in FIG. 11A and FIG. 11B. The patient in FIG. 11A failed to respond to nivolumab treatment, which is shown by a constant level of detected cfDNA after treatment, and then began to show signs of disease progression. The patient was subsequently administered atezolizumab (Tecentriq), to which he responded. The response is indicated by a decrease in cfDNA concentration. The results show that the concentration of cfDNA larger than 300 bp decreases as patients respond to therapy and increases as the disease progresses. The figures show the concentration of cdDNA on the Y axis as ng/mL and the X axis represents time.

Example 8: Isolation and Detection of RNA

The supernatant from an ASPC-1 pancreatic cancer cell line culture was ultracentrifuged and stained in-situ using SYTO RNASelect. The resulting product was pooled and spiked into LiHep plasma samples at varying concentrations (0×, 1×, and 10×). The samples were then captured by microelectrode arrays. The results were imaged, as shown in FIG. 12A.

RNA was also isolated from plasma obtained from non-small cell lung cancer and healthy patients using microelectrodes. The resulting RNA was stained with SYTO RNASelect. The results are shown in FIG. 12B.

Example 9: Isolation and Detection of Carcinoembryonic Antigen (CEA)

Plasma from patients with adenocarcinoma was obtained. The samples were then analyzed by microelectrode arrays. A labeled antibody against human CEA was used to stain the resulting material collected by the electrodes. Some samples were artificially spiked with 2 g/mL of naked CEA protein. The results show that exosome-bound CEA, but not naked CEA, was stained by the antibody (FIG. 13). Thus, the results show that exosome-bound CEA was retained by the microelectrodes.

Example 10: Isolation and Quantification of Cell-Free DNA from Plasma Obtained from Sepsis Patients Plasma samples were obtained from healthy patients and patients suffering from sepsis. Cell-free DNA fragments greater than 300 bp in size were isolated from the plasma on the microelectrode devices disclosed herein as described in Example 1. The DNA was labeled using SYBR Green staining and quantified using a CMOS sensor attached to a 4× objective. The amount of cell-free DNA was then quantified for each sample in pictograms per microliter of plasma.

FIG. 14 shows the results of samples from patients with sepsis and a healthy control. FIG. 15 shows a comparison of cfDNA concentrations for the healthy patient and each of the two sepsis patients. The results show an increase in cfDNA concentrations for fragments above 300 bp in size in sepsis patients as compared to healthy controls.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for analyzing a biological sample comprising:
capturing a plurality of analytes in the biological sample using an electrode configured to generate an AC dielectrophoretic field, wherein the plurality of analytes comprises at least two types of analytes selected from the group consisting of DNA, RNA, nucleosomes, exosomes, extracellular vesicles, proteins, cell membrane fragments, mitochondria and cellular vesicles; and
detecting the plurality of analytes, wherein detecting the plurality of analytes comprises detecting at least two different species of DNA, RNA, nucleosomes, exosomes, extracellular vesicles, proteins, cell membrane fragments, mitochondria or cellular vesicles.

2. The method of claim 1, wherein the capturing the plurality of analytes in the biological sample comprises using electrodes configured to generate a dielectrophoretic low field region and a dielectrophoretic high field region.

3. The method of claim 2, wherein capturing the plurality of analytes in the biological sample comprises preferentially capturing a first analyte using a first electrode and a second analyte using a second electrode.

4. The method of claim 2, wherein capturing the plurality of analytes in the biological sample comprises capturing more than one analyte on the same electrode.

5. The method of claim 1, wherein the DNA comprises cell-free DNA.

6. The method of claim 1, wherein the detecting comprises quantifying at least two types of analytes in the plurality of analytes.

7. The method of claim 6, wherein the method performance is characterized by an area under the receiver operating characteristic (ROC) curve (AUC) ranging from 0.60 to 0.70, 0.70 to 0.79, 0.80 to 0.89, or 0.90 to 1.00.

8. The method of claim 1, wherein the biological sample is obtained from a subject and comprises a bodily fluid, blood, serum, plasma, urine, saliva, cells, tissue, or a combination thereof.

9. The method of claim 8, wherein the biological sample comprises cells and the method further comprises lysing the cells.

10. The method of claim 8, further comprising detecting a disease or condition in the subject using the at least two types of analytes detected in the biological sample.

11. The method of claim 10, wherein the disease or condition is cancer.

12. The method of claim 11, wherein detecting further comprises determining a type of cancer, a stage of cancer, an increase in tumor burden relative to an earlier time point, a decrease in tumor burden relative to an earlier time point, no change in tumor burden relative to an earlier time point, or the efficacy of a cancer therapy, or the absence of cancer.

13. The method of claim 1, wherein the detecting comprises contacting an analyte of the plurality of analytes with an antibody that specifically binds to an analyte.

14. The method of claim 13, wherein the antibody comprises a detectable label.

15. The method of claim 14, wherein the detectable label comprises a fluorescent moiety.

16. The method of claim 1, wherein detecting comprises at least one of the group consisting of Quantitative Real Time PCR, enzyme-linked immunosorbent assay (ELISA), direct SYBR gold assay, direct PicoGreen assay, loss of heterozygosity (LOH) of microsatellite marker assay, electrophoresis, methylation analysis, MALDI-ToF, PCR, and digital PCR.

17. The method of claim 1, further comprising eluting the analytes from the electrode after the capturing.

18. The method of claim 2, wherein the dielectrophoretic low field region is produced using an alternating current having a voltage of 1 volt to 40 volts peak-peak; and/or a frequency of 5 Hz to 5,000,000 Hz.

19. The method of claim 2, wherein the dielectrophoretic high field region is produced using an alternating current having a voltage of 1 volt to 40 volts peak-peak; and/or a frequency of 5 Hz to 5,000,000 Hz.

20. The method of claim 1, wherein at least one of the two analytes is an exosome.

* * * * *